(12) United States Patent
Starke et al.

(10) Patent No.: US 7,192,945 B2
(45) Date of Patent: *Mar. 20, 2007

(54) BENZOTHIAZEPINE DERIVATIVES

(75) Inventors: Ingemar Starke, Molndal (SE); Mikael Dahlstrom, Molndal (SE); David Blomberg, Molndal (SE)

(73) Assignee: AstraZeneca AB, Sodertalje (SE)

( * ) Notice: Subject to any disclaimer, the term of this patent is extended or adjusted under 35 U.S.C. 154(b) by 369 days.

This patent is subject to a terminal disclaimer.

(21) Appl. No.: 10/451,262

(22) PCT Filed: Dec. 17, 2001

(86) PCT No.: PCT/GB01/05554

§ 371 (c)(1), (2), (4) Date: Jun. 20, 2003

(87) PCT Pub. No.: WO02/50051

PCT Pub. Date: Jun. 27, 2002

(65) Prior Publication Data

US 2004/0067933 A1    Apr. 8, 2004

(30) Foreign Application Priority Data

Dec. 21, 2000 (SE) .................................. 0004811
May 24, 2001 (GB) .................................. 0112592.1

(51) Int. Cl.
A61P 3/06 (2006.01)
A61K 31/55 (2006.01)
C07D 281/10 (2006.01)

(52) U.S. Cl. .................. 514/211.09; 540/552
(58) Field of Classification Search ........... 514/211.09; 540/552
See application file for complete search history.

(56) References Cited

U.S. PATENT DOCUMENTS 6,906,058 B2 * 6/2005 Starke et al. ............. 514/211.1
2002/0142054 A1 10/2002 Marlett et al. ............. 424/738

FOREIGN PATENT DOCUMENTS

| DE | 19825804 | 12/1999 |
|---|---|---|
| EP | 0372542 A | 6/1990 |
| EP | 0 864 582 | 9/1998 |
| GB | 2262888 | 7/1993 |
| WO | 93/16055 | 8/1993 |
| WO | 94/18183 | 8/1994 |
| WO | 94/18184 | 8/1994 |
| WO | 96/05188 | 2/1996 |
| WO | 96/08484 | 3/1996 |
| WO | 96/16051 A | 5/1996 |
| WO | 97/33882 | 9/1997 |
| WO | 98/38182 | 9/1998 |
| WO | 98/40375 | 9/1998 |
| WO | 99/01149 | 1/1999 |
| WO | 99/32478 | 7/1999 |
| WO | 99/35135 A | 7/1999 |
| WO | 99/64409 | 12/1999 |
| WO | 99/64410 | 12/1999 |
| WO | 00/01687 | 1/2000 |
| WO | 00/38725 | 7/2000 |
| WO | 00/38726 | 7/2000 |
| WO | 00/38727 | 7/2000 |
| WO | 00/38728 | 7/2000 |

(Continued)

OTHER PUBLICATIONS

Govers et al., Journal of Lipid Research, 35(5), 1994, pp. 741-748.
Higaki et al., Arteriosclerosis, Thrombosis, and Vascular Biology, 18(8), 1998, pp. 1304-1311.
Ishibashi et al., Journal of Clinical Investigation, 92(2), 1993, pp. 883-893.
Lewis et al., Journal of Lipid Research, 36, 1995, pp. 1098-1105.
Plump et al., Cell, (71), 1992, pp. 343-353.
Schiller, Alimentary Pharmacology and Therapeutics, 15(6), 2001, pp. 749-763.

(Continued)

Primary Examiner—Brenda Coleman
(74) Attorney, Agent, or Firm—Morgan, Lewis & Bockius LLP

(57) ABSTRACT

The present invention relates to compounds of the formula (I): (wherein variable groups are as defined within) pharmaceutically acceptable salts, solvates, solvates of such salts and prodrugs thereof and their use as ileal bile acid transport (IBAT) inhibitors for the treatment of hyperlipidaemia. Processes for their manufacture and pharmaceutical compositions containing them are also described

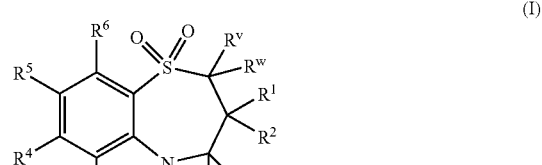

(I)

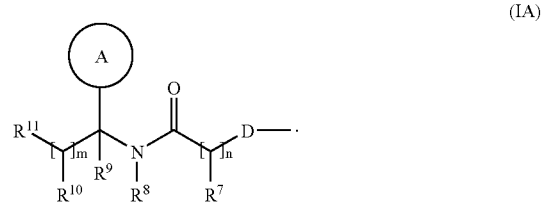

(IA)

18 Claims, No Drawings

FOREIGN PATENT DOCUMENTS

| | | |
|---|---|---|
| WO | 00/38729 | 7/2000 |
| WO | 00/47568 | 8/2000 |
| WO | 00/61568 | 10/2000 |
| WO | 00/62810 | 10/2000 |
| WO | 01/60807 A1 | 8/2001 |
| WO | 01/66533 A | 9/2001 |
| WO | 01/68096 A2 | 9/2001 |
| WO | 01/68637 A2 | 9/2001 |
| WO | 02/08211 A2 | 1/2002 |
| WO | 02/32428 A2 | 4/2002 |
| WO | 02/053548 A1 | 7/2002 |
| WO | 03/020710 A1 | 3/2003 |
| WO | 03/022286 | 3/2003 |
| WO | 03/022825 A1 | 3/2003 |
| WO | 03/022830 A1 | 3/2003 |
| WO | 03/061663 A1 | 7/2003 |
| WO | 03/091232 A2 | 11/2003 |
| WO | 03/106482 A2 | 12/2003 |
| WO | 2004/006899 A1 | 1/2004 |
| WO | 2004/076430 A1 | 9/2004 |
| WO | 2004/089350 A1 | 10/2004 |

OTHER PUBLICATIONS

Sprong et al., J. Nutrition (US), 132(6), 2002, pp. 1269-1274.
Van Tilburg et al., Gastroenterology, 98(1), 1989, pp. 25-32.
Welberg et al., Scandinavian J. Gastroenterology Suppl Norway, 188, 1991, pp. 52-59.

* cited by examiner

BENZOTHIAZEPINE DERIVATIVES

This application is a national stage entry under 35 U.S.C. § 371 of PCT/GB01/05554, filed Dec. 17, 2001.

This invention relates to benzothiazepine derivatives, or pharmaceutically acceptable salts, solvates, solvates of such salts and prodrugs thereof. These benzothiazepines possess ileal bile acid transport (IBAT) inhibitory activity and accordingly have value in the treatment of disease states associated with hyperlipidaemic conditions and they are useful in methods of treatment of a warm-blooded animal, such as man. The invention also relates to processes for the manufacture of said benzothiazepine derivatives, to pharmaceutical compositions containing them and to their use in the manufacture of medicaments to inhibit IBAT in a warm-blooded animal, such as man.

It is well-known that hyperlipidaemic conditions associated with elevated concentrations of total cholesterol and low-density lipoprotein cholesterol are major risk factors for cardiovascular atherosclerotic disease (for instance "Coronary Heart Disease: Reducing the Risk; a Worldwide View" Assman G., Carmnena R. Cullen P. et al; Circulation 1999, 100, 1930–1938 and "Diabetes and Cardiovascular Disease: A Statement for Healthcare Professionals from the American Heart Association" Grundy S, Benjamin I., Burke G., et al; Circulation, 1999, 100, 1134–46). Interfering with the circulation of bile acids within the lumen of the intestinal tracts is found to reduce the level of cholesterol. Previous established therapies to reduce the concentration of cholesterol involve, for instance, treatment with HMG-CoA reductase inhibitors, preferably statins such as simvastatin and fluvastatin, or treatment with bile acid binders, such as resins. Frequently used bile acid binders are for instance cholestyramine and cholestipol. One recently proposed therapy ("Bile Acids and Lipoprotein Metabolism: a Renaissance for Bile Acids in the Post Statin Era" Angelin B, Eriksson M, Rudling M; Current Opinion on Lipidology, 1999, 10, 269–74) involved the treatment with substances with an IBAT inhibitory effect.

Re-absorption of bile acid from the gastrointestinal tract is a normal physiological process which mainly talkes place in the ileum by the IBAT mechanism. Inhibitors of IBAT can be used in the treatment of hypercholesterolaemia (see for instance "Interaction of bile acids and cholesterol with nonsystemic agents having hypocholesterolaemic properties", Biochemica et Biophysica Acta, 1210 (1994) 255–287). Thus, suitable compounds having such inhibitory IBAT activity are also useful in the treatment of hyperlipidaemic conditions. Compounds possessing such IBAT inhibitory activity have been described, see for instance compounds described in WO 93/16055, WO 94/18183, WO 94/18184, WO 96/05188, WO 96/08484, WO 96/16051, WO 97/33882, WO98/38182, WO 99/35135, WO 98/40375, WO 99/35153, WO 99/64409, WO 99/64410, WO 00/01687, WO 00/47568, WO 00/61568, WO 01/68906, DE 19825804, WO 00/38725, WO 00/38726, WO 00/38727, WO 00/38728, WO 00/38729, WO 01/68906, and EP 0 864 582.

A further aspect of this invention relates to the use of the compounds of the invention in the treatment of dyslipidemic conditions and disorders such as hyperlipidaemia, hypertriglicridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL). In addition, these compounds are expected to be useful for the prevention and treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocyte, monocytes and/or macrophage infiltrate, intimital thickening, medial thinning, infectious and surgical trauma and vascular thrombosis, stroke and transient ischaeemic attacks.

The present invention is based on the discovery that certain benzothiazepine compounds surprisingly inhibit IBAT. Such properties are expected to be of value in the treatment of disease states associated with hyperlipidaemic conditions.

Accordingly, the present invention provides a compound of formula (I):

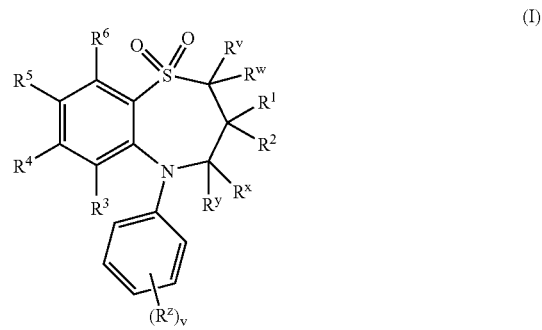

wherein:

$R^v$ and $R^w$ are independently selected from hydrogen or $C_{1-6}$alkyl;

$R^1$ and $R^2$ are independently selected from $C_{1-6}$alkyl;

$R^x$ and $R^y$ are independently selected from hydrogen or $C_{1-6}$alkyl, or one of $R^x$ and $R^y$ is hydrogen or $C_{1-6}$alkyl and the other is hydroxy or $C_{1-6}$alkoxy;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, ureido, N'—($C_{1-6}$alkyl)ureido, N—($C_{1-6}$alkyl)ureido, N',N'—($C_{1-6}$alkyl)$_2$ureido, N'—($C_{1-6}$alkyl)—N—($C_{1-6}$alkyl)ureido, N',N'—($C_{1-6}$alkyl)$_2$—N—($C_{1-6}$alkyl)ureido, N—($C_{1-6}$alkyl)sulphamoyl and N,N—($C_{1-6}$alkyl)$_2$sulphamoyl;

v is 0–5;

one of $R^4$ and $R^5$ is a group of formula (IA):

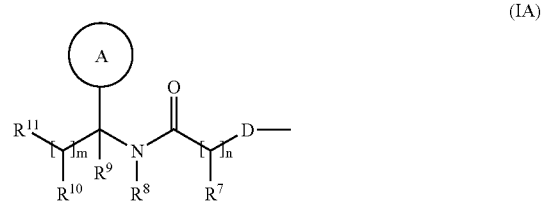

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^3$ and $R^6$ and the other of $R^4$ and $R^5$ may be optionally substituted on carbon by one or more $R^{16}$;

D is —O—, —N($R^a$)—, —S(O)$_b$— or —CH($R^a$)—; wherein $R^a$ is hydrogen or $C_6$alkyl and b is 0–2;

Ring A is aryl or heteroaryl; wherein Ring A is optionally substituted by one or more substituents selected from $R^{17}$;

$R^7$ is hydrogen, $C_{1-4}$alkyl, carbocyclyl or heterocyclyl; wherein $R^7$ is optionally substituted by one or more substituents selected from $R^{18}$;

$R^8$ is hydrogen or $C_{1-4}$alkyl;

$R^9$ is hydrogen or $C_{1-4}$alkyl;

$R^{10}$ is hydrogen, $C_{1-4}$alkyl, carbocyclyl or heterocyclyl; wherein $R^{10}$ is optionally substituted by one or more substituents selected from $R^{19}$;

$R^{11}$ is carboxy, sulpho, sulphino, phosphono, tetrazolyl, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$alkyl; or $R^{11}$ is a group of formula (IB):

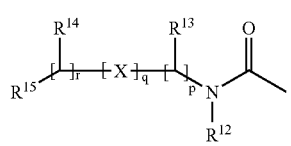

(IB)

wherein:

X is —N(R$^q$), —N(R$^q$)C(O)—, —O—, and —S(O)$_a$—; wherein a is 0–2 and R$^q$ is hydrogen or $C_{1-4}$alkyl;

$R^{12}$ is hydrogen or $C_{1-4}$alkyl;

$R^{13}$ and $R^{14}$ are independently selected from hydrogen, $C_{1-4}$alkyl, carbocyclyl, heterocyclyl or $R^{23}$; wherein said $C_{1-4}$alkyl, carbocyclyl or heterocyclyl may be independently optionally substituted by one or more substituents selected from $R^{20}$;

$R^{15}$ is carboxy, sulpho, sulphino, phosphono, tetrazolyl, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$alkyl; or $R^{15}$ is a group of formula (IC):

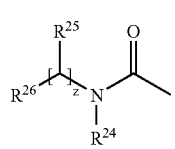

(IC)

wherein:

$R^{24}$ is selected from hydrogen or $C_{1-4}$alkyl;

$R^{25}$ is selected from hydrogen, $C_{1-4}$alkyl, carbocyclyl, heterocyclyl or $R^{27}$; wherein said $C_{1-4}$alkyl, carbocyclyl or heterocyclyl may be independently optionally substituted by one or more substituents selected from $R^{28}$;

$R^{26}$ is selected from carboxy, sulpho, sulphino, phosphono, tetrazolyl, —P(O)(OR$^g$)(OR$^h$), —P(O)(OH)(OR$^g$), —P(O)(OH)(R$^g$) or —P(O)(OR$^g$)(R$^h$) wherein R$^g$ and R$^h$ are independently selected from $C_{1-6}$alkyl;

p is 1–3; wherein the values of $R^{13}$ may be the same or different;

q is 0–1;

r is 0–3; wherein the values of $R^{14}$ may be the same or different;

m is 0–2; wherein the values of $R^{10}$ may be the same or different;

n is 1–3; wherein the values of $R^7$ may be the same or different;

z is 0–3; wherein the values of $R^{25}$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^{16}$, $R^{17}$ and $R^{18}$ may be independently optionally substituted on carbon by one or more $R^{21}$;

$R^{19}$, $R^{20}$, $R^{23}$, $R^{27}$ and $R^{28}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$alkyl; wherein $R^{19}$, $R^{20}$, $R^{23}$, $R^{27}$ and $R^{28}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

or a pharmaceutically acceptable salt, solvate, solvate of such a salt or a prodrug thereof.

According to a further aspect of the present invention there is provided a compound of formula (I'):

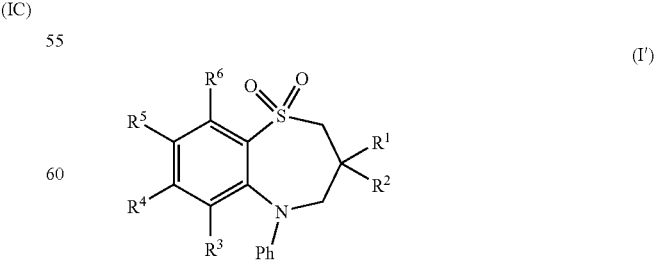

(I')

wherein:

$R^1$ and $R^2$ are independently selected from $C_{1-6}$alkyl;

one of R⁴ and R⁵ is a group of formula (IA'):

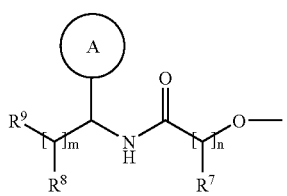

(IA')

R³ and R⁶ and the other of R⁴ and R⁵ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl) amino, N,N—($C_{1-4}$alkyl)₂ amino, $C_{1-4}$alkanoylamino, N—($C_{1-4}$alkyl)carbamoyl, N,N—($C_{1-4}$alkyl)₂carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)₂sulphamoyl; wherein R³ and R⁶ and the other of R⁴ and R⁵ may be optionally substituted on carbon by one or more $R^{12}$;

Ring A is aryl or heteroaryl; wherein Ring A is optionally substituted by one or more substituents selected from $R^{13}$;

R⁷ is hydrogen, $C_{1-4}$alkyl, carbocyclyl or heterocyclyl; wherein R⁷ is optionally substituted by one or more substituents selected from $R^{14}$;

R⁸ is hydrogen, $C_{1-4}$alkyl, carbocyclyl or heterocyclyl; wherein R⁸ is optionally substituted by one or more substituents selected from $R^{15}$;

R⁹ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$alkyl; or R⁹ is a group of formula (IB'):

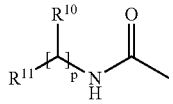

(IB')

wherein:

R¹⁰ is hydrogen, $C_{1-4}$alkyl, carbocyclyl or heterocyclyl; wherein R¹⁰ is optionally substituted by one or more substituents selected from $R^{16}$;

R¹¹ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$alkyl;

p is 1–3; wherein the values of R¹⁰ may be the same or different;

m is 0–2; wherein the values of R⁸ may be the same or different;

n is 1–3; wherein the values of R⁷ may be the same or different;

$R^{12}$, $R^{13}$ and $R^{14}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)₂amino, $C_{1-4}$alkanoylamino, N—($C_{1-4}$alkyl)carbamoyl, N,N—($C_{1-4}$alkyl)₂carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)₂sulphamoyl; wherein $R^{12}$, $R^{13}$ and $R^{14}$ may be independently optionally substituted on carbon by one or more $R^{17}$;

$R^{15}$ and $R^{16}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)₂amino, $C_{1-4}$alkanoylamino, N—($C_{1-4}$alkyl)carbamoyl, N,N—($C_{1-4}$alkyl)₂carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)₂sulpharmoyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$alkyl; wherein $R^{15}$ and $R^{16}$ may be independently optionally substituted on carbon by one or more $R^{18}$;

$R^{17}$ and $R^{18}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

or a pharmaceutically acceptable salt, solvate, solvate of such a salt or a prodrug thereof.

According to a further aspect of the present invention there is provided a compound of formula (I"):

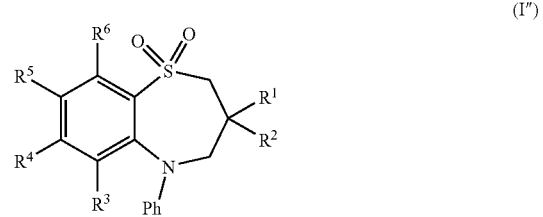

(I")

wherein:

R¹ and R² are independently selected from $C_{1-6}$alkyl;

one of R⁴ and R⁵ is a group of formula (IA"):

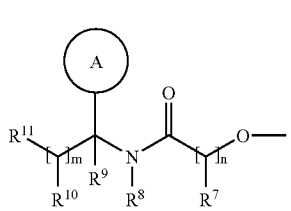

(IA")

R³ and R⁶ and the other of R⁴ and R⁵ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)₂amino, $C_{1-4}$alkanoylamino, N—($C_{1-4}$alkyl)carbamoyl, N,N—($C_{1-4}$alkyl)₂carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)₂sulphamoyl; wherein R³ and R⁶ and the other of R⁴ and R⁵ may be optionally substituted on carbon by one or more $R^{16}$;

Ring A is aryl or heteroaryl; wherein Ring A is optionally substituted by one or more substituents selected from $R^{17}$;

$R^7$ is hydrogen, $C_{1-4}$alkyl, carbocyclyl or heterocyclyl; wherein $R^7$ is optionally substituted by one or more substituents selected from $R^{18}$;

$R^8$ is hydrogen or $C_{1-4}$alkyl;

$R^9$ is hydrogen or $C_{1-4}$alkyl;

$R^{10}$ is hydrogen, $C_{1-4}$alkyl, carbocyclyl or heterocyclyl; wherein $R^{10}$ is optionally substituted by one or more substituents selected from $R^{19}$;

$R^{11}$ is carboxy, sulpho, sulphino, phosphono, —P(O)(OR$^c$)(OR$^d$), P(O)(OH)(OR$^c$), —P(O)(OH)(R$^d$) or —P(O)(OR$^c$)(R$^d$) wherein R$^c$ and R$^d$ are independently selected from $C_{1-6}$alkyl; or $R^{11}$ is a group of formula (IB″):

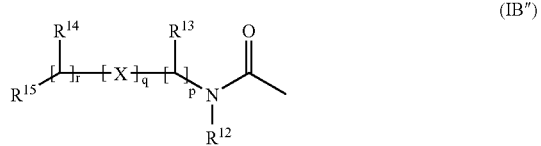

wherein:

X is —N(R$^q$)—, —N(R$^q$)C(O)—, —O—, and —S(O)$_a$—; wherein a is 0–2 and R$^q$ is hydrogen or $C_{1-4}$alkyl;

$R^{12}$ is hydrogen or $C_{1-4}$alkyl;

$R^{13}$ and $R^{14}$ are independently selected from hydrogen, $C_{1-4}$alkyl, carbocyclyl or heterocyclyl; wherein $R^{13}$ and $R^{14}$ may be independently optionally substituted by one or more substituents selected from $R^{20}$;

$R^{15}$ is carboxy, sulpho, sulphino, phosphono, —P(O)(OR$^f$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$alkyl;

p is 1–3; wherein the values of $R^{13}$ may be the same or different;

q is 0–1;

r is 0–3; wherein the values of $R^{14}$ may be the same or different;

m is 0–2; wherein the values of $R^{10}$ may be the same or different;

n is 1–3; wherein the values of $R^7$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^6$, $R^{17}$ and $R^{18}$ may be independently optionally substituted on carbon by one or more $R^{21}$;

$R^{19}$ and $R^{20}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$alkyl; wherein $R^{19}$ and $R^{20}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

or a pharmaceutically acceptable salt, solvate, solvate of such a salt or a prodrug thereof.

In the following paragraphs of the description, and in the claims, where a compound of formula (I) is referred to, it is to be understood that this aspect also relates to compounds of formula (I') and compounds of formula (I").

In addition, the skilled person will appreciate that the numbering system differs between compounds of formula (I) and compounds of formula (I'). The numbering system used hereinbelow refers to compounds of formula (I), but it is to be understood that these statements also apply to the corresponding values in formula (I').

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include phenyl$C_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

"Heteroaryl" is a totally unsaturated, mono or bicyclic ring containing 3–12 atoms of which at least one atom is chosen from nitrogen, sulphur or oxygen, which may, unless otherwise specified, be carbon or nitrogen linked. Preferably "heteroaryl" refers to a totally unsaturated, monocyclic ring containing 5 or 6 atoms or a bicyclic ring containing 9 or 10 atoms of which at least one atom is chosen from nitrogen, sulphur or oxygen, which may, unless otherwise specified, be carbon or nitrogen linked. In another aspect of the invention, "heteroaryl" refers to a totally unsaturated, monocyclic ring containing 5 or 6 atoms or a bicyclic ring containing 8, 9 or 10 atoms of which at least one atom is chosen from nitrogen, sulphur or oxygen, which may, unless otherwise specified, be carbon or nitrogen linked. Examples and suitable, values of the term "heteroaryl" are thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl and quinolyl. Preferably the term "heteroaryl" refers to thienyl or indolyl.

"Aryl" is a totally unsaturated, mono or bicyclic carbon ring that contains 3–12 atoms. Preferably "aryl" is a monocyclic ring containing 5 or 6 atoms or a bicyclic ring containing 9 or 10 atoms. Suitable values for "aryl" include phenyl or naphthyl. Particularly "aryl" is phenyl.

A "heterocyclyl" is a saturated, partially saturated or unsaturated, mono or bicyclic ring containing 3–12 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrinidyl, thiazolyl, pyrazinyl, pyridazinyl, pyridyl, 4-pyridonyl, quinolyl and 1-isoquinolonyl.

A "carbocyclyl" is a saturated, partially saturated or unsaturated, mono or bicyclic carbon ring that contains 3–12 atoms; wherein a —CH$_2$— group can optionally be replaced by a —C(O)—. Preferably "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclopropyl, cyclobutyl, 1-oxocyclopentyl, cyclopentyl, cyclopentenyl, cyclohexyl, cyclohexenyl, phenyl or 1-oxoindanyl.

An example of "$C_{1-6}$alkanoyloxy" and "$C_{1-4}$alkanoyloxy" is acetoxy. Examples of "$C_{1-6}$alkoxycarbonyl" and "$C_{1-4}$alkoxycarbonyl" include methoxycarbonyl, ethoxycarbonyl, n- and t-butoxycarbonyl. Examples of "$C_{1-6}$alkoxy" and "$C_{1-4}$alkoxy" include methoxy, ethoxy and propoxy. Examples of "$C_{1-6}$alkanoylamino" and "$C_{1-4}$alkanoylamino" include formamido, acetamido and propionylamino. Examples of "$C_{1-6}$alkylS(O)$_a$ wherein a is 0 to 2" and "$C_{1-4}$alkylS(O)$_a$ wherein a is 0 to 2" include methylthio, ethylthio, methylsulphinyl, ethylsulphinyl, mesyl and ethylsulphonyl. Examples of "$C_{1-6}$alkanoyl" and "$C_{1-4}$alanoyl" include $C_{1-3}$alkanoyl, propionyl and acetyl. Examples of "N—($C_{1-6}$alkyl)amino" and "N—($C_{1-4}$alkyl)amino" include methylamino and ethylamino. Examples of "N,N—($C_{1-6}$alkyl)$_2$amino" and "N,N—($C_{1-4}$alkyl)$_2$amino" include di-N-methylamino, di-(N-ethyl)amino and N-ethyl-N-methylamino. Examples of "$C_{2-6}$alkenyl" and "$C_{2-4}$alkenyl" are vinyl, allyl and 1-propenyl. Examples of "$C_{2-6}$alkynyl" and "$C_{2-4}$alkynyl" are ethynyl, 1-propynyl and 2-propynyl. Examples of "N—($C_{1-6}$alkyl)sulphamoyl" and "N—($C_{1-4}$alkyl)sulphamoyl" are N—($C_{1-3}$alkyl)sulphamoyl, N—(methyl)sulphamoyl and N—(ethyl)sulphamoyl. Examples of "N—($C_{1-6}$alkyl)$_2$sulphamoyl" and "N—($C_{1-4}$alkyl)$_2$sulphamoyl" are N,N—(dimethyl)sulphamoyl and N—(methyl)-N—(ethyl)sulphamoyl. Examples of "N—($C_{1-6}$alkyl)carbamoyl" and "N—($C_{1-4}$alkyl)carbamoyl" are methylaminocarbonyl and ethylaminocarbonyl. Examples of "N,N—($C_{1-6}$alkyl)$_2$carbamoyl" and "N,N—($C_{1-4}$alkyl)$_2$carbamoyl" are dimethylaminocarbonyl and methylethylaminocarbonyl. Examples of "$C_{1-6}$alkoxycarbonylamino" are ethoxycarbonylamino and t-butoxycarbonylamino. Examples of "N'-($C_{1-6}$alkyl)ureido" are N'-methylureido and N'-ethylureido. Examples of "N—($C_{1-6}$alkyl)ureido" are N-methylureido and N-ethylureido. Examples of "N',N'-($C_{1-6}$alkyl)$_2$ureido are N',N'-dimethylureido and N'-methyl-N'-ethylureido. Examples of "N'-($C_{1-6}$alkyl)-N—($C_{1-6}$alkyl) ureido are N'-methyl-N-methylureido and N'-propyl-N-methylureido. Examples of "N',N'-($C_{1-6}$alkyl)$_2$-N—($C_{1-6}$alkyl)ureido are N',N'-dimethyl-N-methylureido and N'-methyl-N'-ethyl-N-propylureido.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). Examples of pro-drugs include in vivo hydrolysable esters and in vivo hydrolysable amides of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxyC$_{1-6}$alkyl esters for example 1-cyclohexylcarbonyloxyethyl; 1,3-dioxolen-2-onylmethyl esters for example. 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an iii vivo hydrolysable amide of a compound of the formula (I) containing a carboxy group is, for example, a N—$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess IBAT inhibitory activity.

The invention relates to any and all tautomeric forms of the compounds of the formula (I) that possess IBAT inhibitory activity.

It is also to be understood that certain compounds of the formula (I) can exist in solvated as well as unsolvated forms such as, for example, hydrated forms. It is to be understood that the invention encompasses all such solvated forms which possess IBAT inhibitory activity.

Preferred values of $R^1$, $R^2$, $R^3$, $R^4$, $R^5$ and $R^6$ are as follows. Such values may be used where appropriate with any of the definitions, claims or embodiments defined hereinbefore or hereinafter.

Preferably $R^v$ and $R^w$ are both hydrogen.

Preferably $R^1$ and $R^2$ are independently selected from $C_{1-4}$alkyl.

More preferably $R^1$ and $R^2$ are independently selected from ethyl or butyl.

More preferably $R^1$ and $R^2$ are independently selected from ethyl, propyl or butyl.

In one aspect of the invention particularly $R^1$ and $R^2$ are both butyl.

In a further aspect of the invention particularly $R^1$ and $R^2$ are both propyl.

In another aspect of the invention particularly one of $R^1$ and $R^2$ is ethyl and the other is butyl.

Preferably $R^x$ and $R^y$ are independently selected from hydrogen or $C_{1-6}$alkyl.

More preferably $R^x$ and $R^y$ are both hydrogen.

Preferably $R^z$ is selected from halo, amino, $C_{1-6}$alkyl, $C_{1-6}$alkoxycarbonylamino or N'—($C_{1-6}$alkyl)ureido.

More preferably $R^z$ is selected from chloro, amino, t-butyl, t-butoxycarbonylamino or N'-(t-butyl)ureido.

Preferably v is 0 or 1.

In one aspect of the invention, more preferably v is 0.

In one aspect of the invention, more preferably v is 1.

In one aspect of the invention preferably $R^4$ is a group of formula (IA) (as depicted above).

In another aspect of the invention preferably $R^5$ is a group of formula (IA) (as depicted above).

Preferably $R^3$ and $R^6$ are hydrogen.

Preferably the other of $R^4$ and $R^5$ that is not the group of formula (IA) is selected from halo, $C_{1-4}$alkoxy or $C_{1-4}$alkylS(O)$_a$ wherein a is 0 to 2; wherein that $R^4$ or $R^5$ may be optionally substituted on carbon by one or more $R^{16}$; wherein $R^{16}$ is independently selected from hydroxy and N,N—($C_{1-4}$alkyl)$_2$amino.

More preferably the other of $R^4$ and $R^5$ that is not the group of formula (IA) is selected from bromo, methoxy, isopropoxy, methylthio, ethylthio, isopropylthio or mesyl; wherein that $R^4$ or $R^5$ may be optionally substituted on carbon by one or more $R^{16}$ wherein $R^{16}$ is independently selected from hydroxy and N,N-dimethylamino.

Particularly the other of $R^4$ and $R^5$ that is not the group of formula (IA) is selected from bromo, methoxy, isopropoxy, methylthio, ethylthio, isopropylthio, 2-hydroxyethylthio, 2-(N,N-dimethylamino)ethylthio or mesyl.

More particularly the other of $R^4$ and $R^5$ that is not the group of formula (IA) is methylthio.

Preferably the other of $R^4$ and $R^5$ that is not the group of formula (IA) is selected from hydrogen, halo, $C_{1-4}$alkoxy or $C_{1-4}$alkylS(O)$_a$ wherein a is 0 to 2; wherein that $R^4$ or $R^5$ may be optionally substituted on carbon by one or more $R^{16}$; wherein $R^{16}$ is independently selected from hydroxy, carboxy and N,N—($C_{1-4}$alkyl)$_2$amino.

More preferably the other of $R^4$ and $R^5$ that is not the group of formula (IA) is selected from hydrogen, bromo, methoxy, isopropoxy, methylthio, ethylthio, isopropylthio or mesyl; wherein that $R^4$ or $R^5$ may be optionally substituted on carbon by one or more $R^{16}$; wherein $R^{16}$ is independently selected from hydroxy, carboxy and N,N-dimethylamino.

Particularly the other of $R^4$ and $R^5$ that is not the group of formula (IA) is selected from hydrogen, bromo, methoxy, isopropoxy, methylthio, carboxymethylthio, ethylthio, isopropylthio, 2-hydroxyethylthio, 2-(N,N-dimethylamino)ethylthio or mesyl.

In another aspect of the invention, more preferably the other of $R^4$ and $R^5$ that is not the group of formula (IA) is selected from hydrogen, chloro, bromo, methoxy, isopropoxy, methylthio, ethylthio or isopropylthio; wherein that $R^4$ or $R^5$ may be optionally substituted on carbon by one or more $R^{16}$; wherein $R^{16}$ is independently selected from hydroxy, carboxy and N,N-dimethylamino.

In another aspect of the invention, particularly the other of $R^4$ and $R^5$ that is not the group of formula (IA) is selected from hydrogen, chloro, bromo, methoxy, isopropoxy, methylthio, carboxymethylthio, ethylthio, isopropylthio, 2-hydroxyethylthio or 2-(N,N-dimethylamino)ethylthio.

In another aspect of the invention, more particularly the other of $R^4$ and $R^5$ that is not the group of formula (IA) is bromo or chloro.

In another aspect of the invention; more particularly the other of $R^4$ and $R^5$ that is not the group of formula (IA) is methoxy.

In one aspect of the invention, preferably Ring A is aryl.

In another aspect of the invention, preferably Ring A is heteroaryl.

When Ring A is aryl, preferably Ring A is phenyl.

When Ring A is heteroaryl, preferably Ring A is thienyl or indolyl.

Preferably Ring A is aryl or heteroaryl; wherein Ring A is optionally substituted by one or more substituents selected from $R^{17}$; wherein $R^{17}$ is selected from halo, hydroxy or $C_{1-4}$alkyl; wherein $R^{17}$ may be optionally substituted on carbon by one or more $R^{21}$; wherein $R^{21}$ is selected from halo.

Preferably D is —O— or —S—.

In one aspect of the invention, more preferably D is —O—.

In one aspect of the invention, more preferably D is —S—.

More preferably Ring A is phenyl, thienyl or indolyl; wherein Ring A is optionally substituted by one or more substituents selected from halo, hydroxy or trifluoromethyl.

Particularly Ring A is selected from phenyl, 4-hydroxyphenyl, thien-2-yl, 4-trifluoromethylphenyl, 3-hydroxyphenyl, 2-fluorophenyl, 2,3-dihydroxyphenyl or indol-3-yl.

More particularly Ring A is phenyl.

In another aspect of the invention, preferably Ring A is aryl or heteroaryl; wherein Ring A is optionally substituted by one or more substituents selected from $R^{17}$; wherein $R^{17}$ is selected from halo, hydroxy, $C_{1-4}$alkyl or $C_{1-4}$alkoxy; wherein $R^{17}$ may be optionally substituted on carbon by one or more $R^{21}$; wherein $R^{21}$ is selected from halo.

In another aspect of the invention, more preferably Ring A is phenyl, thienyl or indolyl; wherein Ring A is optionally substituted by one or more substituents selected from halo, hydroxy, methoxy or trifluoromethyl.

In another aspect of the invention, particularly Ring A is selected from phenyl, 4-hydroxyphenyl, 4-methoxyphenyl, thien-2-yl, 4-trifluoromethylphenyl, 3-hydroxyphenyl, 2-fluorophenyl, 2,3-dihydroxyphenyl or indol-3-yl.

In a further aspect of the invention, particularly Ring A is selected from phenyl, 4-hydroxyphenyl, 4-methoxyphenyl, thien-2-yl, 4-trifluoromethylphenyl, 3-hydroxyphenyl, 2-fluorophenyl, 4-fluorophenyl, 2,3-dihydroxyphenyl or indol-3-yl.

Preferably $R^7$ is hydrogen, $C_{1-4}$alkyl or carbocyclyl.
More preferably $R^7$ is hydrogen, methyl or phenyl.
Particularly $R^7$ is hydrogen.
In one aspect of the invention, preferably $R^8$ is hydrogen.
In another aspect of the invention, preferably $R^8$ is $C_{1-4}$alkyl.
In another aspect of the invention, more preferably $R^8$ is hydrogen or methyl.
In one aspect of the invention, preferably $R^9$ is hydrogen.
In another aspect of the invention, preferably $R^9$ is $C_{1-4}$alkyl.
In another aspect of the invention, more preferably $R^9$ is hydrogen or methyl.
Preferably $R^{10}$ is hydrogen.
In one aspect of the invention, preferably $R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein $R^c$ and $R^d$ are independently selected from $C_{1-6}$alkyl.

In another aspect of the invention, preferably $R^{11}$ is a group of formula (IB) (as depicted above).
Preferably $R^{11}$ is carboxy, —P(O)(OH)(OR$^c$) or a group of formula (IB) (as depicted above).
More preferably $R^{11}$ is carboxy, —P(O)(OH)(OEt) or a group of formula (IB) (as depicted above).
In another aspect of the invention, preferably $R^{11}$ is carboxy, sulpho, —P(O)(OH)(OR$^c$) wherein $R^c$ is selected from $C_{1-4}$alkyl or a group of formula (IB) (as depicted above).

Preferably X is —NH— or —NHC(O)—.
More preferably X is —NHC(O)—.
In one aspect of the invention, preferably $R^{12}$ is hydrogen.
In another aspect of the invention, preferably $R^{12}$ is $C_{1-4}$alkyl.
In another aspect of the invention, more preferably $R^{12}$ is hydrogen or methyl.
Preferably $R^{13}$ is hydrogen, $C_{1-4}$alkyl or carbocyclyl; wherein $R^{13}$ is optionally substituted by one or more substituents selected from $R^{20}$; wherein
$R^{20}$ is hydroxy.
More preferably $R^{13}$ is hydrogen, methyl or phenyl; wherein $R^{13}$ is optionally substituted by one or more substituents selected from $R^{20}$; wherein
$R^{20}$ is hydroxy.
Particularly $R^{13}$ is hydrogen, hydroxymethyl or phenyl.
More particularly $R^{13}$ is hydrogen or hydroxymethyl.
In another aspect of the invention, preferably $R^{13}$ is hydrogen, $C_{1-4}$alkyl or carbocyclyl; wherein $R^{13}$ is optionally substituted by one or more substituents selected from $R^2$; wherein
$R^{20}$ is hydroxy, carboxy, carbocyclyl or amino; wherein $R^{20}$ may be optionally substituted on carbon by one or more $R^{22}$;
$R^{22}$ is hydroxy.
In another aspect of the invention, more preferably $R^{13}$ is hydrogen, methyl, ethyl, butyl or phenyl; wherein $R^{13}$ is optionally substituted by one or more substituents selected from $R^{20}$; wherein
$R^{20}$ is hydroxy, carboxy, phenyl or amino; wherein $R^{20}$ may be optionally substituted on carbon by one or more $R^{22}$;
$R^{22}$ is hydroxy.
In another aspect of the invention, particularly $R^{13}$ is hydrogen, hydroxymethyl, 4-aminobutyl, 2-carboxyethyl, 4-hydroxybenzyl or phenyl.

In a further aspect of the invention, preferably $R^{13}$ is hydrogen, $C_{1-4}$alkyl or carbocyclyl; wherein $R^{13}$ is optionally substituted by one or more substituents selected from $R^{20}$; wherein
$R^{20}$ is hydroxy, carboxy, carbocyclyl, heterocyclyl or amino; wherein $R^{20}$ may be optionally substituted on carbon by one or more $R^{22}$;
$R^{22}$ is hydroxy.
In a further aspect of the invention, more preferably $R^{13}$ is hydrogen, methyl, ethyl, butyl or phenyl; wherein $R^{13}$ is optionally substituted by one or more substituents selected from $R^{20}$; wherein
$R^{20}$ is hydroxy, carboxy, phenyl, imidazolyl or amino; wherein $R^{20}$ may be optionally substituted on carbon by one or more $R^{22}$;
$R^{22}$ is hydroxy.
In a further aspect of the invention, particularly $R^{13}$ is hydrogen, hydroxymethyl, 4-aminobutyl, 2-carboxyethyl, 4-hydroxybenzyl, imidazol-5-ylmethyl or phenyl.

In another further aspect of the invention, preferably $R^{13}$ is hydrogen, $C_{1-4}$alkyl, carbocyclyl or $R^{23}$; wherein $R^{13}$ is optionally substituted by one or more substituents selected from $R^{20}$; wherein
$R^{20}$ is hydroxy, $C_{1-4}$alkylS(O)$_a$ wherein a is 0, $C_{1-4}$alkoxy, amino, carbocyclyl, heterocyclyl or mercapto; wherein $R^{20}$ may be independently optionally substituted on carbon by one or more $R^{22}$;
$R^{22}$ is selected from hydroxy; and
$R^{23}$ is carboxy.
In another further aspect of the invention, more preferably $R^{13}$ is hydrogen, methyl, ethyl, butyl or phenyl or $R^{23}$; wherein $R^{13}$ is optionally substituted by one or more substituents selected from $R^{20}$; wherein
$R^{20}$ is hydroxy, methylthio, methoxy, amino, imidazolyl or mercapto; wherein $R^{20}$ may be independently optionally substituted on carbon by one or more $R^{22}$;
$R^{22}$ is selected from hydroxy; and
$R^{23}$ is carboxy.
In another further aspect of the invention, particularly $R^{13}$ is hydrogen, carboxy, hydroxymethyl, mercaptomethyl, methoxymethyl, methylthiomethyl, 2-methylthioethyl, 4-aminobutyl, 4-hydroxybenzyl, imidazol-5-ylmethyl or phenyl.

In an other aspect more particularly $R^{13}$ is methylthiomethyl, methylsulphinylmethyl or methylsulphonylmethyl.

Preferably $R^{14}$ is hydrogen.
In another aspect of the invention, preferably $R^{14}$ is selected from hydrogen, $C_{1-4}$alkyl or carbocyclyl; wherein said $C_{1-4}$alkyl or carbocyclyl may be optionally substituted by one or more substituents selected from $R^{20}$; and
$R^{20}$ is hydroxy.
In another aspect of the invention, more preferably $R^{14}$ is selected from hydrogen, methyl or phenyl; wherein said methyl or phenyl may be optionally substituted by one or more substituents selected from $R^{20}$; and
$R^{20}$ is hydroxy.
In another aspect of the invention, particularly $R^{14}$ is hydrogen, phenyl or hydroxymethyl.
Particularly $R^{15}$ is carboxy or sulpho.
In one aspect of the invention, more particularly $R^{15}$ is carboxy in another aspect of the invention, more particularly $R^{15}$ is sulpho.
Preferably $R^{15}$ is carboxy, sulpho, —P(O)(OR$^e$)(OR$^f$), —P(O)(OH)(OR$^e$), —P(O)(OH)(R$^e$) or —P(O)(OR$^e$)(R$^f$) wherein $R^e$ and $R^f$ are independently selected from $C_{1-4}$alkyl.
More preferably $R^{15}$ is carboxy, sulpho, —P(O)(OR$^e$)(OR$^f$), —P(O)(OH)(OR$^e$), —P(O)(OH)(R$^e$) or —P(O)(OR$^e$)(R$^f$) wherein $R^e$ and $R^f$ are independently selected from methyl or ethyl.

Preferably $R^{15}$ is carboxy, sulpho, —P(O)(OEt)(OEt), —P(O)(OH)(OEt), —P(O)(OH)(Me) or —P(O)(OEt)(Me).

Preferably $R^{15}$ is carboxy, sulpho, phosphono, —P(O)(OR$^e$)(OR$^f$), P(O)(OH)(OR$^e$), —P(O)(OH)(R$^e$) or —P(O)(OR$^e$)(R$^f$) wherein R$^e$ and R$^f$ are independently selected from $C_{1-4}$alkyl or $R^{15}$ is a group of formula (IC) (as depicted above).

More preferably $R^{15}$ is carboxy, sulpho, phosphono, —P(O)(OR$^e$)(OR$^f$), —P(O)(OH)(OR$^e$), P(O)(OH)(R$^e$) or —P(O)(OR$^e$)(R$^f$) wherein R$^e$ and R$^f$ are independently selected from methyl or ethyl or $R^{15}$ is a group of formula (IC) (as depicted above).

Preferably $R^{15}$ is carboxy, sulpho, phosphono, —P(O)(OEt)(OEt), —P(O)(Ot-Bu)(Ot-Bu), —P(O)(OH)(OEt), —P(O)(OH)(Me) or —P(O)(OEt)(Me) or $R^{15}$ is a group of formula (IC) (as depicted above).

In one aspect of the invention, preferably $R^{15}$ is a group of formula (IC) (as depicted above).

In another aspect of the invention, preferably $R^{15}$ is not a group of formula (IC) (as depicted above).

In one aspect of the invention, preferably $R^{15}$ is carboxy.

In another aspect of the invention, preferably $R^{15}$ is sulpho.

In another aspect of the invention, preferably $R^{15}$ is —P(O)(OH)(OEt).

In another aspect of the invention, preferably $R^{15}$ is —P(O)(OH)(Me).

In another aspect of the invention, preferably $R^{15}$ is —P(O)(OEt)(Me).

In one aspect of the invention, preferably $R^{24}$ is hydrogen.

In another aspect of the invention, preferably $R^{24}$ is $C_{1-4}$alkyl.

Preferably $R^{25}$ is hydrogen.

Preferably $R^{26}$ is carboxy.

Preferably p is 1 or 2; wherein the values of $R^{13}$ may be the same or different.

In one aspect of the invention, more preferably p is 1.

In another aspect of the invention, more preferably p is 2; wherein the values of $R^{13}$ may be the same or different.

In a further aspect of the invention, more preferably p is 3; wherein the values of $R^{13}$ may be the same or different.

In one aspect of the invention, preferably q is 0.

In a further aspect of the invention, preferably q is 1.

In one aspect of the invention, preferably r is 0.

In one aspect of the invention, more preferably r is 1.

In another aspect of the invention, more preferably r is 2; wherein the values of $R^{14}$ may be the same or different.

In a further aspect of the invention, more preferably r is 3; wherein the values of $R^{14}$ may be the same or different.

Preferably m is 0.

In another aspect of the invention, preferably m is 0 or 1.

Preferably n is 1.

In another aspect of the invention, preferably n is 1 or 2.

Preferably z is 1.

The group of formula (IA') wherein $R^7$ is hydrogen, methyl or phenyl, n is 1, Ring A is phenyl, thienyl or indolyl; wherein Ring A is optionally substituted by one or more substituents selected from halo, hydroxy or trifluoromethyl, m is 0 and $R^9$ is carboxy, —P(O)(OH)(OR$^c$) or a group of formula (IB).

The group of formula (IA) wherein:
D is —O— or —S—;
Ring A is phenyl, thienyl or indolyl; wherein Ring A is optionally substituted by one or more substituents selected from halo, hydroxy, methoxy or trifluoromethyl;
$R^7$ is hydrogen, methyl or phenyl;
$R^8$ is hydrogen or methyl;
$R^9$ is hydrogen or methyl;
$R^{10}$ is hydrogen;
m is 0–2 wherein the values of $R^{10}$ may be the same or different; and
$R^{11}$ is carboxy, —P(O)(O)(OEt) or a group of formula (IB) (as depicted in claim 1);

The group of formula (IB') wherein $R^{10}$ is hydrogen, hydroxymethyl or phenyl, p is 1 or 2; wherein the values of $R^{10}$ may be the same or different and $R^{11}$ is carboxy or sulpho.

The group of formula (IB) wherein:
$R^{12}$ is hydrogen or methyl;
$R^{13}$ is hydrogen, methyl, ethyl, butyl or phenyl or $R^{23}$; wherein $R^{13}$ is optionally substituted by one or more substituents selected from $R^{20}$; $R^{20}$ is hydroxy, methylthio, methoxy, amino, imidazolyl or mercapto; wherein $R^{20}$ may be independently optionally substituted on carbon by one or more hydroxy; $R^{23}$ is carboxy;
X is —NH— or —NHC(O)—;
$R^{14}$ is selected from hydrogen, methyl or phenyl; wherein said methyl or phenyl may be optionally substituted by one or more substituents selected from hydroxy;
$R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from methyl or ethyl or $R^{15}$ is a group of formula (IC) (as depicted in claim 1);
p is 1–3 wherein the values of $R^{13}$ may be the same or different;
q is 0–1; and
r is 0–3 wherein the values of $R^{14}$ may be the same or different;

The group of formula (IC) wherein
$R^{24}$ is hydrogen;
$R^{25}$ is hydrogen;
$R^{26}$ is carboxy; and
z is 1;
or a pharmaceutically acceptable salt, solvate, solvate of such a salt or a prodrug thereof.

Therefore in a further aspect of the invention, there is provided a compound of formula (I') as depicted above wherein:
$R^1$ and $R^2$ are independently selected from ethyl or butyl;
$R^3$ and $R^6$ are hydrogen;
$R^4$ is selected from halo, $C_{1-4}$alkoxy or $C_{1-4}$alkylS(O)$_a$ wherein a is 0 to 2; wherein that $R^4$ may be optionally substituted on carbon by one or more $R^{16}$; wherein $R^{16}$ is independently selected from hydroxy and N,N—($C_{1-4}$ alkyl)$_2$amino;
$R^5$ is a group of formula (IA');
Ring A is aryl or heteroaryl; wherein Ring A is optionally substituted by one or more substituents selected from $R^7$; wherein
$R^{17}$ is selected from halo, hydroxy or $C_{1-4}$alkyl; wherein $R^{17}$ may be optionally substituted on carbon by one or more $R^{21}$; wherein
$R^{21}$ is selected from halo;
$R^7$ is hydrogen, $C_{1-4}$alkyl or carbocyclyl;
$R^{11}$ is carboxy, —P(O)(OH)(OR$^c$) or a group of formula (IB') (as depicted above);
$R^{13}$ is hydrogen, $C_{1-4}$alkyl or carbocyclyl; wherein $R^{13}$ is optionally substituted by one or more substituents selected from $R^{21}$; wherein
$R^{20}$ is hydroxy;
$R^{15}$ is carboxy or sulpho;
p is 1 or 2; wherein the values of $R^{13}$ may be the same or different;
m is 0; and
n is 1;

or a pharmaceutically acceptable salt, solvate, solvate of such a salt or a prodrug thereof.

Therefore in an additional aspect of the invention, there is provided a compound of formula (I') as depicted above wherein:

$R^1$ and $R^2$ are both butyl or one of $R^1$ and $R^2$ is ethyl and the other is butyl;
$R^4$ is methylthio;
$R^5$ is a group of formula (IA') (as depicted above);
$R^3$ and $R^6$ are hydrogen;
Ring A is phenyl;
$R^7$ is hydrogen;
$R^{11}$ is a group of formula (IB') (as depicted above);
$R^{13}$ is hydrogen or hydroxymethyl;
$R^{15}$ is carboxy or sulpho;
p is 1 or 2; wherein the values of $R^{13}$ may be the same or different;
m is 0;
n is 1;

or a pharmaceutically acceptable salt, solvate, solvate of such a salt or a prodrug thereof.

Therefore in an additional further aspect of the invention, there is provided a compound of formula (I'') as depicted above wherein:

$R^1$ and $R^2$ are independently selected from ethyl or butyl;
$R^3$ and $R^6$ are hydrogen;
$R^4$ is selected from halo, $C_{1-4}$alkoxy or $C_{1-4}$alkylS(O)$_a$ wherein a is 0 to 2; wherein that $R^4$ may be optionally substituted on carbon by one or more $R^{16}$; wherein $R^{16}$ is independently selected from hydroxy and N,N—(C$_{1-4}$alkyl)$_2$amino;
$R^5$ is a group of formula (IA'');
Ring A is aryl or heteroaryl; wherein Ring A is optionally substituted by one or more substituents selected from $R^{17}$;
$R^7$ is hydrogen, $C_{1-4}$alkyl or carbocyclyl;
$R^8$ is hydrogen or methyl;
$R^9$ is hydrogen or methyl;
$R^{11}$ is carboxy, —P(O)(OH)(OR$^c$) or a group of formula (IB'') (as depicted above);
X is —NH— or —NHC(O)—;
$R^{12}$ is hydrogen or methyl;
$R^{13}$ is hydrogen, $C_{1-4}$alkyl or carbocyclyl; wherein $R^{13}$ is optionally substituted by one or more substituents selected from $R^{20}$;
$R^{14}$ is hydrogen;
$R^{15}$ is carboxy or sulpho;
$R^{17}$ is selected from halo, hydroxy, $C_{1-4}$alkyl or $C_{1-4}$alkoxy; wherein $R^{17}$ may be optionally substituted on carbon by one or more $R^{21}$;
$R^{20}$ is hydroxy, carboxy, carbocyclyl or amino; wherein $R^{20}$ may be optionally substituted on carbon by one or more $R^{22}$;
$R^{21}$ is selected from halo;
$R^{22}$ is hydroxy;
p is 1–3; wherein the values of $R^{13}$ may be the same or different.
q is 0–1;
r is 0–3; wherein the values of $R^{14}$ may be the same or different; and wherein if q is 1, r is not 0;
m is 0–2; and
n is 1–3;

or a pharmaceutically acceptable salt, solvate, solvate of such a salt or a prodrug thereof.

Therefore in another additional further aspect of the invention, there is provided a compound of formula (I) as depicted above wherein:

$R^v$ and $R^w$ are both hydrogen;
$R^1$ and $R^2$ are independently selected from $C_{1-4}$alkyl;
$R^x$ and $R^y$ are both hydrogen;
$R^z$ is selected from halo, amino, $C_{1-6}$alkyl, $C_{1-6}$alkoxycarbonylamino or N'—(C$_{1-6}$alkyl)ureido;
v is 0 or 1;
$R^3$ and $R^6$ are hydrogen;
one of $R^4$ and $R^5$ is a group of formula (IA) (as depicted above) and the other is selected from hydrogen, halo, $C_{1-4}$alkoxy or $C_{1-4}$alkylS(O)$_a$ wherein a is 0 to 2; wherein that $R^4$ or $R^5$ may be optionally substituted on carbon by one or more $R^{16}$; wherein $R^{16}$ is independently selected from hydroxy, carboxy and N,N—(C$_{1-4}$alkyl)$_2$amino;
D is —O— or —S—;
$R^7$ is hydrogen, methyl or phenyl;
$R^8$ is hydrogen or methyl;
Ring A is aryl or heteroaryl; wherein Ring A is optionally substituted by one or more substituents selected from $R^{17}$; wherein $R^{17}$ is selected from halo, hydroxy, $C_{1-4}$alkyl or $C_{1-4}$alkoxy; wherein $R^{17}$ may be optionally substituted on carbon by one or more $R^{21}$; wherein $R^{21}$ is selected from halo;
$R^9$ is hydrogen or methyl;
$R^{10}$ is hydrogen;
$R^{11}$ is carboxy, —P(O)(OH)(OR$^c$) wherein R$^c$ is selected from $C_{1-4}$alkyl or a group of formula (IB) (as depicted above);
$R^{12}$ is hydrogen or methyl;
X is —NH— or —NHC(O)—;
$R^{13}$ is hydrogen, $C_{1-4}$alkyl, carbocyclyl or $R^{23}$; wherein $R^{13}$ is optionally substituted by one or more substituents selected from $R^{20}$; wherein $R^{20}$ is hydroxy, $C_{1-4}$alkylS(O)$_a$ wherein a is 0, $C_{1-4}$alkoxy, amino, carbocyclyl, heterocyclyl or mercapto; wherein $R^{20}$ may be independently optionally substituted on carbon by one or more $R^{22}$; $R^{22}$ is selected from hydroxy; and $R^{23}$ is carboxy;
$R^{14}$ is selected from hydrogen, $C_{1-4}$alkyl or carbocyclyl; wherein said $C_{1-4}$alkyl or carbocyclyl may be optionally substituted by one or more substituents selected from $R^{20}$; and $R^{20}$ is hydroxy;
$R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_1$alkyl or $R^{15}$ is a group of formula (IC) (as depicted above);
$R^{24}$ is hydrogen;
$R^{25}$ is hydrogen;
$R^{26}$ is carboxy;
p is 1–3; wherein the values of $R^{13}$ may be the same or different;
q is 0–1;
r is 0–3; wherein the values of $R^{14}$ may be the same or different;
m is 0–2; wherein the values of $R^{10}$ may be the same or different;
n is 1–2; wherein the values of $R^7$ may be the same or different;
z is 0–1; wherein the values of $R^{25}$ may be the same or different;

or a pharmaceutically acceptable salt, solvate, solvate of such a salt or a prodrug thereof.

In another aspect of the invention, preferred compounds of the invention are any one of the Examples or a pharmaceutically acceptable salt, solvate, solvate of such a salt or a prodrug thereof.

In one aspect of the invention, there is provided a compound of formula (I) selected from Examples 8, 9, 46, 56, 59, 60, 61, 62, 66 and 69 or a pharmaceutically acceptable salt, solvate, solvate of such a salt or a prodrug thereof.

In another aspect of the invention, there is provided a compound of formula (I) which is Example 73, 74, 95, 96, 97, 98, 99 and 100 or a pharmaceutically acceptable salt, solvate, solvate of such a salt or a prodrug thereof.

In another aspect of the invention, preferred compounds of the invention are any one of Examples 43, 50, 51 and 52 or a pharmaceutically acceptable salt, solvate, solvate of such a salt or a prodrug thereof.

In another additional aspect of the invention, preferred compounds of the invention are any one of Examples 43, 46, 50, 51, 56, 58, 59, 61, 62, 63, 69, 81, 83, 85, 94, 97, 98, 108, 109, 110, 111 or 117.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1): oxidising a benzothiazepine of formula (II):

(II)

Process 2): for compounds of formula (I) wherein D is —O—, —NR$^a$ or —S—; reacting a compound of formula (IIIa) or (IIIb):

(IIIa)

(IIIb)

with a compound of formula (IV):

(IV)

wherein L is a displaceable group;

Process 3): reacting an acid of formula (Va) or (Vb):

(Va)

(Vb)

or an activated derivative thereof; with an amine of formula (VI):

(VI)

Process 4): for compounds of formula (I) wherein $R^{11}$ is a group of formula (IB); reacting a compound of formula (I) wherein $R^{11}$ is carboxy with an amine of formula (VII):

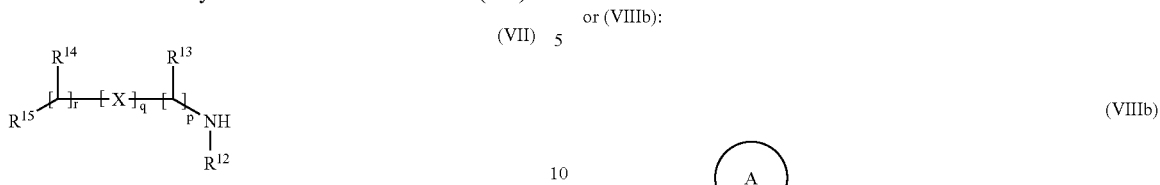
(VII)

Process 5): for compounds of formula (I) wherein $R^{11}$ is carboxy; deprotecting a compound of formula (VIIIa):

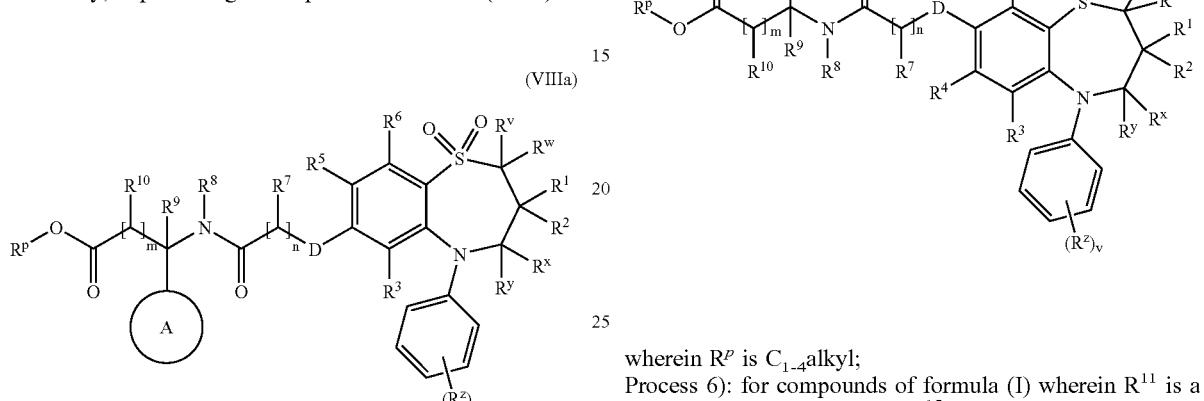
(VIIIa)

or (VIIIb):

(VIIIb)

wherein $R^p$ is $C_{1-4}$alkyl;

Process 6): for compounds of formula (I) wherein $R^{11}$ is a group of formula (IB) and $R^{15}$ is carboxy; deprotecting a compound of formula (IXa):

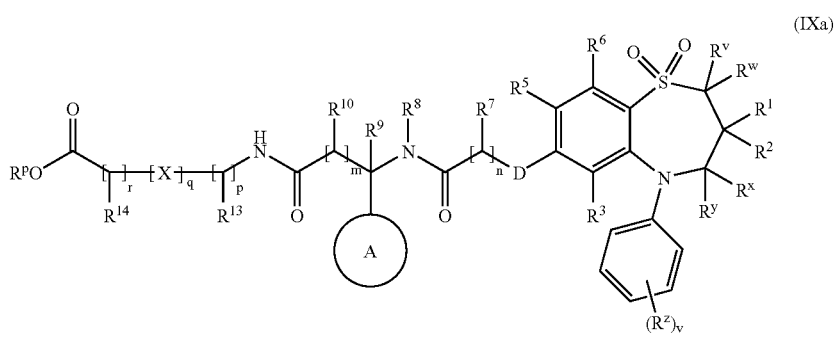
(IXa)

or (IXb):

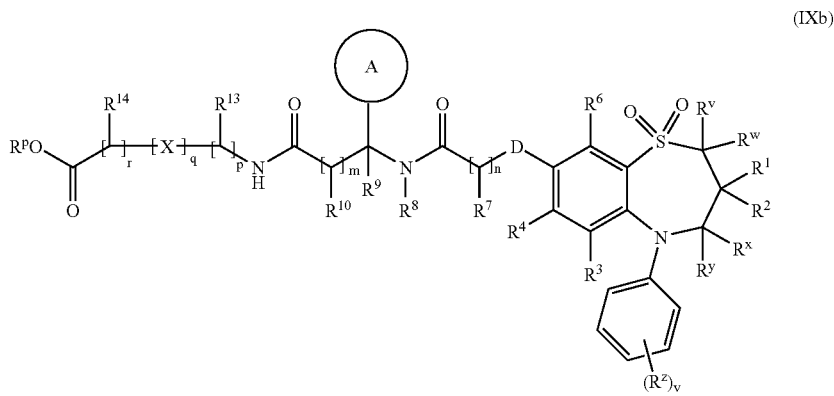
(IXb)

wherein $R^p$ is $C_{1-4}$alkyl;

Process 7) for compounds of formula (I) wherein one of $R^4$ and $R^5$ are independently selected from $C_{1-4}$alkylthio optionally substituted on carbon by one or more $R^{16}$; reacting a compound of formula (Xa) or (Xb):

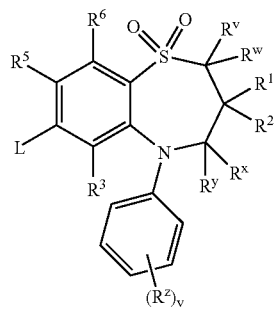
(Xa)

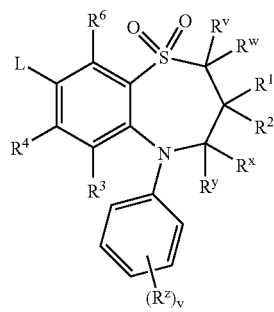
(Xb)

wherein L is a displaceable group; with a thiol of formula (XI):

(XI)

wherein $R^y$ is $C_{1-4}$alkylthio optionally substituted on carbon by one or more $R^{16}$;

Process 8) for compounds of formula (I) wherein $R^{15}$ is a group of formula (IC) reacting a compound of formula (IXa) or (IXb) wherein $R^p$ is hydrogen with a compound of formula (XII):

(XII)

Process 9): for compounds of formula (I) wherein $R^{11}$ is a group of formula (IB) and $R^{15}$ is a group of formula (IC) and $R^{26}$ is carboxy; deprotecting a compound of formula (XIIIa):

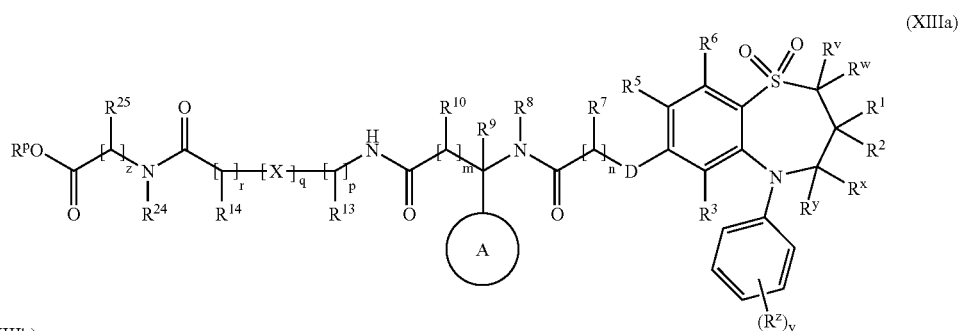
(XIIIa)

or (XIIIb):

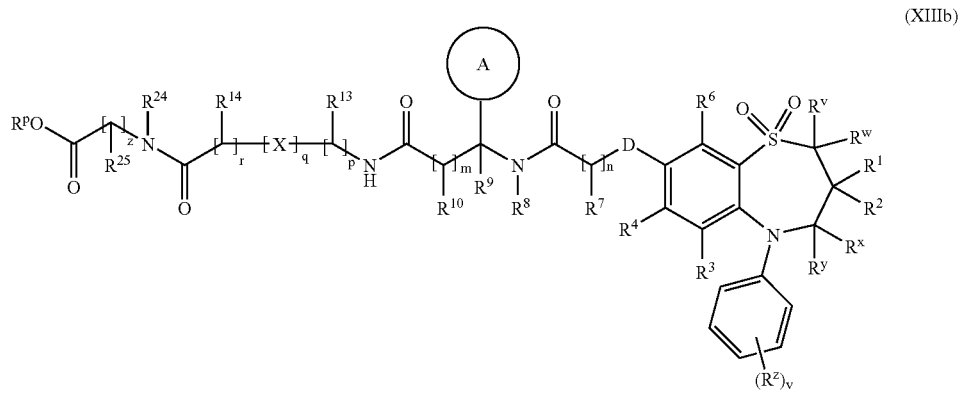
(XIIIb)

and $R^p$ is $C_{1-4}$alkyl;

Process 10): for compounds of formula (I) wherein X is —N(R$^q$)C(O)—; reacting a compound of formula (XIVa):

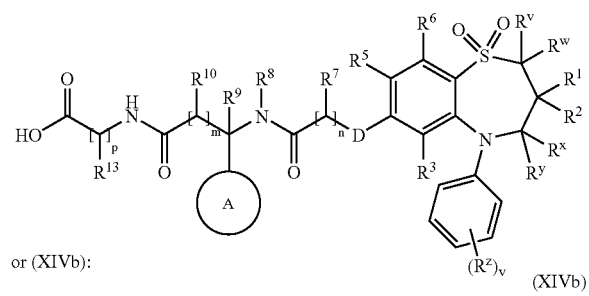
(XIVa)

or (XIVb):

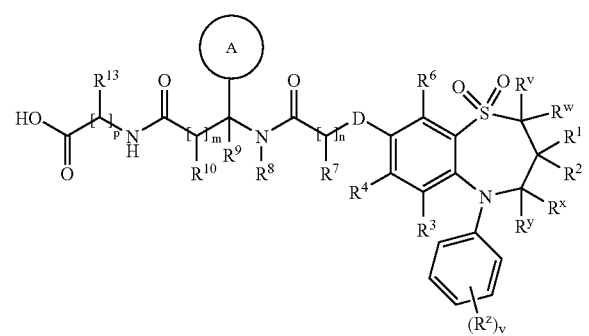
(XIVb)

with a compound of formula (XV):

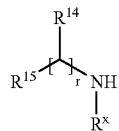
(XV)

and thereafter if necessary or desirable:
i) converting a compound of the formula (I) into another compound of the formula (I);
ii) removing any protecting groups;
iii) forming a pharmaceutically acceptable salt, solvate, solvate of such a salt or a prodrug.

The skilled person will also appreciate that similar processes corresponding to the above processes can also be used to prepare compounds of formula (I') and compounds of formula (I") wherein the definitions of the variable groups may differ.

L is a displaceable group, suitable values for L are for Example, a halogeno or sulphonyloxy group, for Example a chloro, bromo, methanesulphonyloxy or toluene-4-sulphonyloxy group.

$R^p$ is $C_{1-4}$alkyl. Preferably $R^p$ is methyl or ethyl. More preferably $R^p$ is methyl.

Specific reaction conditions for the above reactions are as follows.

Process 1): Benzothiazepines of formula (II) may be oxidised under standard sulphur oxidation conditions; for Example using hydrogen peroxide and trifluoroacetic acid at a temperature in the range of 0° C. to reflux, preferably at or near room temperature.

Compounds of formula (II) may be prepared according to Scheme I for compounds of formula (I) wherein $R^x$ and $R^y$ are hydrogen. The skilled man will appreciate that where $R^x$ and $R^y$ are not both hydrogen the following synthetic route needs to be manipulated using procedures known to the skilled person.

Scheme 1

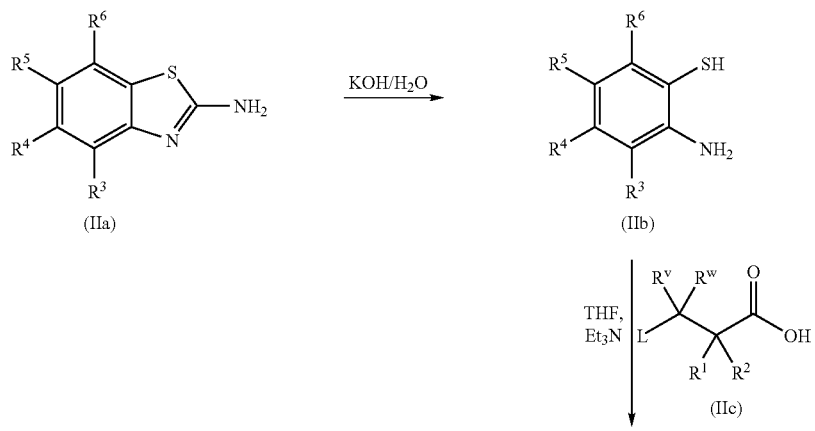

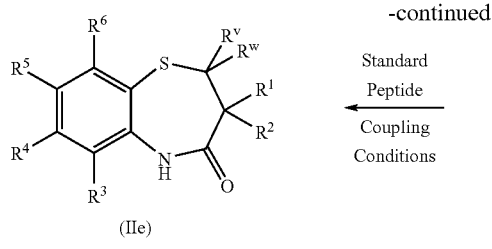

(IIe)

-continued

Standard Peptide Coupling Conditions
→

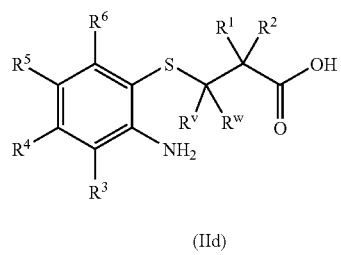

(IId)

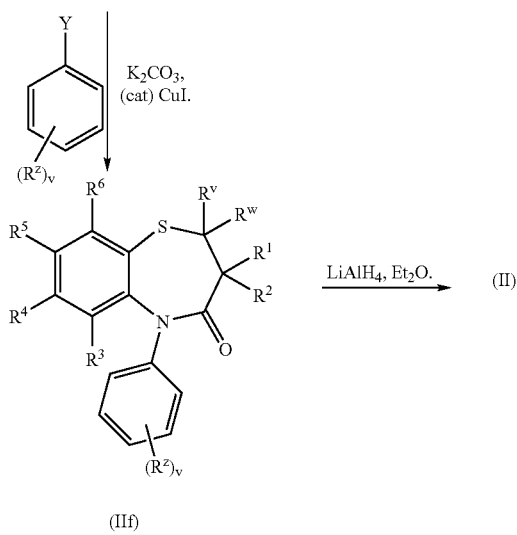

(IIf)

wherein L is a displaceable group as defined above, and Y is a displaceable group, for Example halo.

Compounds of formula (IIa) and (IIc) are commercially available compounds, or they are known in the literature, or they are prepared by standard processes known in the art.

Process 2): Alcohols of formula (IIIa) or (IIIb) may be reacted with compounds of formula (IV) in the presence of a base for Example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (IIIa) or (IIIb) may be prepared in a similar manner to compounds of formula (II) (but wherein $R^4$ or $R^5$ is hydroxy) followed by the oxidation step of Process 1).

Compounds of formula (IV) are commercially available compounds, or they are known in the literature, or they are prepared by standard processes known in the art.

Process 3), Process 4, Process 8) and Process 10): Acids and amines may be coupled together in the presence of a suitable coupling reagent. Standard peptide coupling reagents known in the art can be employed as suitable coupling reagents, or for Example carbonyldiimidazole and dicyclohexyl-carbodiimide, optionally in the presence of a catalyst such as dimethylaminopyridine or 4-pyrrolidinopyridine, optionally in the presence of a base for Example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for Example acid chlorides, and active esters, for Example pentafluorophenyl esters. The reaction of these types of compounds with amines is well known in the art, for Example they may be reacted in the presence of a base, such as those described above, and in a suitable solvent, such as those described above. The reaction may conveniently be performed at a temperature in the range of −40 to 40° C.

Compounds of formula (Va) or (Vb) wherein D is —O—, —NR$^a$— or —S— may be prepared according to Scheme 2:

Scheme 2

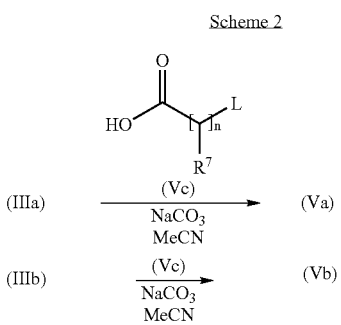

wherein L is a displaceable group as defined above.

Compounds of formula (Va) and (Vb) where D is —SO— or —SO$_2$— may be prepared by oxidising the resulting compounds of formula (Va) and (Vb) from Scheme 2 where D is —S—.

Compounds of formula (Va) or (Vb) wherein D is —CH$_2$— may be prepared according to Scheme 3.

Scheme 3

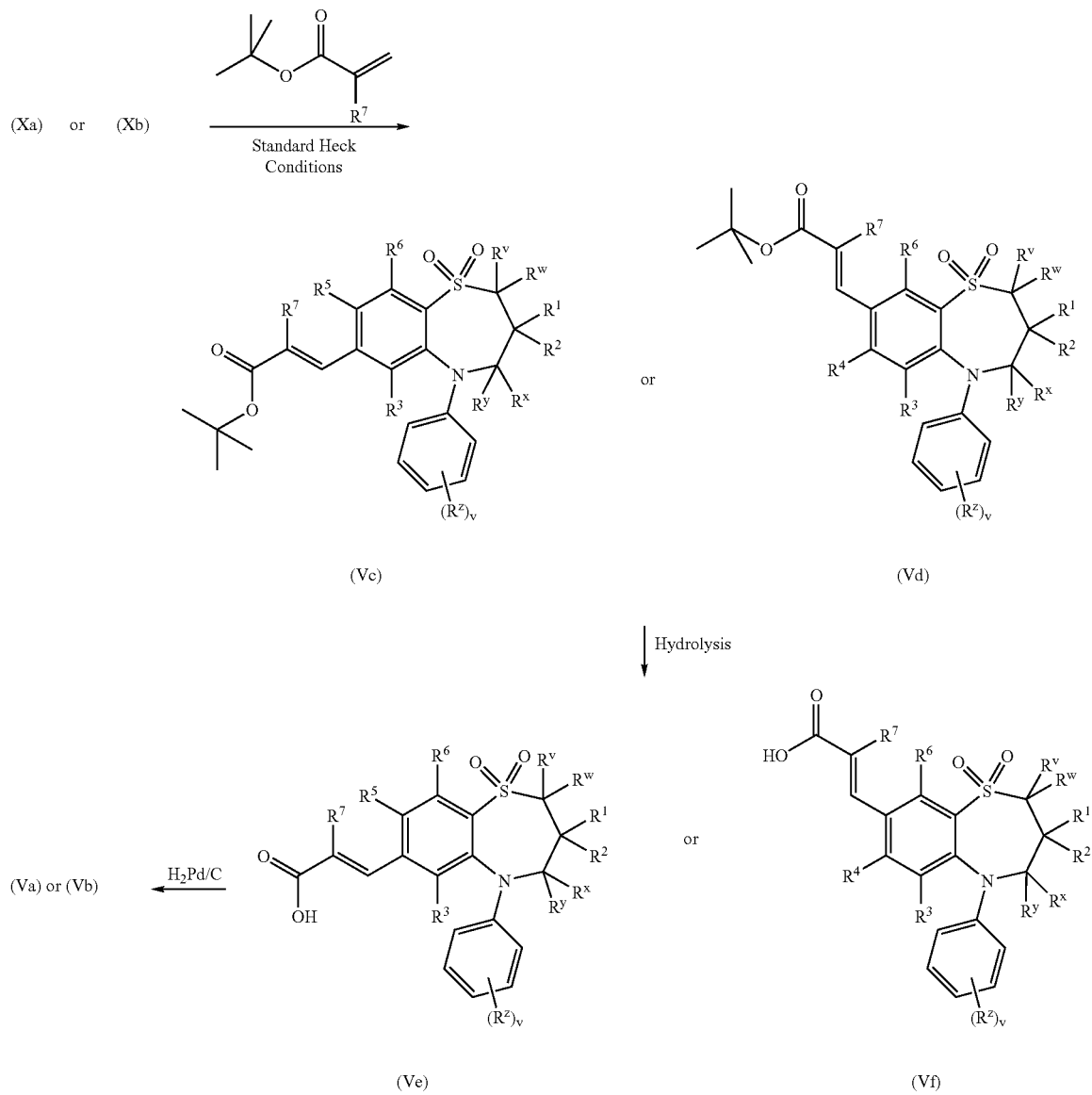

Compounds of formula (XIVa) or (XIVa) may be prepared by any of the processes described herein where $R^{11}$ is a group of formula (IB) but wherein (IB) is a group of formula (XVI):

(XVI)

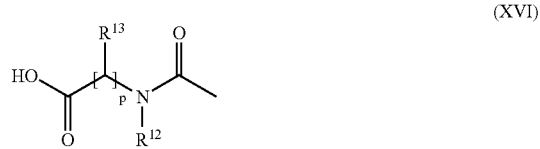

Compounds of formula (Vc), (VI), (VII), (XII), (XV) and (XVI) are commercially available compounds, or they are known in the literature, or they are prepared by standard processes known in the art.

Process 5), Process 6) and Process 9): Esters of formula (VIIIa), (VIIIb), (IXa), (IXb) (XIIIa) and (XIIIb) may be deprotected under standard conditions such as those described below, for Example they may be deprotected with sodium hydroxide in methanol at room temperature.

Esters of formula (VIIIa), (VIIIb), (IXa), (IXb) (XIIIa) and (XIIIb) may be prepared by any of the procedures above for the preparation of compounds of formula (I), but wherein $R^{11}$, $R^{15}$ or $R^{26}$ is $C_{1-4}$alkoxycarbonyl.

Process 7): Compounds of formula (Xa) and (Xb) may be reacted with thiols of formula (XI) in the presence of base, for Example an inorganic base such as sodium carbonate or an organic base such as Hunigs base, in the presence of a suitable solvent such as DMF or THF at a temperature in the range of 0° C. to reflux.

Compounds of formula (Xa) and (Xb) may be prepared by any of the procedures above for the preparation of compounds of formula (I), but wherein one of $R^4$ and $R^5$ is L.

Compounds of formula (XI) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess IBAT inhibitory activity. These properties may be assessed, for example, using an in vitro test assay for studying the effect on bile acid uptake in IBAT-transfected cells (Smith L., Price-Jones M. J., Hugnes K. T. and Jones N. R. A.; J Biomolecular Screening, 3, 227–230) or in vivo by studying the effect on radiolabelled bile acid absorption in mice/rats (Lewis M. C., Brieaddy L. E. and Root C., J., J Lip Res 1995, 36, 1098–1105).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range 5–5000 mg per square meter body area of the animal, i.e. approximately 0.1–100 mg/kg or 0.01–50 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. In another aspect a daily dose in the rage of 0.02–20 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective IBAT inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocyte, monocytes and/or macrophage infiltrate, intimital thickening, medial thinning, infectious and surgical trauma and vascular thrombosis, stroke and transient ischaemic attacks in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of atherosclerosis, coronary heart diseases, myocardial infarction, angina pectoris, peripheral vascular diseases, stroke and transient ischaemic attacks in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocyte, monocytes and/or macrophage infiltrate, intimital thickening, medial thinning, infectious and surgical trauma and vascular thrombosis, stroke and transient ischaemic attacks in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating atherosclerosis, coronary heart diseases, myocardial infarction, angina pectoris, peripheral vascular diseases, stroke and transient ischaemic attacks in a warm-blooded animal, such as man, in need of such treatment which comprises administering to said animal an effective amount of a compound of formula (I), or a pharmaceutically acceptable salt, solvate, solvate of such a salt or a prodrug thereof.

There is evidence that an IBAT inhibitor might potentially be useful in the treatment and/or prevention of gallstones. According to a further feature of this aspect of the invention there is provided a method of treating and/or preventing gallstones in a warm-blooded animal, such as man, in need of such treatment which comprises administering to said animal an effective amount of a compound of formula (I), or a pharmaceutically acceptable salt, solvate, solvate of such a salt or a prodrug thereof.

The size of the dose required for the therapeutic or prophylactic treatment will necessarily be varied depending on the host treated, the route of administration and the severity of the illness being treated. A unit dose in the range, for example, 1–100 mg/kg, preferably 1–50 mg/kg is envisaged.

The IBAT inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional IBAT inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and (E)-7-[4-(4-fluorophenyl)-6-isopropyl-2-[methyl(methylsulphonyl)amino]pyrimidin-5-yl](3R,5S)-3,5-dihydroxyhept-6-enoic acid (rosuvastatin), or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is (E)-7-[4-(4-fluorophenyl)-6-isopropyl-2-[methyl(methylsulphonyl)amino]pyrimidin-5-yl](3R,5S)-3,5-dihydroxyhept-6-enoic acid (rosuvastatin), or a pharmaceutically acceptable salt, solvate, solvate of such a salt or a prodrug thereof. A preferable particular statin is rosuvastatin calcium salt.

In an additional aspect of the invention, the compound of formula (I), or a pharmaceutically acceptable salt, solvate, solvate of such a salt or a prodrug thereof may be administered in association with an HMG Co-A reductase inhibitor, or a pharmaceutically acceptable salt, solvate, solvate of such a salt or a prodrug thereof, and/or a bile acid binder thereby avoiding a possible risk of excess of bile acids in colon caused by the inhibition of the ileal bile acid transport system. An excess of bile acids in the visceral contents may cause diarrhoea. Thus, the present invention also provides a treatment of a possible side effect such as diarrhoea in patients during therapy comprising the compound of formula (I), or a pharmaceutically acceptable salt, solvate, solvate of such a salt or a prodrug thereof.

An HMG CoA-reductase inhibitor, or a pharmaceutically acceptable salt, solvate, solvate of such a salt or a prodrug thereof will by its action decrease the endogenous cholesterol available for the bile acid synthesis and have an additive effect in combination with the compound of formula (I), or a pharmaceutically acceptable salt, solvate, solvate of such a salt or a prodrug thereof on lipid lowering.

Suitable bile acid binders for such a combination therapy are resins, such as cholestyramine and cholestipol. One advantage is that the dose of bile acid binder might be kept lower than the therapeutic dose for treatment of cholesterolaemia in single treatment comprising solely a bile acid binder. By a low dose of bile acid binder any possible side effects caused by poor tolerance of the patient to the therapeutic dose could also be avoided.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with a bile acid binder.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

According to a further aspect of the invention there is provided a pharmaceutical composition which comprises a compound of formula a), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and a bile acid binder, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising a compound of formula (I), or a pharmaceutically acceptable salt, solvate, solvate of such a salt or a prodrug thereof, and a bile acid binder.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof and a bile acid binder.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, in a first unit dosage form;
b) a bile acid binder; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form;
c) a bile acid binder; in a third unit dosage form; and
d) container means for containing said first, second and third dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a bile acid binder, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) a bile acid binder; in a third unit dosage form; and
d) container means for containing said first, second and third dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, a bile acid binder, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, and a bile acid binder, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a bile acid binder, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable excipient, with the simultaneous, sequential or separate administration of an effective amount of a bile acid binder, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:
- a CETP (cholesteryl ester transfer protein) inhibitor, for example those referenced and described in WO 00/38725 page 7 line 22-page 10, line 17 which are incorporated herein by reference;
- a cholesterol absorption antagonist for example azetidinones such as SCH 58235 and those described in U.S. Pat. No. 5,767,115 which are incorporated herein by reference;
- a MTP (microsomal transfer protein) inhibitor for example those described in Science, 282, 751–54, 1998 which are incorporated herein by reference;
- a fibric acid derivative; for example clofibrate, gemfibrozil, fenofibrate, ciprofibrate and bezafibrate;
- a nicotinic acid derivative, for example, nicotinic acid (niacin), acipimox and niceritrol;
- a phytosterol compound for example stanols;
- probucol;
- an anti-obesity compound for example orlistat (EP 129, 748) and sibutramine (GB 2,184,122 and U.S. Pat. No. 4,929,629);
- an antihypertensive compound for example an angiotensin converting enzyme (ACE) inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, a diuretic or a vasodilator;
- insulin;
- sulphonylureas including glibenclamide, tolbutamide;
- metformin; and/or
- acarbose;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula (I) include but are not limited to, the following compounds: alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula (I) include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

In another aspect of the invention, the compound of formula (I), or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623–634 (in particular the compounds described in the patent applications listed on page 634) and J Med Chem, 2000, 43, 527 which are all incorporated herein by reference. Particularly a PPAR alpha and/or gamma agonist refers to WY-14643, clofibrate, fenofibrate, bezafibrate, GW 9578, troglitazone, pioglitazone, rosiglitazone, eglitazone, proglitazone, BRL-49634, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxyphenyl}ethoxy)phenyl]] propanoic acid and pharmaceutically acceptable salts thereof.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof. According to a further aspect of the present invention there is provided a kit comprising:

a) a compound of formula (I), or a pharmaceutically acceptable salt, solvate, solvate of such a salt or a prodrug thereof, in a first unit dosage form;

b) a PPAR alpha and/or gamma agonist, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) a PPAR alpha and/or gamma agonist, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, a PPAR alpha and/or gamma agonist, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of IBAT in laboratory animals such as cats, dogs, rabbits, monkeys, rats and mice, as part of the search for new therapeutic agents.

Many of the intermediates described herein are novel and are thus provided as a further feature of the invention. For example compounds of formula (VIIIa), (VIIIb), (IXa), (IXb), (XIIIa) and (XIIIb) show IBAT inhibitory activity when tested in the above referenced in vitro test assay and are thus claimed as a further feature of the invention.

Thus in a further feature of the invention, there is provided a compound of formula (VIIIa), (VIIIb), (IXa), (IXb), (XIIIa) or (XIIIb), or a pharmaceutically acceptable salt, solvate, solvate of such a salt or a prodrug thereof.

Therefore according to a further aspect of the invention there is provided a pharmaceutical composition which comprises a compound of formula (VIIIa), (VIIIb), (IXa), (IXb), (XIIIa) or (XIIIb), or a pharmaceutically acceptable salt, solvate, solvate of such a salt or a prodrug thereof, as defined hereinbefore in association with a pharmaceutically-acceptable diluent or carrier.

According to an additional aspect of the present invention there is provided a compound of the formula (VIIIa), (VIIIb), (IXa), (IXb), (XIIIa) or (XIIIb), or a pharmaceutically acceptable salt, solvate, solvate of such a salt or a prodrug thereof, as defined hereinbefore for use in a method of prophylactic or therapeutic treatment of a warm-blooded animal, such as man.

Thus according to this aspect of the invention there is provided a compound of the formula (VIIIa), (VIIIb), (IXa), (IXb), (XIIIa) or (XIIIb), or a pharmaceutically acceptable salt, solvate, solvate of such a salt or a prodrug thereof, as defined hereinbefore for use as a medicament.

According to another feature of the invention there is provided the use of a compound of the formula (VIIIa), (VIIIb), (IXa), (IXb), (XIIIa) or (XIIIb), or a pharmaceutically acceptable salt, solvate, solvate of such a salt or a prodrug thereof as defined hereinbefore in the manufacture of a medicament for use in the production of an IBAT inhibitory effect in a warm-blooded animal, such as man.

According to another feature of the invention there is provided the use of a compound of the formula (VIIIa), (VIIIb),(IXa), (IXb), (XIIIa) or (XIIIb), or a pharmaceutically acceptable salt, solvate, solvate of such a salt or a prodrug thereof as defined hereinbefore in the manufacture of a medicament for use in the treatment of hyperlipidaemic conditions in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (VIIIa), (VIIIb), (IXa), (IXb), (XIIIa) or (XIIIb), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (VIIIa), (VIIIb), (IXa), (IXb), (XIIIa) or (XIIIb), or a pharmaceutically acceptable salt, solvate, solvate of such a salt or a prodrug thereof.

In the above other pharmaceutical composition, process, method, use and medicament manufacture features, the alternative and preferred embodiments of the compounds of the invention described herein also apply.

EXAMPLES

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically in the range 18–25° C., with solvents of HPLC grade under anhydrous conditions, unless otherwise stated;

(iii) column chromatography (by the flash procedure) was performed on Silica gel 40–63 μm (Merck);

(iv) yields are given for illustration only and are not necessarily the maximum attainable;

(v) the structures of the end products of the formula (I) were generally confirmed by nuclear (generally proton) magnetic resonance (NMR) and mass spectral techniques; magnetic resonance chemical shift values were measured in deuterated $CDCl_3$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer unless otherwise stated data was recorded at 400 MHz; and peak multiplicities are shown as follows: s, singlet; d, doublet; dd, double doublet; t, triplet; tt, triple triplet; q, quartet; tq, triple quartet; m, multiplet; br, broad; ABq, AB quartet; ABd, AB doublet, ABdd, AB doublet of doublets; dABq, doublet of AB quartets; LCMS were recorded on a Waters ZMD, LC column xTerra MS $C_8$(Waters), detection with a BP 1100 MS-detector diode array equipped; mass spectra (MS) (loop) were recorded on VG Platform II (Fisons Instruments) with a HP-1100 MS-detector diode array equipped; unless otherwise stated the mass ion quoted is ($MH^+$); unless further details are specified in the text, analytical high performance liquid chromatography (HPLC) was performed on Prep LC 2000 (Waters), Cromasil $C_7$, 7 μm, (Akzo Nobel); MeCN and de-ionised water 10 mM ammonium acetate as mobile phases, with suitable composition;

(vii) intermediates were not generally fully characterised and purity was assessed by thin layer chromatography (TLC), HPLC, infra-red (IR), MS or NMR analysis;

(viii) where solutions were dried sodium sulphate was the drying agent;

(ix) where an "ISOLUTE" column is referred to, this means a column containing 2 g of silica, the silica being contained in a 6 ml disposable syringe and supported by a porous disc of 54 Å pore size, obtained from International Sorbent Technology under the name "ISOLUTE"; "ISOLUTE" is a registered trade mark;

(x) the following abbreviations may be used hereinbefore or hereinafter:

| | |
|---|---|
| DCM | dichloromethane; |
| DMF | N,N-dimethylformamide; |
| TBTU | o-Benzotriazol-1-yl-N,N,N',N'-tetramethyluronium tetrafluoroborate; |
| EtOAc | EtOAC; |
| MeCN | acetonitrile; |
| TFA | trifluoroacetic acid; |
| IPA | isopropanol; |
| DIPEA | di-isopropylethylamine; and |
| THF | tetrahydrofuran. |

Example 1

1,1-Dioxo-3,3-dibutyl-5-phenyl-7-methylthio-8-[N—((R)-1'-phenyl-1'-carboxymethyl)carbamoyl-methoxy]-2,3,4,5-tetrahydro-1,5-benzothiazepine 1,1-Dioxo-3,3-dibutyl-5-phenyl-7-methylthio-8-[N—((R)-1'-phenyl-1'-methoxycarbonylmethyl)carbamoyl-methoxy]-2,3,4,5-tetrahydro-1,5-benzothiazepine (Method 29; 300 mg, 0.46 mmol) was dissolved in methanol (5 ml). NaOH (100 mg in 0.2 ml water) was added to the solution and the mixture was stirred at room temperature for 1 hour. Acetic acid (0.3 ml) was added. The solvent was evaporated under reduced pressure and the residue was extracted with DCM/water. The DCM layer was separated, dried and evaporated under reduced pressure to give the title compound 270 mg (92%). NMR, 500 MHz) 0.7–0.8 (m, 6H), 1.0–1.6 (m, 12H), 2.1 (s, 3H) 3.2 (brs, 2H), 3.6–3.8 (m, 2H), 4.6 (s, 2H), 5.6 (d, 1H), 6.6 (s, 1H), 6.9–7.5 (m, 11H), 7.8 (d, 1H).

Examples 2–9

The following compounds were synthesised by the procedure of Example 1 using the appropriate starting material.

| Ex | Compound | NMR | SM |
|---|---|---|---|
| 2 | (structure: 4-hydroxyphenyl glycine amide linked via OCH2C(O)NH to benzothiazepine dioxide core with SMe, dibutyl, N-phenyl) | (300MHz, CD3OD) 0.9–0.95 (m, 6H), 1.05–1.3(m, 8H), 1.4–1.6(m, 4H), 2.2(s, 3H), 3.25(s, 2H), 3.75(brs, 2H), 4.65(dd, 2H), 5.2(s, 1H), 6.7–7.3(m, 10H), 7.4(s, 1H) | Meth 30 |
| 3 | (structure: 2-thienyl glycine amide linked via OCH2C(O)NH to benzothiazepine dioxide core with SMe, dibutyl, N-phenyl) | (300MHz, CD3OD) 0.75–0.85 (m, 6H), 1.0–1.6(m, 12H), 2.2 (s, 3H), 3.75(brs, 2H), 3.25(s, 2H), 4.6–4.7(m, 2H), 5.7(s, 1H), 6.7(s, 1H), 6.9–7.3(m, 8H), 7.4(s, 1H) | Meth 31 |
| 4 | (structure: 4-trifluoromethylphenyl glycine amide linked via OCH2C(O)NH to benzothiazepine dioxide core with SMe, dibutyl, N-phenyl) | (300MHz, CD3OD) 0.75–0.9 (m, 6H), 1.0–1.6(m, 12H), 2.2 (s, 3H), 3.25(s, 2H), 3.75(brs, 2H), 4.6–4.8(m, 2H), 5.45(s, 1H), 6.7(s, 1H), 6.95–7.3(m, 5H), 7.4(s, 1H), 7.6(s, 4H) | Meth 32 |
| 5 | (structure: 3-hydroxyphenyl glycine amide linked via OCH2C(O)NH to benzothiazepine dioxide core with Br, dibutyl, N-phenyl) | (500MHz) 0.7–0.8(m, 6H), 1.0–1.6(m, 12H), 3.2(brs, 2H), 3.6 (brs, 2H), 4.48(m, 2H), 5.0(s, 1H), 6.5(d, 1H), 6.7–7.4(m, 10H), 7.9(s, 1H) | Meth 39 |

-continued

| Ex | Compound | NMR | SM |
|---|---|---|---|
| 6 | | (DMSO-d$_6$) 0.7–0.8(m, 6H), 0.9–1.6(m, 12H), 3.2(brs, 2H), 3.7(brs, 2H), 4.6–4.8(m, 3H), 6.6(d, 2H), 6.9–7.3(m, 8H), 7.4 (s, 1H), 8.3(d, 1H) | Meth 40 |
| 7 | | M/z = 768.9 | Meth 67 |
| 8[1] | | (300MHz, CD$_3$OD) 0.75–0.9 (m, 6H), 1.0–1.25(m, 4H), 1.4–1.6(m, 4H), 2.15(s, 3H), 3.1–3.3(m, 4H), 3.5–3.8(m, 5H), 4.75(ABq, 2H), 5.45(s, 2H), 6.75(s, 1H), 6.95–7.5(11H); m/z 711.3 | Meth 42 |
| 9 | | (500MHz, DMSO-d$_6$) 0.7–0.8 (m, 6H), 0.9–1.6(m, 12H), 2.2 (s, 3H) 3.2–3.8(m, 8H), 4.8 (ABq, 2H), 5.6(d, 1H), 6.7(s, 1H), 6.8–7.5(m, 11H), 7.8(brs, 1H), 8.6(d, 1H), 8.8(t, 1H) | Meth 69 |

[1] Ethanol instead of methanol, purified by preparative HPLC using MeCN and ammonium acetate buffer(55:45) as eluent

Example 10

1,1-Dioxo-3-butyl-3-ethyl-5-phenyl-7-bromo-8-{1-[N—((R)-1'-phenyl-1'-carboxymethyl)carbamoyl]ethoxy}-2,3,4,5-tetrahydro-1,5-benzothiazepine 1,1-Dioxo-3-butyl-3-ethyl-5-phenyl-7-bromo-8-{1-[N—((R)-1'-phenyl-1'-methoxycarbonylmethyl)carbamoyl]ethoxy}-2,3,4,5-tetrahydro-1,5-benzothiazepine (Method 33; 103 mg, 0.15 mmol) was dissolved in a mixture of THF and H$_2$O (2:1, 3 ml). LiOH (7 mg, 0.3 mmol) was added and the mixture was stirred for 7 hours at ambient temperature. Most of the solvent was removed under reduced pressure and the crude product was purified by preparative HPLC using MeCN and ammonium acetate buffer (45:55) as eluent to give the title compound 97 mg (96%). NMR (DMSO-d$_6$) 0.60–0.80 (m, 6H), 0.90–1.60 (m, 11H), 3.15–3.45 (m, 2H), 3.50–3.90 (m, 2H), 4.95–5.25 (m, 2H), 6.85–7.55 (m, 12H), 8.55–8.95 (m, 1H).

Examples 11–16

The following compounds were synthesised by the procedure of Example 10 using the appropriate starting material.

| Ex | Compound | NMR | SM |
|---|---|---|---|
| 11 | [structure] | ((CD$_3$)$_2$CO) 0.70–0.90(m, 6H), 0.95–1.35(m, 4H), 1.40–1.75(m, 4H), 3.15–3.35(m, 2H), 3.80(brs, 2H), 5.40(d, 1H), 5.90–6.15(2s, 1H), 6.95–7.75(m, 18H) | Meth 34 |
| 12 | [structure] | (CD$_3$OD) 0.75–0.85(m, 6H), 1.00–1.30(m, 8H), 1.35–1.55(m, 4H), 3.20(s, 2H), 3.60(s, 3H), 3.75(brs, 2H), 4.60(ABq, 2H), 5.40(s, 1H), 6.50(s, 1H), 6.95–7.45(m, 10H), 7.55(s, 1H) | Meth 35 |
| 13 | [structure] | (CD$_3$OD) 0.75–0.85(m, 6H), 1.00–1.30(m, 8H), 1.35–1.55(m, 4H), 3.20(s, 2H), 3.55(s, 3H), 3.75(brs, 2H), 3.90(ABq, 2H), 4.60(ABq, 2H), 5.60(s, 1H), 6.50(s, 1H), 6.95–7.45(m, 10H), 7.55(s, 1H) | Meth 36 |

| Ex | Compound | NMR | SM |
|---|---|---|---|
| 14 | | (CD₃OD) 0.75–0.85(m, 6H), 1.00–1.30(m, 8H), 1.35–1.60(m, 4H), 3.20(s, 2H), 3.60(s, 3H), 3.75(brs, 2H), 4.55(ABq, 2H), 5.55(s, 1H), 6.50(s, 1H), 6.95–7.45(m, 9H), 7.50(s, 1H) | Meth 37 |
| 15 | | (CD₃OD) 0.75–0.85(m, 6H), 1.00–1.30(m, 8H), 1.35–1.60(m, 4H), 2.15(s, 3H), 3.25(s, 2H), 3.75(brs, 2H), 4.65(ABq, 2H), 5.60(s, 1H), 6.70(s, 1H), 6.90–7.45(m, 10H) | Meth 38 |
| 16 | | (CD₃OD) 7.55–7.41(3H, m), 7.35–7.20(5H, m), 7.15–7.08(3H, m), 7.04–6.98(1H, m), 5.48–5.32(1H, m), 4.80–4.60(2H, m), 4.00–3.56 (4H, m), 3.27–3.22(2H, m), 1.61–1.00(11H, m), 0.83–0.74(6H, m) | Meth 70 |

Example 17

1,1-Dioxo-3-butyl-3-ethyl-5-phenyl-7-bromo-8-[N-((S)-1'-phenyl-1'-carboxymethyl)carbamoylmethoxy]-2,3,4,5-tetrahydro-1,5-benzothiazepine 1,1-Dioxo-3-butyl-3-ethyl-5-phenyl-7-bromo-8-[N-((S)-1'-phenyl-1'-methoxycarbonylmethyl)carbamoylmethoxy]-2,3,4,5-tetrahydro-1,5-benzothiazepine (Method 46; 60 mg, 0.091 mmol) was dissolved in THF (1 ml) and added to a solution of lithium hydroxide monohydrate (12.6 mg, 0.29 mmol) in water (1 ml). The mixture was stirred occasionally for 30 minutes. 2M HCl solution (0.3 ml) was added and the water layer was extracted with DCM. The organic layer was washed once with brine, dried, filtered and evaporated at reduced pressure to give the title compound 48 mg (82%). NMR (CD₃OD) 0.73–0.84 (m, 6H), 1.0–1.6 (m, 8H), 3.27 (brs, 2H), 3.60–3.90 (m, 2H), 4.71 (ABq, 2H), 5.47–5.55 (m, 1H), 7.02 (brt, 1H), 7.08–7.17 (m, 3H), 7.25–7.46 (m, 7H), 7.52 (s, 1H), 8.43 (d, NH); m/z 643.5.

Examples 18–21

The following compounds were synthesised by the procedure of Example 17 using the appropriate starting material.

| Ex | Compound | NMR or m/z | SM |
|---|---|---|---|
| 18[1] | | M/z 670(M + NH$_4^+$) | Meth 43 |
| 19[2] | | (CD$_3$OD) 0.70–0.90(m, 6H), 1.0–1.32(m, 4H), 1.32–1.70(m, 4H), 2.15(s, 3H), 2.85(brs, 3H), 3.23 (brs, 2H), 3.53–3.93(m, 2H), 4.99 (ABq, 2H), 6.27(s, 1H), 6.71(s, 1H), 6.94(t, 1H), 7.07(d, 2H), 7.25 (t, 2H), 7.3–7.47(m, 6H); m/z 625.3 | Meth 62 |
| 20 | | (CD$_3$OD) 0.75–0.84(m, 6H), 1.0–1.29(m, 4H), 1.36–1.65(m, 4H), 2.15(s, 3H), 2.82–2.97(m, 2H), 3.22(brs, 2H), 3.6–3.85(m, 2H), 4.66(ABq, 2H), 5.43(t, 1H), 6.71 (s, 1H), 6.96(t, 1H), 7.09(d, 2H), 7.2–7.38(m, 7H), 7.40(s, 1H); m/z 625.4 | Meth 112 |
| 21 | | (600MHz, CD$_3$OD) 0.77–0.88(m, 6H), 1.0–1.32(m, 4H), 1.39–1.70 (m, 4H), 2.16(s, 3H), 2.88(brs, 3H), 3.25(brs, 2H), 3.52–3.93(m, 2H), 5.03(ABq, 2H), 6.28(s, 1H), 6.73(s, 1H), 6.96(t, 1H), 7.09(brd, 2H), 7.27(t, 2H), 7.32–7.46(m, 6H) | Meth 79 |

[1] 2.2 equivalents of LiOH in THF/water (4/1)
[2] Purified by preparative HPLC using an MeCN/ammonium acetate buffer gradient(5/95 to 100/0) as eluent

Example 22

1,1-Dioxo-3-butyl-3-ethyl-5-phenyl-7-bromo-8-[N-((R)-1'-phenyl-1'-carboxymethyl)carbamoylmethoxy]-2,3,4,5-tetrahydro-1,5-benzothiazepine

The title compound was synthesised from 1,1-Dioxo-3-butyl-3-ethyl-5-phenyl-7-bromo-8-[N-((R)-1'-phenyl-1'-methoxycarbonylmethyl)carbamoylmethoxy]-2,3,4,5-tetrahydro-1,5-benzothiazepine (Method 61) by the procedure of Example 17, except that the water layer was extracted with EtOAc. The product was purified by preparative HPLC using an MeCN/ammonium acetate buffer gradient (5/95 to 100/0) as eluent. NMR 0.75–0.83 (m, 6H), 1.0–1.25 (m, 4H), 1.32–1:52 (m, 3H), 1.55–1.70 (m, 1H), 3.20 (ABq, 2H), 3.65–3.83 (m, 2H), 4.62 (ABq, 2H), 5.68 (d, 1H), 7.04–7.15 (m, 4H), 7.3–7.5 (m, 8H), 7.87 (brd, 1H); m/z 643.1.

Example 23

1,1-Dioxo-3-butyl-3-ethyl-5-phenyl-7-bromo-8-(N-{(S)-1'-phenyl-1'-[N'-(2-sulphoethyl)carbamoyl]methyl}carbamoylmethoxy)-2,3,4,5-tetrahydro-1,5-benzothiazepine ammonium salt

1,1-Dioxo-3-butyl-3-ethyl-5-phenyl-7-bromo-8-[N-((S)-1'-phenyl-1'-carboxymethyl)carbamoylmethoxy]-2,3,4,5-tetrahydro-1,5-benzothiazepine (Example 17; 48 mg, 0.075 mmol) and 2-aminoethanesulphonic acid (17 mg, 0.14 mmol) was dissolved in DMF (2 ml) and DIPEA (0.052 ml, 0.30 mmol). The mixture was stirred for 15 min at 60° C. TBTU (31 mg, 0.097 mmol) was added and the mixture was stirred for 2 hours at 60° C. The solvent was evaporated at reduced pressure. The residue was purified by preparative HPLC using an MeCN/ammonium acetate buffer gradient (5/95 to 100/0) as eluent. Lyophilisation gave the title compound 4 mg (7%). NMR (CD$_3$OD) 0.75–0.83 (m, 6H), 0.95–1.65 (m, 8H), 2.85–3.0 (m, 2H), 3.27 (brs, 2H), 3.5–3.9 (m, 4H), 4.72 (ABq, 2H), 5.48 (s, 1H), 7.02 (brt, 1H), 7.09–7.15 (m, 3H), 7.25–7.52 (m, 8H); m/z 750.3.

Examples 24–37

The following compounds were prepared by the same procedure. The acid (1 equiv) was dissolved in THF (1 ml) and added to a solution of lithium hydroxide monohydrate (12.6 mg, 2.9–6.6 equiv) in water (1 ml). The mixture was stirred occasionally and after 1.5–6 hours the deprotection was completed (according to LC-MS). 2M HCl-solution (0.3 ml) was added.

Examples 24–33

The reaction mixture was put on a syringe filled with hydramatrix®. The product was eluted with DCM. The DCM was dried, filtered and evaporated at reduced pressure. The product was purified by preparative HPLC using an MeCN/ammonium acetate buffer gradient (5/95 to 100/0) as eluent.

Examples 34–37

The water layer was extracted two times with DCM. The organic layer was dried, filtered and evaporated at reduced pressure.

| Ex | Compound | NMR(CD$_3$OD) | m/z | SM |
|---|---|---|---|---|
| 24 | (structure with MeO, phenyl, butyl, ethyl, N-phenyl benzothiazepine dioxide) | 0.75–0.84(m, 6H), 1.0–1.25(m, 4H), 1.37–1.65(m, 4H), 3.20 (brs, 2H), 3.55–3.90(m, 5H), 4.58(ABq, 2H), 5.33(s, 1H), 6.51(s, 1H), 6.97(brt, 1H), 7.12 (brd, 2H), 7.2–7.33(m, 5H), 7.41 (brd, 2H), 7.54(s, 1H) | 595.4 | Meth 47 |
| 25 | (structure with MeS, phenyl, butyl, ethyl, N-phenyl benzothiazepine dioxide) | 0.73–0.85(m, 6H), 1.0–1.3(m, 4H), 1.35–1.65(m, 4H), 2.17(s, 3H), 3.23(brs, 2H), 3.55–3.90 (m, 2H), 4.71(ABq, 2H), 5.49–5.52(m, 1H), 6.73(s, 1H), 6.96 (brt, 1H), 7.10(brd, 2H), 7.23–7.45(m, 8H), 8.36(brd, NH) | 611.2 | Meth 48 |

-continued

| Ex | Compound | NMR(CD₃OD) | m/z | SM |
|---|---|---|---|---|
| 26 | | 0.74–0.84(m, 6H), 1.0–1.3(m, 8H), 1.37–1.54(m, 4H), 3.28 (brs, 2H), 3.65–3.85(m, 2H), 4.72(ABq, 2H), 5.49–5.52(m, 1H), 7.04(brt, 1H), 7.09–7.18 (m, 3H), 7.28–7.46(m, 7H), 7.52 (s, 1H), 8.45(brd, NH) | 671.2 | Meth 49 |
| 27 | | 0.74–0.84(m, 6H), 1.0–1.3(m, 4H), 1.35–1.65(m, 4H), 3.21 (brs, 2H), 3.59(s, 3H), 3.62–3.90 (m, 2H), 4.62(ABq, 2H), 5.49 (s, 1H), 6.50(s, 1H) 6.98(brt, 1H), 7.12(brd, 2H), 7.24–7.43 (m, 7H), 7.54(s, 1H) | 595.3 | Meth 50 |
| 28 | | 0.74–0.85(m, 6H), 0.85–1.65(m, 14H), 3.21(brs, 2H), 3.6–3.9(m, 2H), 4.25–4.36(m, 1H), 4.53–4.66(m, 2H), 5.49(s, 1H), 6.47 (s, 1H) 6.91–7.0(m, 1H), 7.04–7.16(m, 2H), 7.22–7.46(m, 7H), 7.51(s, 1H) | 623.3 | Meth 51 |
| 29 | | 0.73–0.85(m, 6H), 0.85–1.65(m, 8H), 3.24(brs, 3H), 3.34(brs, 2H), 3.6–3.95(m, 2H), 4.8–4.95 (m, 2H), 5.52(s, 1H), 7.06(brt, 1H), 7.17(brd, 2H), 7.27–7.40 (m, 5H), 7.40–7.50(m, 3H), 7.69 (s, 1H) | 643.3 | Meth 52 |

-continued

| Ex | Compound | NMR(CD₃OD) | m/z | SM |
|---|---|---|---|---|
| 30 | | 0.74–0.84(m, 6H), 0.85–1.55(m, 12H), 3.24–3.33(m, 2H), 3.65–3.85(m, 2H), 4.65–4.78(m, 2H), 5.50(brs, 1H), 6.99–7.2(m, 4H), 7.25–7.48(m, 7H), 7.51(s, 1H) | 671.2 | Meth 53 |
| 31 | | 0.72–0.84(m, 6H), 0.85–1.65(m, 8H), 3.27(brs, 2H), 3.54–3.9(m, 2H), 4.70(ABq, 2H), 5.70(s, 1H), 6.63–6.69(m, 1H), 6.71–6.77(m, 2H), 7.02(brt, 1H), 7.08–7.17(m, 3H), 7.30(brt, 2H), 7.52(s, 1H) | 675.4 | Meth 54 |
| 32 | | 0.72–0.84(m, 6H), 0.98–1.67(m, 8H), 3.21(brs, 2H), 3.54–3.9(m, 5H), 4.62(ABq, 2H), 5.57(s, 1H), 6.51(s, 1H), 6.59–6.73(m, 3H), 6.97(brt, 1H), 7.12(brd, 2H), 7.28(brt, 2H), 7.56(s, 1H) | 627.5 | Meth 55 |
| 33 | | 0.73–0.86(m, 6H), 1.0–1.68(m, 8H), 2.19(s, 3H), 3.24(brs, 2H), 3.55–3.9(m, 2H), 4.71(ABq, 2H), 5.53(s, 1H), 6.60–6.73(m, 3H), 6.75(s, 1H), 6.96(brt, 1H), 7.10(brd, 2H), 7.27(brt, 2H), 7.44(s, 1H) | 643.4 | Meth 56 |

-continued

| Ex | Compound | NMR(CD₃OD) | m/z | SM |
|---|---|---|---|---|
| 34 | (structure) | 0.74–0.86(m, 6H), 1.0–1.3(m, 8H), 1.35–1.57(m, 4H), 2.19(s, 3H), 3.23(brs, 2H), 3.62–3.85 (m, 2H), 4.65(ABq, 2H), 5.28 (s, 1H), 6.72(s, 1H), 6.94–7.05 (m, 3H), 7.12(brd, 2H), 7.28 (brt, 2H), 7.39(s, 1H), 7.43(dd, 2H) | 657.3 | Meth 57 |
| 35 | (structure) | 0.75–0.86(m, 6H), 1.0–1.3(m, 8H), 1.35–1.55(m, 4H), 2.01(s, 3H), 3.11–3.26(ABq, 2H), 3.6–3.8(m, 2H), 4.58(d, 1H), 4.70 (d, 1H), 5.64(s, 1H), 6.62(s, 1H), 6.91–7.0(m, 2H), 7.01–7.12 (m, 3H), 7.23–7.33(m, 4H), 7.37 (s, 1H), 7.69(brd, 1H) | 678.4 | Meth 58 |
| 36 | (structure) | 0.76–0.84(m, 6H), 1.0–1.3(m, 8H), 1.36–1.53(m, 4H), 3.21 (brs, 2H), 3.64(s, 3H), 3.67–3.87 (m, 2H), 4.57(ABq, 2H), 5.31 (s, 1H), 6.50(s, 1H), 6.95–7.06 (m, 3H), 7.14(brd, 2H), 7.28 (brt, 2H), 7.38–7.46(m, 2H), 7.51(s, 1H) | 641.4 | Meth 59 |
| 37 | (structure) | 0.75–0.87(m, 6H), 1.0–1.3(m, 8H), 1.34–1.53(m, 4H), 3.18 (ABq, 2H), 3.27(s, 3H), 3.65–3.85(m, 2H), 4.52(d, 1H), 4.65 (d, 1H), 5.66(s, 1H), 6.30(s, 1H), 6.90–7.02(m, 2H), 7.03–7.16(m, 3H), 7.23–7.34(m, 4H), 7.50(s, 1H), 7.59(brd, 1H) | 662.4 | Meth 60 |

Example 38

1,1-Dioxo-3-butyl-3-ethyl-5-phenyl-7-methylthio-8-[N-((R)-1'-phenyl-1'-carboxymethyl)carbamoylmethoxy]-2,3,4,5-tetrahydro-1,5-benzothiazepine 1,1-Dioxo-3-butyl-3-ethyl-5-phenyl-7-bromo-8-[N-((R)-1'-phenyl-1'-carboxymethyl)carbamoylmethoxy]-2,3,4,5-tetrahydro-1,5-benzothiazepine (Example 22; 50 mg, 0.078 mmol) was dissolved in DMF (1.5 ml). Sodium methanethiolate (20 mg, 0.29 mmol) was added and the mixture was stirred for 1.5 hours at 50° C. Acetic acid (40 mg) was added and the solvent was evaporated under reduced pressure. The residue was purified by preparative HPLC using MeCN/ammonium acetate buffer (45:55) as eluent to give the title compound 29 mg (61%). NMR (DMSO-$d_6$): 0.7–0.8 (m, 6H), 0.9–1.6 (m, 8H), 2.2 (s, 3H), 3.1–3.7 (m, 4H), 4.6–4.8 (m, 3H), 6.7 (s, 1H), 6.8–7.4 (m, 11H), 8.3 (d, 1H).

Example 39

1,1-Dioxo-3-butyl-3-ethyl-5-phenyl-7-ethylthio-8-[N-((R)-1'-phenyl-1'-carboxymethyl)carbamoylmethoxy]-2,3,4,5-tetrahydro-1,5-benzothiazepine 1,1-Dioxo-3-butyl-3-ethyl-5-phenyl-7-bromo-8-[N-((R)-1'-phenyl-1'-carboxymethyl)carbamoylmethoxy]-2,3,4,5-tetrahydro-1,5-benzothiazepine (Example 22; 50 mg, 0.078 mmol), ethanethiol (99 mg, 1.59 mmol) and caesium carbonate (253 mg, 0.78 mmol) were added to DMF (5 ml) and the mixture was stirred for 30 h at 44° C. The solvent was filtered, evaporated under reduced pressure. The residue was purified by preparative HPLC using MeCN/ammonium acetate buffer (45:55) as eluent. The residue was purified by column chromatography using DCM methanol (100:15) to give the title compound 15 mg (31%). NMR (300 MHz, CD$_3$OD) 0.7–0.85 (m, 6H), 1.0–1.6 (m, 11H), 2.65 (q, 2H), 3.2 (s, 2H), 3.7 (brs, 2H), 4.6 (q, 2H), 5.3 (s, 1H), 6.75 (s, 1H), 6.9–7.5 (m, 11H).

Example 40

1,1-Dioxo-3-butyl-3-ethyl-5-phenyl-7-(2-hydroxyethylthio)-8-[N-((R)-1'-phenyl-1'-carboxymethyl)carbamoylmethoxy]-2,3,4,5-tetrahydro-1,5-benzothiazepine 1,1-Dioxo-3-butyl-3-ethyl-5-phenyl-7-bromo-8-[N-((R)-1'-phenyl-1'-carboxymethyl)carbamoylmethoxy]-2,3,4,5-tetrahydro-1,5-benzothiazepine (Example 22; 50 mg, 0.078 mmol), 2-mercaptoethanol (281 mg, 3.59 mmol) and caesium carbonate (228 mg, 0.7 mmol) were added to DMF (5 ml) and the mixture was stirred for 9 hours at 70° C. The solvent was evaporated under reduced pressure. The residue was purified by preparative HPLC using MeCN/ammonium acetate buffer (45:55) as eluent. The collected fractions were lyophilised to give the title compound 20 mg (40%). NMR (300 MHz, CD$_3$OD) 0.75–0.85 (m, 6H), 1.0–1.6 (m, 8H), 2.9 (t, 2H), 3.2 (s, 2H), 3.55 (t, 2H), 3.7 (brs, 2H), 4.65 (q, 2H), 5.3 (s, 1H), 6.9 (s, 1H), 6.95–7.5 (m, 11H).

Example 41

1,1-Dioxo-3-butyl-3-ethyl-5-phenyl-7-(2-N',N'-dimethylaminoethylthio)-8-[N-((R)-1'-phenyl-1'-carboxymethyl)carbamoylmethoxy]-2,3,4,5-tetrahydro-1,5-benzothiazepine 1,1-Dioxo-3-butyl-3-ethyl-5-phenyl-7-bromo-8-[N-((R)-1'-phenyl-1'-carboxymethyl)carbamoylmethoxy]-2,3,4,5-tetrahydro-1,5-benzothiazepine (Example 22; 50 mg, 0.078 mmol), dimethylaminoethanethiol hydrochloride (99 mg, 0.94 mmol), potassium carbonate (129 mg, 0.94 mmol), DIPEA (100 mg, 0.77 mmol) and sodium borohydride (35 mg, 0.93 mmol) were added to DMF (10 ml) and the mixture was stirred for 24 hours at 85° C. The solvent was filtered and evaporated under reduced pressure. The residue was purified twice by preparative HPLC using MeCN/ammonium acetate buffer (40:60) as eluent. The collected fractions were lyophilised to give the title compound. 15 mg (30%). NMR (300 MHz, CD$_3$OD) 0.75–0.85 (m, 6H), 1.0–1.65 (m, 8H), 2.65 (s, 6H), 3.05 (t, 2H), 3.2 (t, 2H), 3.3 (s, 2H), 3.75 (brs, 2H), 4.75 (s, 2H), 5.2 (s, 1H), 6.95–7.4 (m, 11), 7.5 (s, 1H).

Example 42

1,1-Dioxo-3-butyl-3-ethyl-5-phenyl-7-isopropylthio-8-[N-((R)-1'-phenyl-1'-carboxymethyl)carbamoylmethoxy]-2,3,4,5-tetrahydro-1,5-benzothiazepine 1,1-Dioxo-3-butyl-3-ethyl-5-phenyl-7-bromo-8-[N-((R)-1'-phenyl-1'-carboxymethyl)carbamoylmethoxy]-2,3,4,5-tetrahydro-1,5-benzothiazepine (Example 22; 50 mg, 0.078 mmol), 2-propanethiol (126 mg, 1.65 mmol), caesium carbonate (152 mg, 0.47 mmol), sodium borohydride (25 mg, 0.66 mmol) were added to DMF (5 ml) and the mixture was stirred for 5 min at 100° C. The solvent was evaporated under reduced pressure. The residue was purified by preparative HPLC using MeCN/ammonium acetate buffer (45:55) as eluent. The collected fractions were lyophilised to give the title compound 15 mg (30%). NMR (300 MHz, DMSO-$d_6$) 0.7–0.85 (m, 6H), 0.95–1.65 (m, 14H), 3.3 (s, 2H), 3.7 (brs, 2H), 4.75 (dd, 2H), 5.05 (brs, 1H), 6.75–7.4 (m, 12H), 8.5 (brs, 1H).

Example 43

1,1-Dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine 1,1-Dioxo-3,3-dibutyl-5-phenyl-7-methylthio-8-(N-{(R)-1'-phenyl-1'-[N'-(t-butoxycarbonylmethyl)carbamoyl]methyl}carbamoylmethoxy)-2,3,4,5-tetrahydro-1,5-benzothiazepine (Method 63; 120 mg, 0.17 mmol) was dissolved in DCM (2 ml). TFA (0.7 ml) was added and the mixture was stirred at room temperature for 3 h. The reaction mixture was evaporated under reduced pressure. The residue was purified by preparative HPLC using MeCN/ammonium acetate buffer (50:50) as eluent to give the title compound 95 mg (85%). NMR (300 MHz, DMSO-$d_6$) 0.7–0.8 (m, 6H), 0.9–1.6 (m, 12H), 2.2 (s, 3H) 3.2–3.3 (m, 2H), 3.5–3.8 (m, 4H), 4.8 (ABq, 2H), 5.6 (d; 1H), 6.7 (s, 1H), 6.8–7.5 (m, 11H), 8.5–8.7 (m, 2H).

Examples 44–49

The following compounds were synthesised by the procedure of Example 43 using the appropriate starting material.

| Ex | Compound | NMR or m/z | SM |
|---|---|---|---|
| 44 | 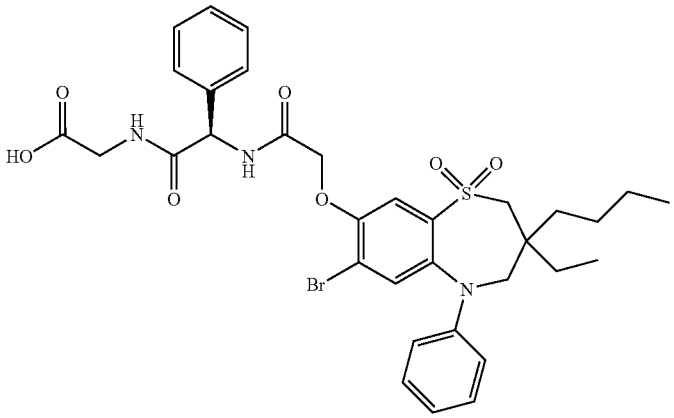 | (300MHz) 0.7–0.9(m, 6H), 1.0–1.7(m, 8H), 3.2(m, 2H), 3.75(brs, 2H), 3.9–4.0(m, 1H), 4.15–4.25(m, 1H), 4.5–4.7(m, 2H), 5.75–5.9(m, 1H), 7.05–7.2(m, 4H), 7.25–7.4(m, 5H), 7.45–7.55(m, 3H), 8.2(d, 1H) | Meth 64 |
| 45 | 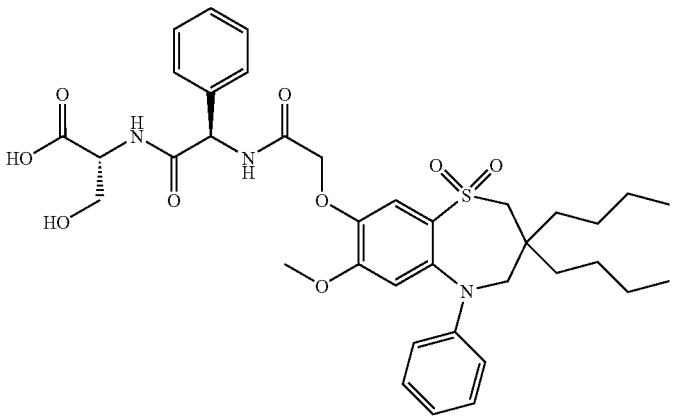 | (CD$_3$OD) 0.70–0.90(m, 6H), 1.00–1.30(m, 8H), 1.35–1.55(m, 4H), 3.20(s, 2H), 3.55(s, 3H), 3.75(brs, 2H), 3.80–4.00(m, 2H), 4.40–4.70(m, 3H), 5.65(s, 1H), 6.50(s, 1H), 6.95–7.50(m, 10H), 7.55(s, 1H) | Meth 41 |
| 46 | 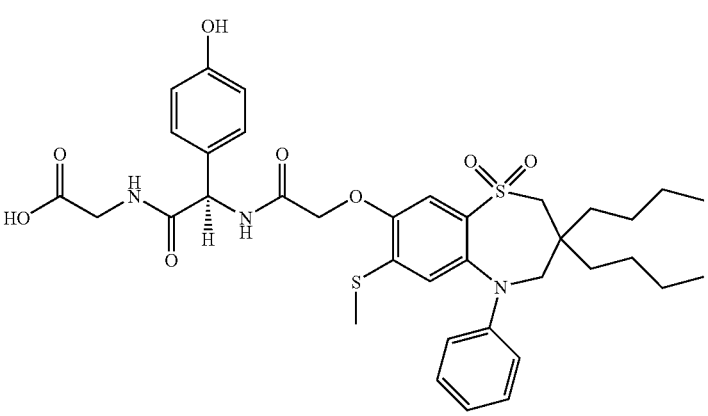 | (300MHz, CD$_3$OD) 0.75–0.85(m, 6H), 1.05–1.3(m, 8H), 1.4–1.6(m, 4H), 2.2(s, 3H), 3.25(2H), 3.7–3.95(m, 4H), 4.7(ABq, 2H), 5.5(s, 1H), 6.7(s, 1H), 6.75–7.35(m, 9H), 7.4(s, 1H) | Meth 65 |

| Ex | Compound | NMR or m/z | SM |
|---|---|---|---|
| 47 | [structure] | 783.5 | Meth 66 |
| 48 | [structure] | 802.7 | Meth 68 |
| 49 | [structure] | (500MHz, CD₃OD) 0.82(brt, 6H), 1.05–1.26(m, 8H), 1.42–1.56(m, 4H), 3.27(brs, 2H), 3.6–3.75(m, 2H), 4.58(ABq, 2H), 5.41(s, 1H), 6.73–6.82(m, 3H), 7.0(d, 2H), 7.05 (dd, 1H), 7.25–7.36(m, 3H), 7.41 (brd, 2H), 7.48(d, 1H); m/z 608.3 | Ex 119 |

Example 50

1,1-Dioxo-3,3-dibutyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine ammonium salt.

1,1-Dioxo-3,3-dibutyl-5-phenyl-7-methylthio-8-carboxymethoxy-2,3,4,5-tetrahydro-1,5-benzothiazepine (Method 22; 150 mg, 0.30 mmol) and 2-((2'R)-2'-amino-2'-phenylethanoylamino)ethanesulphonic acid (Method 28; containing DIPEA hydrochloride, 150 mg, 0.36 mmol) was dissolved in DMF (6 ml). DIPEA (0.2 ml, 1.15 mmol) and TBTU (114 mg, 0.36 mmol) were added and the mixture was stirred for 2 hours at room temperature. The solvent was evaporated at reduced pressure. The residue was purified by preparative HPLC using an MeCN/ammonium acetate buffer gradient (5/95 to 100/0) as eluent to give the title compound 73 mg (32%). NMR (CD₃OD) 0.75–0.85 (m, 6H), 1.0–1.3 (m, 8H), 1.3–1.6 (m, 4H), 2.16 (s, 3H), 2.85–3.0 (m, 2H), 3.24 (brs, 2H) 3.5–3.85 (m, 4H), 4.70 (ABq, 2H), 5.47 (s, 1H), 6.71 (s, 1H), 6.97 (brt, 1H), 7.11 (brd, 2H), 7.23–7.45 (m, 8H); m/z 746.2.

Example 51

1,1-Dioxo-3-butyl-3-ethyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine Ammonium Salt 1,1-Dioxo-3-butyl-3-ethyl-5-phenyl-7-methylthio-8-carboxymethoxy-2,3,4,5-tetrahydro-1,5-benzothiazepine (Method 17; 49 mg, 0.10 mmol) and 2-((2'R)-2'-amino-2'-phenylethanoylamino)ethanesulphonic acid (Method 28; containing DIPEA hydrochloride; 52 mg, 0.12 mmol) was dissolved in DMF(2 ml). DIPEA (0.071 ml, 0.41 mmol) and TBTU (39 mg, 0.12 mmol) was added and the mixture was stirred for 2 hours at room temperature. The solvent was evaporated at reduced pressure. The residue was purified by preparative HPLC using an MeCN/ammonium acetate buffer gradient (5/95 to 100/0) as eluent to give the title compound 59 mg (78%). NMR (CD$_3$OD) 0.74–0.90 (m, 6H), 0.98–1.3 (m, 4H), 1.35–1.6 (m, 4H), 2.16 (s, 3H), 2.85–3.02 (m, 2H), 3.23 (brs, 2H) 3.52–3.90 (m, 4H), 4.70 (ABq, 2H), 5.47 (s, 1H), 6.71 (s, 1H), 6.96 (brt, 1H), 7.09 (brd, 2H), 7.21–7.48 (m, 8H); m/z 718.4.

Example 52

1,1-Dioxo-3-butyl-3-ethyl-5-phenyl-7-methylthio-8-(N-{(R)-1'-phenyl-1'-[N-(carboxymethyl)carbamoyl]methyl}carbamoylmethoxy)-2,3,4,5-tetrahydro-1,5-benzothiazepine 1,1-Dioxo-3-butyl-3-ethyl-5-phenyl-7-methylthio-8-(N-{(R)-1'-phenyl-1'-[N-(ethoxycarbonmethyl)carbamoyl]methyl}carbamoylmethoxy)-2,3,4,5-tetrahydro-1,5-benzothiazepine (Method 72; 44 mg, 0.063 mmol) was dissolved in THF: H$_2$O, 1:1, (2 ml) and NaOH (1 M, 0.126 mmol) was added. The mixture was stirred at ambient temperature for 1 hour. The reaction mixture was acidified with HCl (1 M), diluted to 10 ml and extracted with DCM (3×10 ml). The combined organic layers were dried (MgSO$_4$) and the solvent was evaporated to give the title compound 33 mg (78%). NMR (300 MHz) 0.78–0.85 (m, 6H), 1.02–1.70 (m, 8H), 2.20 (s, 3H), 3.15/3.21 (ABq, 2H), 3.78 (m, 2H), 3.94/4.20 (dABq, 2H), 4.64 (q, 2H), 5.91 (d, 1H), 6.65 (s, 1H), 6.98–7.52 (m, 11H), 8.17 (d, 1H).

Example 53

1,1-Dioxo-3-butyl-3-ethyl-5-phenyl-7-methylthio-8-(N-{(R)-1'-phenyl-1'-[N-(1"-carboxy-1"-phenylmethyl)carbamoyl]methyl}carbamoylmethoxy)-2,3,4,5-tetrahydro-1,5-benzothiazepine The title compound was synthesised from 1,1-dioxo-3-butyl-3-ethyl-5-phenyl-7-methylthio-8-(N-{(R)-1'-phenyl-1'-[N-(1"-methoxycarbonyl-1"-phenylmethyl)carbamoyl]methyl}carbamoylmethoxy)-2,3,4,5-tetrahydro-1,5-benzothiazepine (Method 73) by the procedure of Example 52. NMR (500 MHz) 0.76–0.84 (m, 6H), 1.05–1.73 (m, 8H), 2.14 (s, 3H), 3.16 (m, 2H), 3.74 (m, 2H), 4.48 (m, 2H), 5.53 (d, 2H), 5.96 (d, 1H), 6.63 (s, 1H), 6.97–7.48 (m, 13H), 7.86 (m, 1H), 8.17 (m, 1H).

Example 54

1,1-Dioxo-3-ethyl-3-butyl-5-phenyl-7-methylthio-8-{1-[N-((R)-α-carboxybenzyl)carbamoyl]ethoxy}-2,3,4,5-tetrahydro-1,5-benzothiazepine To a solution of 1,1-dioxo-3-butyl-3ethyl-5-phenyl-7-bromo-8-{1-[N-((R)-1'-phenyl -1'-carboxymethyl)carbamoyl]ethoxy}-2,3,4,5-tetrahydro-1,5-benzothiazepine (Example 10, 0.050 g, 7.6×10$^{-5}$ mol) in DMF (4 ml) was added sodium thiomethylate (0.021 g, 3.0×10$^{-4}$ mol) and the solution was stirred for 4 hours at ambient temperature. The mixture was concentrated and the residue was partitioned between water and ether. The aqueous phase was extracted two more times with ether and the combined organic extracts were dried (MgSO$_4$), concentrated and purified by HPLC. The title compound was obtained in 0.030 g (63%) as a white solid. NMR (CD$_3$OD) 0.75–0.90 (m, 6H), 1.00–1.30 (m, 4H), 1.40–1.70 (m, 7H), 2.15 (d, 3H), 3.10–3.30 (m, 2H), 3.55–3.95 (m, 2H), 4.80–4.95 (m, 2H), 5.30 (d, 1H), 6.70–7.50 (m, 12H); m/z 625.3.

Example 55

1,1-Dioxo-3-ethyl-3-butyl-5-phenyl-7-methylthio-8-{α-[N-((R)-α-carboxybenzyl)carbamoyl]benzyloxy}-2,3,4,5-tetrahydro-1,5-benzothiazepine To a solution of 1,1-dioxo-3-ethyl-3-butyl-5-phenyl-7-methylthio-8-{α-[N-((R)-α-carboxybenzyl)carbamoyl]benzyloxy}-2,3,4,5-tetrahydro-1,5-benzothiazepine (Example 11; 0.018 g, 2.5×10$^{-5}$ mol) in DMF (3 ml) was added sodium thiomethylate (0.007 g, 1.0×10$^{-4}$ mol) and the solution was stirred for 4 hours at ambient temperature. The mixture was concentrated and the residue was partitioned between water and ether. The aqueous phase was extracted two more times with ether and the combined organic extracts were dried (MgSO$_4$), concentrated and purified by HPLC. The title compound was obtained in 0.015 g (89%) as a white solid. NMR (CD$_3$OD) 0.70–0.85 (m, 6H), 1.00–1.25 (m, 4H), 1.35–1.65 (m, 4H), 2.20 (d, 3H), 3.10–3.20 (m, 2H), 3.50–3.85 (m, 2H), 5.30 (d, 1H), 5.80 (d, 1H), 6.70 (s, 1H), 6.90–7.65 (m, 16H).

Example 56

1,1-Dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine 2-{[(2R)-2-Amino-2-(4-hydroxyphenyl)ethanoyl]amino}ethanesulphonic acid (Method 80; 32.5 mg, 0.119 mmol) was mixed with DMF (4 ml) and N-methylmorpholine (30 µl, 0.272 mmol). A clear solution was obtained and 1,1-dioxo-3,3-dibutyl-5-phenyl-7-methylthio-8-carboxymethoxy-2,3,4,5-tetrahydro-1,5-benzothiazepine (Method 22; 50 mg, 0.099 mmol) and TBTU (38 mg, 0.119 mmol) were added successively. The reaction was stirred at ambient temperature for 30 min and the DMF was removed. The crude product was purified by preparative HPLC using an MeCN/ammonium acetate buffer (1:1). Lyophilisation gave 55 mg of the title compound (71%). NMR (500 MHz, MeOD) 0.78–0.86 (m, 6H), 1.0–1.3 (m, 8H), 1.4–1.6 (m, 4H), 2.15 (s, 3H), 2.85–3.00 (m, 2H), 3.25 (s, 2H), 3.55–3.68 (m, 2H), 3.75 (brs, 2H), 4.65 (ABq, 2H), 5.36 (s, 1H), 6.70 (s, 1H), 6.75 (d, 2H), 6.98 (t, 1H), 7.12 (d, 2H), 7.22 (d, 2H) 7.28 (t, 2H), 7.4 (s, 1H); m/z 762.

Examples 57–58

The following compounds were synthesised by the procedure of Example 56 using the appropriate starting material except that the reaction was left to proceed for 64 hours (Example 57) or 2 hours (Example 58) and the product was purified by preparative HPLC using an MeCN/ammonium acetate buffer gradient (45/55 to 60/40) as eluent.

at ambient temperature for 5 min TBTU (45.6 mg, 0.142 mmol) was added followed by stirring for 2 hours. The reaction mixture was filtered through a short column and concentrated. The crude ester was dissolved in THF (1.5 ml) and water (1.5 ml) and NaOH (1 M, 0.20 mmol) was added. After stirring at ambient temperature for 1 hour the reaction was quenched with 1 M HCl. The reaction mixture was

| Ex | Compound | NMR(CD$_3$OD) and m/z | SM |
|---|---|---|---|
| 57 | 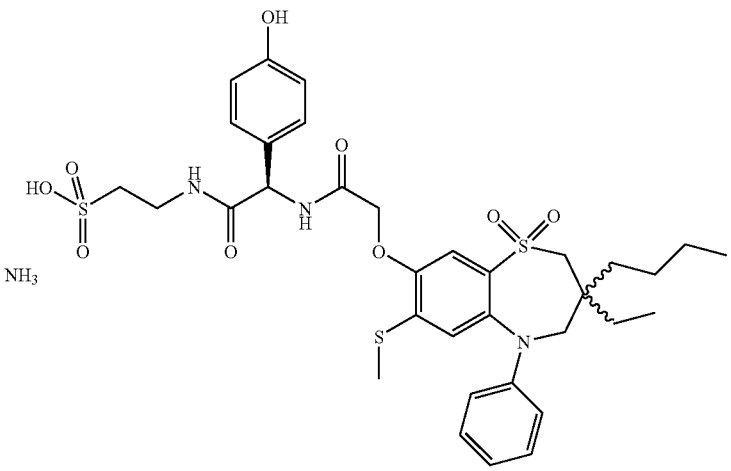<br>Enantiomer 1 | 0.75–0.84(m, 6H) 1.00–1.27(m, 4H), 1.37–1.64(m, 4H) 2.14(s, 3H), 2.86–3.00(m, 2H), 3.22(s, 2H), 3.53–3.68(m, 2H), 3.85 brd, 2H), 4.68(ABq, 2H), 5.35(s, 1H), 6.70(s, 1H), 6.75(d, 2H), 6.95(t, 1H), 7.08(d, 2H), 7.20–7.29(m, 4H), 7.37(s, 1H); m/z 751 (M+NH$_4^+$) | Meth 23 |
| 58 | 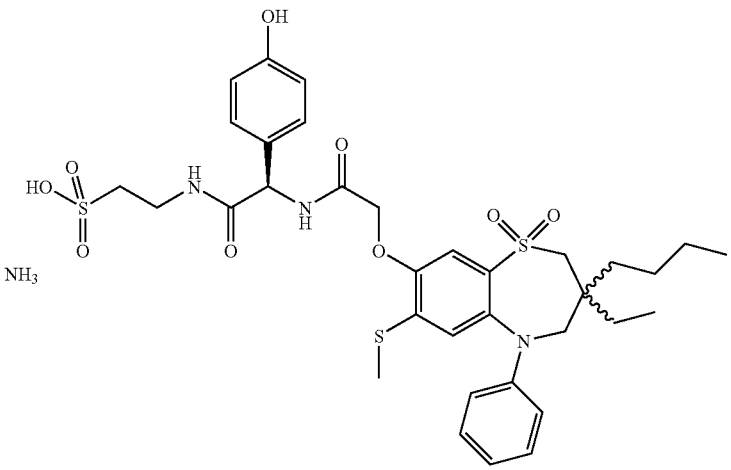<br>Enantiomer 2 | 0.77–0.85(m, 6H)1.06–1.27(m, 4H), 1.40–1.62(m, 4H) 2.17(s, 3H), 2.87–3.00(m, 2H), 3.24(s, 2H), 3.56–3.68(m, 2H), 3.75(brd, 2H), 3.56–3.68(m, 2H), 3.75(brd, 2H), 4.71(ABq, 2H), 5.37(s, 1H), 6.72(s, 1H), 6.77(d, 2H), 6.97(t, 1H), 7.10(d, 2H), 7.23(d, 2H), 7.28(t, 2H), 7.40(s, 1H); m/z 751 (M+NH$_4^+$) | Meth 24 |

Example 59

1,1-Dioxo-3-butyl-3-ethyl-5-phenyl-7-methylthio-8-(N-{(R)-α-[N'-(2-carboxyethyl) carbamoyl] benzyl}carbamoylmethoxy)-2,3,4,5-tetrahydro-1,5-benzothiazepine 1,1-Dioxo-3-butyl-3-ethyl-5-phenyl-7-methylthio-8-[N-((R)-α-carboxybenzyl) carbamoylmethoxy]-2,3,4,5-tetrahydro-1,5-benzothiazepine (Example 38; 66.8 mg, 0.109 mmol) and β-alanine ethylester hydrochloride (23.0 mg, 0.15 mmol) was dissolved in DCM (2.5 ml) and N-methyl morpholine (0.07 ml, 0.64 mmol) was added. After stirring diluted with water (10 ml) and extracted with DCM (3×5 ml). The organic layers was concentrated and purified with preparative HPLC to give the title compound (60 mg, 81%). NMR (300 MHz) 0.80 (m, 6H), 1.00–1.70 (m, 8H), 2.17 (s, 3H), 2.48 (m, 2H), 3.17 (ABq, 2H), 3.35 (m, 1H), 3.57 (m, 1H), 3.70 (m, 2H), 4.62 (ABq, 2H), 5.77 (d, 1H), 6.64 (s, 1H), 6.98 (t, 1H), 7.06 (d, 2H), 7.28 (m, 4H), 7.42 (m, 3H), 7.56 (m, 1H), 8.10 (m, 1H).

Examples 60–63

The following compounds were synthesised by the procedure of Example 59 using the appropriate starting material.

| Ex | Compound | NMR | SM |
|---|---|---|---|
| 60 | | 0.81(m, 6H), 1.00–1.95(m, 10H), 2.22(s, 3H), 3.37(m, 2H), 3.18 (ABq, 2H), 3.48(m, 2H), 3.75(m, 2H), 4.66(q, 2H), 5.75(d, 1H), 6.67 (s, 1H), 7.00(t, 1H), 7.09(m, 2H), 7.20(m, 1H), 7.30(m, 4H), 7.44(m, 2H), 8.25(m, 1H) | Ex 38 |
| 61 | | (300MHz, DMSO-$d_6$) 0.74(m, 6H), 0.95–1.50(m, 12H), 2.16(s, 3H), 2.28(t, 2H), 3.24(m, 2H), 4.74(q, 2H), 5.33(d, 1H), 6.69(m, 2H), 6.85 (t, 1H), 6.99(m, 2H), 7.16(m, 4H), 8.33–8.45(m, 2H) | Ex 2 |
| 62 | | (300MHz) 0.81(m, 6H), 1.00–1.74 (m, 14H), 2.22(s, 3H), 2.31(m, 2H), 3.10–3.35(m, 4H), 3.73(m, 2H), 4.62(ABq, 2H), 5.64(d, 1H), 6.39 (brs, 1H), 6.67(s, 1H), 6.96–7.10(m, 3H), 7.25–7.48(m, 7H), 8.21(d, 1H) | Ex 38 |
| 63 | | 0.81(m, 6H), 1.03–1.55(m, 12H), 2.19(s, 3H), 2.55(m, 2H), 3.18(m, 2H), 3.46(m, 1H), 3.58(m, 1H), 3.74(m, 2H), 4.64(ABq, 2H), 5.80 (m, 1H), 6.64(s, 1H), 7.01(t, 1H), 7.08(d, 2H), 7.30(m, 5H), 7.44(m, 3H), 8.11(m, 1H) | Ex 1 |

Example 64

1,1-Dioxo-3-butyl-3-ethyl-5-phenyl-7-methylthio-8-[N-((R)-α-carboxy-4-methoxybenzyl) carbamoylmethoxy]-2,3,4,5-tetrahydro-1,5-benzothiazepine 1,1-Dioxo-3-butyl-3-ethyl-5-phenyl-7-methylthio-8-{N-[(R)-α-(t-butoxycarbonyl)-4-hydroxybenzyl]carbamoylmethoxy}-2,3,4,5-tetrahydro-1,5-benzothiazepine (Method 78; 48 mg, 0.070 mmol), bromoethyl(trimetylammoniumbromide) (57 mg, 0.230 mmol), tetrabutylammonium bromide (3 mg, 0.009 mmol) and $Cs_2CO_3$ (71 mg, 0.22 mmol) were added to $CH_3CN$ (1.0 ml) and the reaction mixture was heated at reflux overnight. The solvent was evaporated and the residue was added to water (10 ml), extracted with DCM (3×5 ml) and dried ($MgSO_4$). The crude ester was dissolved in DCM (2.5 ml), TFA (0.3 ml) was added and the reaction mixture was stirred at room temperature overnight. The solvents were evaporated and the crude product was purified with preparative HPLC to give the title compound (23 mg, 51%). NMR (DMSO-$d_6$) 0.74 (m, 6H), 0.94–1.60 (m, 8H), 2.17 (s, 3H) 3.25 (m, 2H), 3.69 (s, 3H), 4.70 (ABq, 2H), 4.95 (brs, 1H), 6.71 (s, 1H), 6.83 (m, 3H), 6.97 (d, 2H), 7.20 (m, 4H), 7.27 (s, 1H), 8.37 (brs, 1H).

Example 65

1,1-Dioxo-3,3-dibutyl-5-phenyl-7-methylthio-8-(N-{(α-[N'-(2-sulhoethyl)carbamoyl]-α-methylbenzyl}carbamoylmethoxy)-2,3,4,5-tetrahydro-1,5-benzothiazepine ammonium salt 1,1-Dioxo-3,3-dibutyl-5-phenyl-7-methylthio-8-[N-(α-carboxy-α-methylbenzyl)carbamoylmethoxy]-2,3,4,5-tetrahydro-1,5-benzothiazepine (Example 18; 27 mg, 0.041 mmol) was dissolved in DCM (2 ml). Taurine tetrabutylammonium salt (45 mg, 0.123 mmol) and TBTU (16 mg, 0.050 mmol) was added successively and the mixture was stirred for 5 hours at ambient temperature. The solvent was evaporated and the product was purified by preparative HPLC using an MeCN/ammonium acetate buffer (50/50) as eluent. Lyophilisation gave the title compound in 62% yield (20 mg). NMR showed 16% of the product to remain as a tetrabutylammonium salt. NMR (500 MHz) 0.75–0.9 (m, 6H), 1.0–1.3 (m, 8H), 1.3–1.6 (m, 4H), 1.95 (s, 3H), 2.1 (s, 3H), 2.9 (brs, 2H), 3.05 (brs, 2H), 3.55 (ABd, 2H), 3.75 (brs, 2H), 4.55 (ABq, 2H), 6.6 (s, 1H), 6.9–7.6 (m, 12H), 8.2–8.3 (brs, 1H); m/z 777 (M+$NH_4^+$).

Examples 66–67

The following compounds were synthesised by the procedure of Example 65 using the appropriate starting material.

| Ex | Compound | NMR($CD_3OD$) and M/z | SM |
|---|---|---|---|
| 66 | [structure with $NH_4^+$ taurine amide, phenyl, benzothiazepine core with dibutyl, methylthio, N-phenyl] | 777(M+$NH_4^+$) | Ex 1 |
| 67 | [structure with $NBu^+$ taurine amide, phenyl, benzothiazepine core with butyl/ethyl, methylthio, N-phenyl] | 0.75–0.85(m, 6H), 1.02(t, 12H), 1.05–1.3(m, 4H), 1.3–1.7(m, 20H), 2.17(s, 3H), 2.85–2.99(m, 2H), 3.19–3.26(m, 10H), 3.52–3.92(m, 4H), 4.71(ABq, 2H), 5.47(s, 1H), 6.72(s, 1H), 6.96(t, 1H), 7.09(brd, 2H), 7.23–7.44(m, 8H); m/z 735.2 (M+$NH_4^+$) | Ex 25 |

Example 68

1,1-Dioxo-3,3-dibutyl-5-phenyl-7-methylthio-8-(N-{α-[N'-(carboxymethyl)carbamoyl]-α-methylbenzyl}carbamoylmethoxy)-2,3,4,5-tetrahydro-1,5-benzothiazepine 1,1-Dioxo-3,3-dibutyl-5-phenyl-7-methylthio-8-(N-{α-[N'-(methoxycarbonylmethyl)carbamoyl]-α-methylbenzyl}carbamoylmethoxy)-2,3,4,5-tetrahydro-1,5-benzothiazepine (Method 44; 20 mg, 0.028 mmol) was dissolved in 2.5 ml of a THF/water mixture (4/1). LiOH (2 mg, 0.084 mmol) was added and the mixture was stirred for 1 hour at ambient temperature. The title compound was purified with preparative HPLC using an MeCN/ammonium acetate buffer (50/50) as eluent. The MeCN was evaporated and the remaining buffer was acidified with acetic acid. Lyophilisation gave 10 mg product (51%). NMR 0.7–0.9 (m, 6H), 1.0–1.35 (m, 8H), 1.35–1.6 (m, 4H), 2.0 (s, 3H), 2.2 (s, 3H), 3.2 (brs, 2H), 3.65–3.85 (brs, 2H), 3.9–4.1 (d, 2H), 4.5–4.7 (ABq, 2H), 6.6 (s, 1H), 6.8 (brs, 1H), 6.9–7.5 (m, 11H), 8.1 (s, 1H); m/z 727 (M+NH$_4^+$).

Example 69

1,1-Dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine 1,1-Dioxo-3,3-dibutyl-5-phenyl-7-methylthio-8-{N-[α-carboxy-2-fluorobenzyl]carbamoylmethoxy}-2,3,4,5-tetrahydro-1,5-benzothiazepine (Example 15; 20 mg, 0.030 mmol), taurine tetrabutylammonium salt (20 mg, 0.054 mmol) and DIPEA (25 mg, 0.19 mmol) was dissolved in DMF (0.4 ml). TBTU (15 mg, 0.047 mmol) was added and the mixture was stirred for 30 min at room temperature. The product was separated from the reaction mixture by preparative HPLC using MeCN/ammonium acetate buffer (50:50) as eluent. 7 mg (29%) of the title compound was obtained. M/z=764.5.

Example 70

1,1-Dioxo-3,3-dibutyl-5-phenyl-7-methylthio-8-(N-(R)-{α-[(N'-(R)-{α-[N''-(carboxymethyl) carbamoyl]benzyl}carbamoyl)methylcarbamoyl] benzyl}carbamoylmethoxy)-2,3,4,5-tetrahydro-1,5-benzothiazepine 1,1-Dioxo-3,3-dibutyl-5-phenyl-7-methylthio-8-(N-{(R)-1'-phenyl-1'-[N'-(carboxymethyl)carbamoyl] methyl}carbamoylmethoxy)-2,3,4,5-tetrahydro-1,5-benzothiazepine (Example 43; 35 mg, 0.050 mmol) and (R)-α-[N-(t-butoxycarbonylmethyl) carbamoyl]benzylamine (Method 86; 20 mg, 0.076 mmol) were dissolved in DCM (2 ml) and 2,6-lutidine (0.03 ml, 0.26 mmol) was added. After stirring at ambient temperature for 5 min, TBTU (20 mg, 0.062 mmol) was added and stirring was continued for 3 hours. The reaction mixture was filtered through a column using DCM: EtOAc; 3:1 as eluent. The t-butyl ester was then dissolved in DCM (6 ml) and TFA (1 ml) was added. After stirring at ambient temperature overnight the solvents were evaporated. Toluene was added and evaporated twice. No further purification was necessary to give the title compound (40 mg, 93%). NMR (500 MHz, DMSO-d$_6$) 0.75 (m, 6H), 0.95–1.50 (m, 12H), 2.16 (s, 3H), 3.25 (m, 2H), 3.75 (m, 2H), 3.90 (dd, 1H), 4.73/4.84 (ABq, 2H), 5.54 (m, 2H), 5.58 (d, 1H), 6.68 (s, 1H), 6.85 (t, 1H), 6.99 (d, 2H), 7.18–7.46 (m, 13H), 8.51–8.73 (m, 4H).

Example 71

1,1-Dioxo-3,3-dibutyl-5-phenyl-7-methylthio-8-[N-(S)-(α-carboxy-4-hydroxybenzyl)carbamoylmethoxy]-2,3,4,5-tetrahydro-1,5-benzothiazepine 1,1-Dioxo-3,3-dibutyl-5-phenyl-7-methylthio-8-carboxymethoxy-2,3,4,5-tetrahydro-1,5-benzothiazepine (Method 22; 61 mg, 0.12 mmol) and methyl(2S)-amino(4-hydroxyphenyl)acetate hydrochloride (31 mg, 0.14 mmol) were dissolved in DCM (4 ml) and 2,6-lutidine (0.04 ml, 0.34 mmol) was added. After stirring at room temperature for 5 min TBTU (3 mg, 0.17 mmol) was added and stirring was continued for 2 hours. The reaction mixture was filtered through a short column. The crude methyl ester was dissolved in THF (1.5 ml) and water (1.0 ml) and NaOH (aq., 1 M, 0.39 mmol) was added. The reaction mixture was stirred at room temperature for 8 hours, quenched with HCl (1 M) and extracted with DCM (3×5 ml). The collected organic layers were concentrated and purified with preparative HPLC using MeCN/ammonium acetate buffer (50:50) to give the title compound (57 mg, 72%). NMR (500 MHz, CD$_3$OD) 0.81 (m, 6H), 1.05–1.26 (m, 8H), 1.40–1.55 (m, 4H), 2.17 (s, 3H), 3.24 (brs, 2H), 3.74 (brs, 1H), 4.66 (ABq, 2H), 6.70–6.75 (m, 3H), 6.99 (t, 1H), 7.11 (d, 2H), 7.22–7.30 (m, 4H), 7.40 (s, 1H).

Example 72

1,1-Dioxo-3,3-dibutyl-5-phenyl-7-methylthio-8-(N-(S)-{α-[N'-(2-sulphoethyl)carbamoyl]-4-hydroxybenzyl}carbamoylmethoxy)-2,3,4,5-tetrahydro-1,5-benzothiazepine ammonium salt 1,1-Dioxo-3,3-dibutyl-5-phenyl-7-methylthio-8-[N-(S)-(α-carboxy-4-hydroxybenzyl)carbamoylmethoxy]-2,3,4,5-tetrahydro-1,5-benzothiazepine (Example 71; 31 mg, 0.047 mmol) and tetrabutylammonium taurine (57 mg, 0.155 mmol) were dissolved in DCM (2 ml). After stirring at room temperature for 5 min TBTU (24 mg, 0.075 mmol) was added and stirring was continued for 6 hours. The solvent was evaporated and the residue was purified with preparative HPLC (twice to remove all tetrabutylammonium salt) using MeCN/ammonium acetate buffer to give the title compound 6 mg (16%). M/z 762.2.

Example 73 and Example 74

1,1-Dioxo-3-(R/S)-3-butyl-3-ethyl-5-phenyl-7-methylthio-8-(N-(R)-{α-[N'-(R)-(2-imidazol-5-yl-1-carboxyethyl)carbamoyl]benzyl}carbamoylmethoxy)-2,3,4,5-tetrahydro-1,5-benzothiazepine 1,1-Dioxo-3-butyl-3-ethyl-5-phenyl-7-methylthio-8-[N-((R)-1'-phenyl-1'-carboxymethyl)carbamoylmethoxy]-2,3,4,5-tetrahydro-1,5-benzothiazepine (Example 38; 56.4 mg, 0.092 mmol) and methyl D-histidinate dihydrochloride (25.2 mg, 0.104 mmol) were added to DCM (3 ml). N-methyl morpholine (0.05 ml, 0.41 mmol) was added followed by TBTU (40 mg, 0.12 mmol). The reaction mixture was stirred at 4° C. for 1 hour 30 min and at room temperature for 3 hours. More TBTU (15 mg, 0.047 mmol) and DIPEA (0.025 ml, 0.14 mmol) were added and the reaction mixture was stirred at room temperature, for another 30 min. The solvent was evaporated and the residue was filtered through a short column with MeOH as eluent. The crude methyl ester was dissolved in THF (1.0 ml) and water (1.0 ml) and NaOH (aq., 1 M, 0.15 mmol) was added. The reaction mixture was stirred at room temperature for 2 hours and was quenched with HCl (1 M). The solvents were evaporated the residue was purified with preparative HPLC using MeCN/ammonium acetate buffer. The compound eluted as two peaks, assumed to be the two diastereomers. First peak (10 mg, 14%). Second peak (16.8 mg, 24%). First peak: NMR (DMSO-$d_6$) 0.74 (m, 6H), 0.95–1.60 (m, 8H) 2.17 (s, 3H), 2.82 (m, 2H), 3.23 (m, 2H), 4.27 (m, 1H), 4.80 (ABq, 2H), 5.60 (d, 1H), 6.55 (brs, 1H), 6.70 (s, 1H), 6.84 (t, 1H), 6.96 (d, 2H), 7.14–7.28 (m, 6H), 7.33 (s, 1H), 7.44 (brs, 1H), 8.54 (d, 1H), 8.60 (brs, 1H); m/z 748.4. Second peak: NMR (DMSO-$d_6$) 0.74 (m, 6H), 0.95–1.60 (m, 8H), 2.17 (s, 3H), 2.92 (dABq, 2H), 3.23 (m, 2H), 4.41 (m, 1H), 4.79 (ABq, 2H), 5.60 (d, 1H), 6.70 (s, 1H), 6.78 (s, 1H), 6.84 (t, 1H), 6.96 (d, 2H), 7.16–7.34 (m, 6H), 7.40 (m, 2H), 7.55 (s, 1H), 8.55 (d, 1H), 8.71 (d, 1H); m/z 748.4.

Example 75

1,1-Dioxo-3,3-dibutyl-5-(4-t-butylphenyl)-7-methylthio-8-(N-{(R)-α-[N'-(carboxymethyl)carbamoyl]benzyl}carbamoylmethoxy)-2,3,4,5-tetrahydro-1,5-benzothiazepine The title compound was isolated as a byproduct in synthesis of 1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine (Example 43). Approximately 1 g of this compound was purified with preparative HPLC (MeCN/ammonium acetate buffer (50:50)) to give the title compound (32 mg). NMR (500 MHz, DMSO-$d_6$) 0.73 (m, 6H), 0.90–1.40 (m, 12H), 1.24 (s, 9H), 2.16 (s, 3H), 3.23 (m, 2H), 3.65/3.75 (dABq, 2H), 4.72/4.82 (ABq, 2H), 5.60 (d, 1H), 6.65 (s, 1H), 6.97 (d, 2H), 7.23–7.35 (m, 6H), 7.45 (d, 2H), 8.58 (d, 1H), 8.62 (t, 1H).

Example 76

1,1-Dioxo-3-butyl-3-ethyl-5-phenyl-7-(N-((R)-α-carboxybenzyl methylthio)-8-methoxy-2,3,4,5-tetrahydro-1,5-benzothiazepine 1,1-Dioxo-3-butyl-3-ethyl-5-phenyl-7-carboxymethylthio-8-methoxy-2,3,4,5-tetrahydro-1,5-benzothiazepine (Method 81; 38 mg, 0.080 mmol) and D-phenylglycine methyl ester hydrochloride (24 mg, 0.12 mmol) were dissolved in DCM (2 ml) and N-methyl morpholine (0.05 ml, 0.42 mmol) was added. After stirring at room temperature for 5 min TBTU (44 mg, 0.14 mmol) was added and stirring was continued for 2 hours. The reaction mixture was filtered through a short column. The resulting product was dissolved in THF (1 ml) and water (1 ml) and NaOH (aq., 0.2 ml, 1 M) was added and the reaction mixture was stirred at room temperature for 2 hours. The reaction was quenched with HCl (1 M), diluted with water (10 ml) and extracted with DCM (3×3 ml). Purification with preparative HPLC yielded the title compound (40 mg, 82%). NMR (DMSO-$d_6$) 0.75 (m, 6H), 0.96–1.60 (m, 8H), 3.22 (m, 2H), 3.56 (ABq, 2H), 3.89 (s, 3H), 4.81 (d, 1H), 6.78 (d, 2H), 6.83 (d, 2H), 6.89 (s, 1H), 7.11–7.23 (m, 7H), 7.31 (s, 1H), 8.37 (m, 1H).

Example 77

1,1-Dioxo-3-butyl-3-ethyl-5-phenyl-7-carboxymethylthio-8-[N-α-carboxybenzyl)carbamoylmethoxy]-2,3,4,5-tetrahydro-1,5-benzothiazepine 1,1-Dioxo-3-butyl-3-ethyl-5-phenyl-7-ethoxycarbonylmethylthio-8-carboxymethoxy-2,3,4,5-tetrahydro-1,5-benzothiazepine (Method 82; 21 mg, 0.038 mmol) and phenylglycine methyl ester hydrochloride (12 mg, 0.061 mmol) were dissolved in DCM (1.5 ml) and N-methyl morpholine (0.02 ml, 0.19 mmol) was added. After stirring at ambient temperature for 5 min TBTU (18 mg, 0.056 mmol) was added and stirring was continued for 2 hours. The reaction mixture was filtered through a short column. The crude diester was dissolved in THF (1 ml) and water (1 ml) and NaOH (aq., 0.1 ml, 1 M) was added. The reaction mixture was stirred at ambient temperature for 2 hours, quenched with HCl (1 M), diluted with water (10 ml) and extracted with DCM (3×3 ml). The collected organic layers were concentrated and purified with preparative HPLC using MeCN/ammonium acetate buffer (30:70→40:60) to give the title compound (20 mg, 80%). NMR (CD$_3$OD) 0.80 (m, 6H), 1.03–1.26 (m, 4H), 1.38–1.65 (m, 4H), 1.96 (s, 3H), 3.20 (s, 2H), 3.44 (s, 2H), 3.67 (brs, 1H), 3.76 (brs, 1H), 4.67 (ABq, 2H), 5.29 (s, 1H), 6.89 (s, 1H), 6.92 (t, 1H), 7.05 (d, 2H), 7.19–7.32 (m, 5H), 7.41 (s, 1H), 7.45 (d, 2H).

Example 78

1,1-Dioxo-3,3-dibutyl-5-phenyl-7-methylthio-8-[N-(R)-(α-{N'-[(R)-N''-(2-hydroxy-1-carboxyethyl)carbamoylmethyl]carbamoyl}benzyl)carbamoylmethoxy]-2,3,4,5-tetrahydro-1,5-benzothiazepine 1,1-Dioxo-3,3-dibutyl-5-phenyl-7-methylthio-8-(N-{R)-1'-phenyl-1'-[N'-(carboxymethyl)carbamoyl]methyl}carbamoylmethoxy)-2,3,4,5-tetrahydro-1,5-benzothiazepine (Example 43; 50 mg, 0.072 mmol), tert-butyl o-(tert-butyl)-D-serinate hydrochloride (22 mg, 0.087 mmol) and N-methylmorpholine (40 mg, 0.40 mmol) were dissolved in DCM (1 ml). TBTU (29 mg, 0.090 mmol) was added and the mixture was stirred for 1 hour at room-temperature. The reaction mixture was evaporated and the residue was filtered through a short column (DCM: EtOAc, 1:4). The substance obtained (ca. 60 mg) was dissolved in DCM (1 ml). TFA (0.59 g, 5.2 mmol) was added and the mixture was stirred for 2 hours at room temperature. The solvent was evaporated and the residue was purified by preparative HPLC using MeCN/ammonium acetate buffer (50:50) as eluent. 38 mg (72%) of the title compound was obtained. NMR (300 MHz, DMSO-$d_6$) 0.7–0.8 (m, 6H), 0.9–1.5 (m, 12H), 2.2 (s, 3H), 3.2–3.9 (m, 10H), 4.2 (brs, 1H), 4.8 (ABq, 2H), 5.6 (d, 1H), 6.7 (s, 1H), 6.8–7.5 (m, 11H), 8.0 (d, 1H), 8.6 (d, 1H), 8.7 (t, 1H).

Example 79

1,1-Dioxo-3,3-dibutyl-5-phenyl-7-methylthio-8-[N-(R)-(α-{N'-[(S)-N''-(2-hydroxy-1-carboxyethyl)carbamoylmethyl]carbamoyl}benzyl)carbamoylmethoxy]-2,3,4,5-tetrahydro-1,5-benzothiazepine 1,1-Dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine (Example 43; 50 mg, 0.072 mmol), tert-butyl O-(tert-butyl)-L-serinate hydrochloride (22 mg, 0.087 mmol) and N-methylmorpholine (40 mg, 0.40 mmol) were dissolved in DCM (1 ml). TBTU (29 mg, 0.090 mmol) was added and the mixture was stirred for 1 h at room temperature. The reaction mixture was evaporated and the residue was filtered through a short column (DCM: EtOAc, 1:4). The substance obtained (ca. 60 mg) was dissolved in DCM (1 ml). TFA (0.44 g, 3.9 mmol) was added and the mixture was stirred for 18 hours at room temperature. The solvent was evaporated and the residue was purified by preparative HPLC using MeCN/ammonium acetate buffer (50:50) as eluent. 33 mg (63%) of the title compound was obtained. NMR (300 MHz, DMSO-$d_6$) 0.7–0.8 (m, 6M), 0.9–1.5 (m, 12H), 2.2 (s; 3H), 3.2–3.9 (m, 10H); 4.2 (m, 1H), 4.8 (ABq, 2H), 5.6 (d, 1H), 6.7 (s, 1H), 6.8–7.5 (m, 11H), 7.9 (d, 1H), 8.6 (d, 1H), 8.7 (t, 1H).

Example 80

1,1-Dioxo-3-butyl-3-ethyl-5-phenyl-7-methylthio-8-(N-{(R)-α-[N'-(1,1-dicarboxymethyl)carbamoyl]benzyl}carbamoylmethoxy)-2,3,4,5-tetrahydro-1,5-benzothiazepine 1,1-Dioxo-3-butyl-3-ethyl-5-phenyl-7-methylthio-8-[N-((R)-α-carboxybenzyl)carbamoylmethoxy]-2,3,4,5-tetrahydro-1,5-benzothiazepine (Example 38; 50 mg, 0.082 mmol), dimethylaminomalonate (60 mg, 0.13 mmol) and N-methylmorpholine (55 μl, 0.5 mmol) were dissolved in DCM (3 ml), TBTU (42 mg, 0.13 mmol) was added and the mixture was stirred for 15 mins. The solvent was evaporated under reduced pressure. The residue was dissolved in ethanol (95%) (2 ml) and a solution of NaOH (80 mg, 2 mmol) in water (80 μl) was added. The reaction mixture was stirred for 4 hours. The mixture was neutralized with acetic acid. The solvent was evaporated under reduced pressure and the residue was purified by preparative HPLC using-MeCN/ammonium acetate buffer (40:60) as eluent. The collected fractions were lyophilised to obtain 4 mg (7%) of the title compound. NMR (300 MHz, CD$_3$OD) 0.75–0.9 (m, 6H), 1.0–1.3 (m, 4H), 1.4–1.65 (m, 4H), 2.15 (s, 3H), 3.25 (s, 2H), 3.7 (brs, 2H), 4.65–4.8 (m, 2H), 5.75 (s, 1H), 6.75 (s, 1H), 6.9–7.55 (m, 11H).

Examples 81–87

The following compounds were synthesised by the procedure of Example 80 using the appropriate starting material except that 2,6-lutedine was used instead of N-methylmorpholine and the ration of eluent was MeCN/ammonium acetate buffer (45:55). Reaction time at each stage varied slightly.

| Ex | Compound | NMR(300MHz, CD$_3$OD) | SM |
|---|---|---|---|
| 81 | | (500MHz) 0.8–0.95(m, 6H), 1.05–1.35(m, 4H), 1.4–1.7(m, 4H), 2.2(s, 3H), 3.25(s, 2H), 3.7–3.9(m, 4H), 4.4–4.45(m, 1H), 4.7–4.8(m, 2H), 5.7(s, 1H), 6.75(s, 1H), 6.95–7.6(m, 11H) | Ex 38 |
| 82 | | 0.75–0.9(m, 6H), 1.05–1.3(m, 4H), 1.4–1.6(m, 4H), 2.15(s, 3H), 3.25(s, 2H), 3.7–3.95(m, 4H), 4.25–4.3(m, 1H), 4.75(ABq, 2H), 5.65(s, 1H), 6.75(s, 1H), 7.95–7.55(m, 11H) | Ex 38 |

| Ex | Compound | NMR(300MHz, CD$_3$OD) | SM |
|---|---|---|---|
| 83 | | 0.75–0.9(m, 6H), 1.05–1.35(m, 8H), 1.4–1.6(m, 4H), 2.15(s, 3H), 3.25(s, 2H), 3.7–3.9(m, 4H), 4.35–4.45(m, 1H), 4.7(ABq, 2H), 5.7(s, 1H), 6.75(s, 1H), 6.95–7.55(m, 11H) | Ex 1 |
| 84[1] | | 0.75–0.9(m, 6H), 1.05–1.3(m, 8H), 1.4–1.6(m, 4H), 2.15(s, 3H), 3.25(s, 2H), 3.7–3.9(m, 4H), 3.3–3.4(m, 1H), 4.7(ABq, 2H), 5.65(s, 1H), 6.7(s, 1H), 6.95–7.55(m, 11H) | Ex 1 |
| 85[2] | | 0.75–0.9(m, 6H), 1.05–1.3(m, 8H), 1.4–1.6(m, 4H), 3.25(s, 3H), 3.6–3.9(m, 6H), 4.3–4.5(m, 2H), 4.7(ABq, 2H), 5.65(s, 1H), 6.7(s, 1H), 6.95–7.5(m, 11H) | Ex 83 |
| 86[3] | | 0.75–0.9(m, 6H), 1.05–1.3(m, 8H), 1.4–1.6(m, 4H), 2.15(s, 3H), 3.25(s, 2H), 3.6–3.9(m, 6H), 4.35–4.5(m, 2H), 4.7(ABq, 2H), 5.6(s, 1H), 6.7(s, 1H), 6.95–7.55(m, 11H) | Ex 83 |

| Ex | Compound | NMR(300MHz, CD₃OD) | SM |
|---|---|---|---|
| 87[4] | (structure) | 0.75–0.9(m, 6H), 1.05–1.3(m, 8H), 1.4–1.6(m, 4H), 2.2(d, 3H), 3.15–3.35(m, 5H), 3.5–3.85(4H), 4.4–4.5 (m, 1H), 4.6–4.7(m, 2H), 5.6(s, 1H), 6.7(s, 1H), 6.95–7.55(m, 11H) | Ex 1 |

[1]Eluent ratio (55:45);
[2]Eluent ratio - variable gradient;
[3]Eluent ratio (50:50);
[4]Eluent ratio (60:40)

Example 88

1,1-Dioxo-3,3-dibutyl-5-phenyl-7-methylthio-8-[N-(S)-(α-carboxybenzyl)carbamoylmethoxy]-2,3,4,5-tetrahydro-1,5-benzothiazepine 1,1-Dioxo-3,3-dibutyl-5-phenyl-7-methylthio-8-[N-(S)-(α-methoxycarbonylbenzyl)carbamoylmethoxy]-2,3,4,5-tetrahydro-1,5-benzothiazepine (Method 87; 55.2 mg, 0.064 mmol) was dissolved in THF (2 ml) and 0.5 ml water. LiOH (3.1 mg, 0.127 mmol) was added and the mixture was stirred for 1 hour. Water (1 ml) was added and the mixture was acidified with 0.1M HCl and extracted with DCM (3×2 ml). The DCM phase was dried with and concentrated. The solid product was co-evaporated with diethyl ether and dissolved in HPLC grade water. Lyophilisation gave the title compound as a white solid in 68% yield (28 mg). NMR 0.77–0.85 (m, 6H), 1.03–1.25 (m, 8H), 1.34–1.57 (m, 4H), 2.16 (s, 3H), 3.18 (brs, 2H), 3.75 (brs, 2H), 4.65 (ABq, 2H), 5.7 (d, 1H), 6.63 (s, 1H), 7.0 (t, 1H), 7.1 (d, 2H), 7.26–7.48 (m, 8H), 7.85 (d, 1H); m/z 639.

Example 89

1,1-Dioxo-3,3-dibutyl-5-phenyl-7-methylthio-8-[N-{(S)-α-[N'-(carboxymethyl)carbamoyl]benzyl}carbamoylmethoxy]-2,3,4,5-tetrahydro-1,5-benzothiazepine 1,1-Dioxo-3,3-dibutyl-5-phenyl-7-methylthio-8-[N-{(S)-α-[N'-(methoxycarbonylmethyl)carbamoyl]benzyl}carbamoylmethoxy]-2,3,4,5-tetrahydro-1,5-benzothiazepine (Method 88; 19 mg, 0.027 mmol) was hydrolysed by LiOH (1.3 mg, 0.054 mmol) in THF (1 ml) and water (0.3 ml). After 1 hour water (3 ml) was added and the mixture acidified using 0.1M HCl and extracted with DCM (3×3 ml). The organic layer was dried and evaporated yielding 16 mg (82% yield) of the title compound. NMR 0.77–0.85 (m, 6H), 1.0–1.3 (m, 8H), 1.34–1.57 (m, 4H), 2.17 (s, 3H), 3.18 (s, 2H), 3.75 (brs, 2H), 3.9–4.20 (m, 2H), 4.65 (ABq, 2H), 5.87 (m, 1H), 6.63 (s, 1H), 6.98–7.50 (m, 12H), 8.12–8.20 (m, 1H); m/z 696.

Example 90

1,1-Dioxo-3,3-dibutyl-5-phenyl-7-methylthio-8-[N-{(S)-α-[N'-(2-sulphoethyl carbamoyl]benzyl}carbamoylmethoxy]-2,3,4,5-tetrahydro-1,5-benzothiazepine sodium salt 1,1-Dioxo-3,3—dibutyl-5-phenyl-7-methylthio-8-[N-(S)-(α-carboxybenzyl)carbamoylmethoxy]-2,3,4,5-tetrahydro-1,5-benzothiazepine (Example 88; 41 mg, 0.064 mmol) was dissolved in 3 ml DCM. Taurine tetrabutylammonium salt (70 mg, 0.191 mmol) and TBTU (25 mg, 0.078 mmol) were added successively and the mixture was stirred overnight at ambient temperature. The solvent was evaporated and the product was purified by preparative HPLC using an MeCN/ammonium acetate buffer gradient (45/55 to 55/45) as eluent. Lyophilisation of the collected fractions and then ion-exchange chromatography over 4 g Amberlite CG 120, Na⁺-form, gave the title compound in 85% yield (42 mg). NMR 0.7–0.8 (m, 6H), 0.9–1.2 (m, 8H), 1.3–1.5 (m, 4H), 2.0 (s, 3H), 2.9–3.2 (m, 2H+2H), 3.3–3.8 (m, 2H+2H), 4.4–4.7 (m, 2H), 5.6 (m, 1H), 6.57 (s, 1H), 6.9–7.5 (m, 11H), 7.8–8.1 (m, 2H), m/z 746.

Example 91

The following compound was synthesised by the procedure of Example 90 using the appropriate starting material except the product was purified using a buffer gradient of 40/60 to 70/30 and then lyophilised to give the ammonium salt.

| Ex | Compound | NMR(CD₃OD) and m/z | SM |
|---|---|---|---|
| 91 | | 0.76–0.84(m, 6H), 1.03–1.27(m, 8H), 1.38–1.55(m, 4H), 2.15(s, 3H), 2.95(t, 2H), 3.24(s, 2H), 3.58(dt, 2H), 3.75 (brs, 2H), 3.85(ABdd, 2H), 4.72(ABq, 2H), 5.51(s, 1H), 6.70(s, 1H), 6.97(t, 1H), 7.11(d, 2H), 7.25–7.40(m, 6H), 7.46(d, 2H); m/z 803 | Ex 43 |

Example 92

1,1-Dioxo-3-butyl-3-ethyl-5-phenyl-7-[N-{(R)-α-[N'-(carboxymethyl)carbamoyl] benzyl}carbamoylmethoxy]-2,3,4,5-tetrahydro-1,5-benzothiazepine sodium salt 1,1-Dioxo-3-butyl-3-ethyl-5-phenyl-7-carboxymethoxy-2,3,4,5-tetrahydro-1,5-benzothiazepine sodium salt (WO 01/66533; 120 mg, 0.278 mmol) dissolved in DCM (4 ml) was added to a solution of α-[N-(t-butoxycarbonylmethyl) carbamoyl]benzylamine (Method 86; 90%, 150 mg, 0.511 mmol) in DCM (3 ml). 2,6-Dimethylpyridine (65 □l, 0.559 mmol) and TBTU (137 mg, 0.427 mmol) were added and the reaction mixture was stirred at ambient temperature overnight. The solution was filtered over using DCM/EtOAc (8/2) as eluent. The solvent was evaporated. DCM (4 ml) and TFA (0.6 ml) were added and the mixture was stirred overnight. The solvent was evaporated and the crude product was purified by preparative HPLC on a Chromasil C₁₈ column. An MeCN/ammonium acetate buffer gradient (50/50 to 100/0) was used as mobile phase. The MeCN was evaporated and lyophilisation gave the title compound in 36% yield (62 mg). NMR 0.73–0.82 (m, 6H), 1.00–1.23 (m, 4H), 1.30–1.65 (m, 4H), 3.05–3.18 (m, 2H), 3.65 (brs, 2H), 3.75 (ABdd, 2H), 4.46 (ABq, 2H), 5.70 (d, 1H), 6.79–7.24 (m, 10H), 7.36 (d, 2H), 7.46 (d, 1H), 7.83 (d, 1H), 8.00 (brs, 1H); m/z 622.

Example 93–94

The following compounds were synthesised by the procedure of Example 92 using the appropriate starting material except that the HPLC-chromatography was performed on a Chromasil C₈ column and the eluent gradient was 45/55 to 60/40.

| Ex | Compound | NMR(CD₃OD) and m/z | SM |
|---|---|---|---|
| 93 | Enantiomer 1 | 0.75–0.84(m, 6H) 1.00–1.27(m, 4H), 1.38–1.66(m, 4H) 2.15(s, 3H), 3.22(s, 2H), 3.75(brs, 2H), 3.83(ABdd, 2H), 4.69(ABq, 2H), 5.60(s, 1H), 6.71(s, 1H), 6.96(t, 1H), 7.09(d, 2H), 7.23–7.37(m, 5H), 7.39(s, 1H), 7.46(d, 2H); m/z 668 | Meth 23; Meth 86 |
| 94 | Enantiomer 2 | 0.78–0.85(m, 6H) 1.04–1.27(m, 4H), 1.41–1.65(m, 4H), 2.17(s, 3H), 3.24(s, 2H), 3.68(brs, 2H), 3.89(ABdd, 2H), 4.72(ABq, 2H), 5.62(s, 1H), 6.73(s, 1H), 6.97(t, 1H), 7.11(d, 2H), 7.26–7.38(m, 5H), 7.41(s, 1H), 7.48(d, 2H); m/z 668 | Meth 24; Meth 86 |

Example 95

1,1-Dioxo-3-butyl-3-ethyl-5-phenyl-7-methylthio-8-{N-[(R)-α-(N'-{2-[(ethoxy)(methyl)phosphoryl]ethyl}carbamoyl)benzyl]carbamoylmethoxy}-2,3,4,5-tetrahydro-1,5-benzothiazepine To a solution of 2-[(methyl)(ethyl)phosphoryl]ethylamine (Helv. Chim. Acta; GE; 75; 8; 1992; 2545–2552; 16 mg, 0.106 mmol) in DCM (2 ml) was added at 0° C. 1,1-dioxo-3-butyl-3-ethyl-5-phenyl-7-methylthio-8-[N-((R)-1'-phenyl-1'-carboxymethyl)carbamoylmethoxy]-2,3,4,5-tetrahydro-1,5-benzothiazepine (Example 38; 50 mg, 0.082 mmol) DIPEA (42 mg, 0.328 mmol) and TBTU (34 mg, 0.106 mmol) under argon. The reaction mixture was stirred at room temperature for 110 min and then DCM was added and the solution washed with NaHCO₃ (aq, sat) and brine. The organic layer was dried and the solvent evaporated under reduced pressure. The residue purified by chromatography and the product eluted with DCM/methanol (100:5). Yield 43 mg (71%). NMR (500 MHz) 0.78–0.85 (m, 6H), 1.02–1.54 (m, 12H), 1.6–1.75 (br, 1H), 1.8–2.10 (m, 3H), 2.21 (s, 3H), 3.10–3.25 (m, 2H), 3.51–3.84 (m, 4H), 3.9–3.99 (m, 1H), 4.01–4.09 (m, 1H), 4.54–4.69 (dd, 2H), 5.51 (d, 1H), 6.68 (s, 1H), 6.96–7.02 (m, 1H), 7.03–7.18 (m, 3H), 7.25–7.42 (m, 6H), 7.43–7.48 (m, 2H), 8.05–8.15 (m, 1H).

Examples 96–97

The following compounds were synthesised by the procedure of Example 95 using the appropriate starting material.

Example 98

1,1-Dioxo-3-butyl-3-ethyl-5-phenyl-7-methylthio-8-{N-[(R)-α-(N'-{2-[(hydroxy)(methyl)phosphoryl]ethyl}carbamoyl)benzyl]carbamoylmethoxy}-2,3,4,5-tetrahydro-1,5-benzothiazepine To a solution of 1,1-dioxo-3-butyl-3-ethyl-5-phenyl-7-methylthio-8-{N-[(R)-α-(N'-{2-[(ethoxy)(methyl)phosphoryl]ethyl}carbamoyl)benzyl]carbamoylmethoxy}-2,3,4,5-tetrahydro-1,5-benzothiazepine (Example 95; 27 mg, 0.036 mmol) in ethanol (1.5 ml) was added at 0° C. 2 M aqueous NaOH (0.22 ml, 0.44 mmol). The reaction mixture was stirred at room temperature for 24 hours. Acetic acid (0.2 ml) was added. The solvent was evaporated under reduced pressure and the residue was extracted with DCM/water. The DCM layer was separated, washed with brine, dried and evaporated under reduced pressure. Recrystallization of the residue from DCM/ether/petroleum ether gave the title compound 23 mg (89%). NMR (600 MHz) 0.74–0.82 (m, 6H), 1.0–1.70 (m, 11H), 1.90–2.09 (m, 2H), 2.16 (s, 3H), 3.05–3.24 (m, 2H), 3.40–3.85 (m, 4H), 4.50–4.65 (dd, 2H), 5.55 (d, 1H), 6.63 (s, 1H), 6.93–7.07 (m, 3H), 7.20–7.50 (m, 9H), 8.10 (d, 1H); m/z 716.3.

| Ex | Compound | NMR and m/z | SM |
|---|---|---|---|
| 96 | 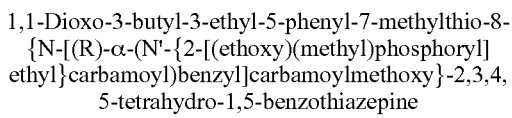 | 0.76–0.85(m, 6H), 1.00–1.52(m, 12H), 1.55–1.75(m, 1H), 1.95–2.12(br, 1H), 2.20(s, 3H), 3.10–3.25(m, 2H), 3.55–3.85(m, 4H), 3.85–4.00(m, 2H), 4.03–4.13(m, 2H), 4.6(q, 2H), 5.64(d, 1H), 6.66(s, 1H), 7.78(br, 1H), 6.95–7.10(m, 3H), 7.23–7.40(m, 6H), 7.43–7.49(m, 2H), 8.07(d, 1H); m/z 760.3 | Ex 38 |
| 97[1] | 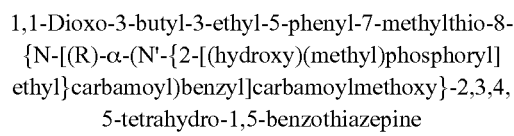 | (600MHz) 0.75–0.82(m, 6H), 1.0–1.42 (m, 13H), 1.64(brs, 1H), 2.18(s, 3H), 3.08–3.24(m, 2H), 3.50–3.84(m, 4H), 3.87–4.13(m, 2H), 4.54–4.68(m, 2H), 5.56–5.62(m, 1H), 6.63(s, 1H), 6.87–7.10(m, 3H), 7.24–7.40(m, 7H), 7.43–7.49(m, 2H), 7.98–8.05(m, 1H); m/z 730.5 | Ex 38 |

[1] Amine: Tetrahedron; EN; 49; 47; 1993; 11055–11064

Example 99

1,1-Dioxo-3-butyl-3-ethyl-5-phenyl-7-methylthio-8-[N-((R)-α-{N'-[(hydroxy)(ethoxy)phosphorylmethyl]carbamoyl}benzyl)carbamoylmethoxy]-2,3,4,5-tetrahydro-1,5-benzothiazepine To a solution of 1,1-dioxo-3-butyl-3-ethyl-5-phenyl-7-methylthio-8-[N-((R)-α-{N'-[(diethoxy)phosphorylmethyl]carbamoyl}benzyl)carbamoylmethoxy]-2,3,4,5-tetrahydro-1,5-benzothiazepine (Example 96; 13 mg, 0.017 mmol) in MeCN (0.5 ml) was added 1 M aqueous LiOH (0.171 ml, 0.171 mmol) dropwise. The reaction mixture was stirred at room temperature for 3 days. Acetic acid was added and the solvent evaporated under reduced pressure. The crude product was purified by preparative HPLC using MeCN and ammonium acetate buffer (45:55) as eluent to give the title compound 11 mg (88%). NMR (600 MHz, CD$_3$OD) 0.77–0.84 (m, 6H), 1.00–1.30 (m, 7H), 1.40–1.65 (m, 4H), 2.17 (s, 3H), 3.23 (brs, 2H), 3.51 (d, 2H), 3.6–3.85 (m, 4H), 4.70 (dd, 2H), 5.57 (s, 1H), 6.72 (s, 1H), 6.96 (t, 1H), 7.09 (d, 2H), 7.25–7.31 (m, 3H), 7.32–7.36 (m, 2H), 7.40 (s, 1H), 7.45 (d, 2H); m/z 732.4.

Example 100

1,1-Dioxo-3-butyl-3-ethyl-5-phenyl-7-methylthio-8-[N-((R)-α-{N'-[(hydroxy)(methyl)phosphorylmethyl]carbamoyl}benzyl)carbamoylmethoxy]-2,3,4,5-tetrahydro-1,5-benzothiazepine To a solution of 1,1-dioxo-3-butyl-3-ethyl-5-phenyl-7-methylthio-8-[N-((R)-α-{N'-[(ethoxy)(methyl)phosphorylmethyl]carbamoyl}benzyl)carbamoylmethoxy]-2,3,4,5-tetrahydro-1,5-benzothiazepine (Example 97; 85 mg, 0.12 mmol) in MeCN (2.4 ml) was added at 0° C. 1 M aqueous LiOH (1.17 ml, 1.17 mmol) dropwise. The reaction mixture was stirred at room temperature for 20 hours. Acetic acid was added and the solvent evaporated under reduced pressure. The crude product was purified by column chromatography using DCM/MeOH(Et$_3$N (100:15:0.2 and 100:30:0.2) as eluent to give the title compound 62 mg (76%). NMR (CD$_3$OD) 0.75–0.84 (m, 6H), 1.0–1.70 (m, 11H), 2.15 (s, 3H), 3.22 (brs, 2H), 3.35 (d, 2H), 3.60–3.90 (m, 2H), 4.70 (dd, 2H), 3.55 (s, 1H), 6.71 (s, 1H), 6.96 (t, 1H), 7.09 (d, 2H), 7.23–7.38 (m, 5H), 7.40 (s, 1H), 7.46 (d, 2H); m/z 702.3

Example 101

The following compound was synthesised by the procedure of Example 100 using the appropriate starting material.

Example 102

1,1-Dioxo-3-butyl-3-ethyl-5-phenyl-7-methylthio-8-[N-((R)-α-{N'-[di-(t-butoxy)phosphorylmethyl]carbamoyl}benzyl)carbamoylmethoxy]-2,3,4,5-tetrahydro-1,5-benzothiazepine To a solution of 1,1-dioxo-3-butyl-3-ethyl-5-phenyl-7-methylthio-8-[N-((R)-1'-phenyl-1'-carboxymethyl)carbamoylmethoxy]-2,3,4,5-tetrahydro-1,5-benzothiazepine (Example 38; 80 mg, 0.131 mmol) and di-(t-butoxy)phosphorylmethyamine (Tet. Lett.; EN; 33; 1; 1992; 77–80; 37 mg, 0.164 mmol) in DCM (5 ml) was added 2,6-lutidine (28 mg, 0.262 mmol) and TBTU (53 mg, 0.164 mmol). The reaction mixture was stirred at room temperature for 2 hours and 50 min. The solvent was evaporated under reduced pressure and the crude product was purified by column chromatography using DCM/MeOH (100:4) as eluent to give the title compound 92 mg (86%). NMR (500 MHz) 0.77–0.86 (m, 6H), 1.03–1.75 (m, 26H), 2.22 (s, 3H), 2.10–2.25 (m, 2H), 3.45–3.90 (m, 4H), 4.61 (dd, 2H), 5.52 (d, 1H), 5.94 (brs, 1H), 6.67 (s, 1H), 7.0 (t, 1H), 7.07 (d, 2H), 7.26–7.48 (m, 8H), 8.12 (d, 1H); m/z 704.22 [M-2(t-butyl)+2H].

Example 103

1,1-Dioxo-3-butyl-3-ethyl-5-phenyl-7-methylthio-8-[N-((R)-α-{N'-[di-(hydroxy)phosphorylmethyl]carbamoyl}benzyl)carbamoylmethoxy]-2,3,4,5-tetrahydro-1,5-benzothiazepine To a solution of 1,1-dioxo-3-butyl-3-ethyl-5-phenyl-7-methylthio-8-[N-((R)-α-{N'-[di-(t-butoxy) phosphorylmethyl]carbamoyl}benzyl)carbamoylmethoxy]-2,3,4,5-tetrahydro-1,5-benzothiazepine (Example 102; 72 mg, 0.088 mmol) in DCM (4 ml) was added at 0° C. TFA (1 ml). The reaction mixture was stirred at room temperature for 2 hours. The solvent was evaporated under reduced pressure and the residue was extracted with DCM/water. The organic layer was separated, washed with brine, dried and evaporated under reduced pressure. The residue was suspended in ether and the crystals filtered to give the title compound 60 mg (97%). NMR (500 MHz, DMSO-d$_6$) 0.70–0.80 (m, 6H), 0.99–1.61 (m, 8H), 2.18 (s, 3H), 2.80–4.0 (m, 6H), 4.80 (dd, 2H), 5.65 (d, 1H), 6.71 (s, 1H), 6.80–7.02 (m, 3H), 7.15–7.35 (m, 6H), 7.48 (d, 2H), 8.50–9.20 (m, 2H); m/z 704.3

| Ex | Compound | NMR(600MHz, CD$_3$OD) and m/z | SM |
|---|---|---|---|
| 101 | (structure) | 0.76–0.83(m, 6H), 1.05–1.55(m, 15H), 1.91–1.99(m, 2H), 2.15(s, 3H), 3.24 (brs, 2H), 3.40–3.50(m, 2H), 3.66–3.86 (m, 2H), 4.69(dd, 2H), 5.42(s, 1H), 6.70 (s, 1H), 6.92(t, 1H), 7.11(d, 2H), 7.25–7.39(m, 6H), 7.43(d, 2H); m/z 744.3 | Ex 104 |

Example 104

1,1-Dioxo-3,3-dibutyl-5-phenyl-7-methylthio-8-{N-[(R)-α-(N'-{2-[(methyl)(ethyl)phosphoryl]ethyl}carbamoyl)benzyl]carbamoylmethoxy}-2,3,4,5-tetrahydro-1,5-benzothiazepine To a solution of 1,1-dioxo-3,3-dibutyl-5-phenyl-7-methylthio-8-[N-((R)-1'-phenyl-1'-carboxymethyl)carbamoylmethoxy]-2,3,4,5-tetrahydro-1,5-benzothiazepine (Example 1; 60 mg, 0.094 mmol) and 2-[(methyl)(ethyl)phosphoryl]ethylamine (Helv. Chim. Acta; GE; 75; 8; 1992; 2545–2552; 20 mg, 0.132 mmol) was added at 0° C. 2,6-lutidine (20 mg, 0.19 mmol) and TBTU (39 mg, 0.121 mmol) under argon. The reaction mixture was stirred at room temperature for 70 min and then DCM was added and the solution washed with water and brine. The organic layer was dried and the solvent evaporated under reduced pressure. The residue was purified by column chromatography using DCM/MeOH (100:5) as eluent to give the title compound 67 mg (92%). NMR (300 MHz) 0.74–86 (m, 6H), 1.0–1.60 (m, 18H), 1.80–2.05 (m, 2H), 2.20 (s, 3H), 2.17 (s, 2H), 3.47–3.80 (m, 4H), 3.88–4.10 (dd, 2H), 5.52 (d, 1H), 6.65 (s, 1H), 6.95–7.12 (m, 3H), 7.13–7.42 (m, 7H), 7.43–7.49 (m, 2H), 8.05–8.16 (m, 1H); m/z 772.4.

Example 105

1,1-Dioxo-3,3-dibutyl-5-phenyl-7-methylthio-8-(N-{(R)-α-[N'-(2-mercapto-1-carboxyethyl)carbamoyl]benzyl}carbamoylmethoxy)-2,3,4,5-tetrahydro-1,5-benzothiazepine To a solution of 1,1-dioxo-3,3-dibutyl-5-phenyl-7-methylthio-8-[N-((R)-α-{N'-[2-(triphenylmethylsulphanyl)-1-(t-butoxycarbonyl)ethyl]carbamoyl}benzyl)carbamoylmethoxy]-2,3,4,5-tetrahydro-1,5-benzothiazepine (Method 91; 37 mg, 0.036 mmol) in DCM (1 ml) was added at 0° C. TFA (1 ml) under argon blanketing. The ice-bath was removed and triethylsilane (42 mg, 0.36 mmol) was added. The reaction mixture was stirred at room temperature for 2 hours and then the solvent evaporated under reduced pressure. The crude product was purified by preparative HPLC using MeCN and ammonium acetate buffer (40:60 to 60:40) as eluent to give the title compound 16 mg (59%). NMR (500 MHz, CD₃OD) 0.76–0.85 (m, 6H), 1.05–1.60 (m, 12H), 2.17 (s, 3H), 2.77–2.92 (m, 2H), 3.24 (brs, 2H), 3.61–3.88 (m, 2H), 4.56 (t, 1H), 4.70 (dd, 2H), 5.65 (s, 1H), 6.71 (s, 1H), 6.98 (t, 1H), 7.12 (d, 2H), 7.25–7.43 (m, 6H), 7.50 (d, 2H); m/z 742.4.

Example 106

The following compound was synthesised by the procedure of Example 105 using the appropriate starting material.

| Ex | Compound | NMR(500MHz, CD₃OD) and m/z | SM |
|---|---|---|---|
| 106 | *(structure shown)* | 0.77–0.85(m, 6H), 1.03–1.28(m, 8H), 1.38–1.58(m, 4H), 2.15(s, 3H), 2.87–3.5(m, 2H), 3.25(s, 2H), 3.75(brs, 2H), 4.55(s, 1H), 4.71(dd, 2H), 5.66 (s, 1H), 6.71(s, 1H), 6.98(t, 1H), 7.12 (d, 2H), 7.25–7.43(m, 6H), 7.49(d, 2H); m/z 742.28 | Meth 93 |

Example 107

1,1-Dioxo-3-butyl-3-ethyl-5-phenyl-7-bromo-8-(2-{N-[(R)-α-(carboxy)benzyl]carbamoyl}ethoxy)-2,3,4,5-tetrahydro-1,5-benzothiazepine To a solution of 1,1-dioxo-3-butyl-3-ethyl-5-phenyl-7-bromo-8-(2-{N-[(R)-α-(t-butoxycarbonyl)benzyl]carbamoyl}ethoxy)-2,3,4,5-tetrahydro-1,5-benzothiazepine (Method 90; 77 mg, 0.108 mmol) in DCM (3 ml) was added at 0° C. TFA (0.75 ml). The reaction mixture was stirred at room temperature for 2 h and 45 min. The solvent was evaporated under reduced pressure and the crude product was purified by preparative HPLC using MeCN and ammonium acetate buffer (40:60 to 50:50) as eluent to give the title compound 60 mg (82%). NMR (500 MHz, CD₃OD) 0.75–0.85 (m, 6H), 1.0–1.25 (m, 4H), 1.40–1.64 (m, 4H), 2.75–2.90 (m, 2H), 3.26 (s, 2H), 3.50–3.90 (m, 2H), 4.30–4.41 (m, 2H), 5.43 (s, 1H), 6.99 (t, 1H), 7.05–7.13 (m, 3H), 7.23–7.34 (m, 5H), 7.45 (d, 2H), 7.52 (s, 1H); m/z 658.

Example 108

The following compound was synthesised by the procedure of Example 107 using the appropriate starting material.

| Ex | Compound | NMR(500MHz, CD₃OD) and m/z | SM |
|---|---|---|---|
| 108 | | 0.78–0.85(m, 6H), 1.02–1.30(m, 8H), 1.38–1.58(m, 4H), 1.87(s, 3H), 2.15(s, 3H), 2.77–2.83(m, 1H), 2.87–2.94(m, 1H), 3.24(s, 2H), 3.74 (brs, 2H), 4.53–4.59(m, 1H), 4.68 (dd, 2H), 5.66(s, 1H), 6.71(s, 1H), 6.98(t, 1H), 7.12(d, 2H), 7.25–7.31 (m, 3H), 7.32–7.36(m, 2H), 7.40(s, 1H), 7.49(d, 2H); m/z 756.23 | Meth 92 |

Example 109

1,1-Dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoyl-methoxy}-2,3,4,5-tetrahydro-1,5-benzothiazepine To a solution of 1,1-dioxo-3,3-dibutyl-5-phenyl-7-methylthio-S-8-]N-((R)-α-carboxy-4-hydroxybenzyl)carbamoylmethoxy]-2,3,4,5-tetrahydro-1,5-benzothiazepine (Example 2; 80 mg, 0.122 mmol) and 2-[(methyl)(ethyl)phosphoryl]ethylamine (Helv. Chim. Acta; GE; 75; 8; 1992; 2545–2552; 24 mg, 0.159 mmol) in DCM (2 ml) was added 2,6-lutidine (26 mg, 0.244 mmol) and TBTU (51 mg, 0.159 mmol) under argon. The reaction mixture was stirred at room temperature for 60 min, then diluted with DCM. The solution was washed with water, brine, dried and the solvent was evaporated under reduced pressure. The residue was purified by column chromatography using DCM/MeOH (100:7) as eluent to give the title compound 67 mg (92%). NMR (600 MHz), 0.74–0.80 (m, 6H), 1.0–1.55 (m, 18H), 1.82–1.98 (m, 2H), 2.15 (s, 3H), 3.14 (brs, 2H), 3.40–3.56 (m, 2H), 3.70 (brs, 2H), 3.89–4.02 (m, 2H), 4.51(dd, 2H), 5.33 (t, 1H), 6.61 (s, 1H), 6.65–6.72 (m, 2H), 6.95 (t, 1H), 7.03 (d, 2H), 7.12–7.19 (m, 3H), 7.22–7.26 (m, 2H), 7.32 (s, 1H), 8.11 (t, 1H); m/z 788.56.

Example 110

1,1-Dioxo-3,3-dibutyl-5-phenyl-7-methylthio-8-{N-[(R)-α-(N'-{2-[(methyl)(hydroxy)phosphoryl]ethyl}carbamoyl-4-hydroxybenzyl]carbamoyl-methoxy}-2,3,4,5-tetrahydro-1,5-benzothiazepine To a solution of 1,1-dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoylmethoxy}-2,3,4,5-tetrahydro-1,5-benzothiazepine (Example 104; 37 mg, 0.047 mmol) in MeCN/MeOH (4 ml, 1:1) was added 1 M aqueous LiOH (0.8 ml, 0.8 mmol). The reaction mixture was stirred at room temperature for 40 min. Acetic acid was added and the solvent evaporated under reduced pressure. The crude product was purified by preparative HPLC using MeCN and ammonium acetate buffer (40:60 and 45:55) as eluent to give the title compound 35 mg (96%). NMR (500 MHz, CD₃OD) 0.78–0.85 (m, 6H), 1.06–1.28 (m, 11H), 1.39–1.57 (m, 4H), 1.72–1.85 (m, 2H), 2.16 (s, 3H), 2.24 (s, 2H), 3.40–3.50 (m, 2H), 3.65–3.84 (m, 2H), 4.69 (dd, 2H), 5.36 (s, 1H), 6.71 (s, 1H), 6.76 (d, 2H), 6.99 (t, 1H), 7.13 (d, 2H), 7.22–7.33 (m, 4H), 7.39 (s, 1H); m/z 760.27

Example 111

1,1-Dioxo-3,3-dibutyl-5-phenyl-7-methylthio-8-(N-{(R)-α-[(R)-N'-(2-methylsulphinyl-1-carboxyethyl)carbamoyl]benzyl}carbamoylmethoxy)-2,3,4,5-tetrahydro-1,5-benzothiazepine The title compound was separated as by-product from the synthesis of Example 108. NMR (500 MHz, CD₃OD) 0.78–0.85 (m, 6H), 1.02–1.60 (m, 12H), 2.16 (d, 3H), 2.53 (d, 3H), 3.08–3.18 (m, 1H), 3.24 (s, 2H), 3.35 (v br, 1H), 3.75 (v br, 2H), 4.62 (v br, 1H), 4.71 (dd, 2H), 5.60 (d, 1H), 7.71 (s, 1H), 6.98 (t, 1H), 7.12 (d, 2H), 7.25–7.42 (m, 6H), 7.47 (d, 2H); m/z 772.25.

Example 112

1,1-Dioxo-3,3-dibutyl-5-phenyl-7-methylthio-8-(N-{(R)-α-[(S)-N'-(3-methylthio-2-carboxypropyl)carbamoyl]benzyl}carbamoylmethoxy)-2,3,4,5-tetrahydro-1,5-benzothiazepine To a solution of 1,1-dioxo-3,3-dibutyl-5-phenyl-7-methylthio-8-(N-{(R)-α-[(S)-N'-(3-methylthio-2-methoxycarbonylpropyl)carbamoyl]benzyl}carbamoylmethoxy)-2,3,4,5-tetrahydro-1,5-benzothiazepine (Method 94; 68 mg, 0.087 mmol) in ethanol (5 ml) was added NaOH (9 mg in 0.4 ml water) at 0° C. The reaction mixture was stirred at room temperature for 2.5 hours. Acetic acid was added and the solvent evaporated under reduced pressure. The crude product was purified by preparative HPLC using MeCN and ammonium acetate buffer (40:60 to 60:40) as eluent to give the title compound 52 mg (76%). NMR (500 MRz, CD₃OD) 0.79–0.86 (m, 6H), 1.05–1.29 (m, 8H), 1.40–1.58 (m, 4H), 1.84–1.93 (m, 4H), 2.01–2.21 (m, 5H), 2.26–2.34 (m, 1H), 3.26 (s, 2H), 3.76 (brs, 2H), 4.52–4.58 (m, 1H), 4.70 (dd, 2H), 5.61 (s, 1H), 6.73 (s, 1H), 7.0 (t, 1H), 7.14 (d, 2H), 7.27–7.43 (m, 6H), 7.49 (d, 2H); m/z 770.16.

Example 113

1,1-Dioxo-3,3-dibutyl-5-phenyl-7-methylthio-8-(N-{(R)-α-[(S)-N'-(2-methylthio-1-carboxyethyl)carbamoyl]benzyl}carbamoylmethoxy)-2,3,4,5-tetrahydro-1,5-benzothiazepine To a solution of 1,1-dioxo-3,3-dibutyl-5-phenyl-7-methylthio-8-(N-{(R)-α-[(S)-N'-(2-mercapto-1-carboxyethyl)carbamoyl]benzyl}carbamoylmethoxy)-2,3,4,5-tetrahydro-1,5-benzothiazepine (Example 106; 15 mg, 0.02 mmol) in methanol (1.5 ml) was added sodium methoxide (0.104 mmol in 0.14 ml methanol) and methyl iodide (0.16 mmol) under nitrogen. The reaction mixture was stirred at room temperature for 50 min. Acetic acid was added. The solvent was evaporated under reduced pressure and the residue was extracted with DCM/water. The organic layer was separated washed with brine, dried and evaporated under reduced pressure to give the title compound 4 mg (26%). NMR (500 MHz, $CD_3OD$) 0.75–8.30 (m, 6H), 1:03–1.57 (m, 12H), 2.10 (s, 3H), 2.17 (s, 3H), 2.83–2.30 (m, 1H), 3.0–3.25 (m, 1H), 3.26 (s, 92H), 3.77 (brs, 2H), 4.58–4.63 (m, 1H), 4.72 (dd, 2H), 5.64 (s, 1H), 6.72 (s, 1H), 7.0 (t, 1H), 7.12 (d, 2H), 7.28–7.52 (m, 8H); m/z 756.25.

Example 114

1,1-Dioxo-3,3-dibutyl-5-(4-chlorophenyl)-7-methylthio-8-[N-{(R)-α-[N'-(carboxymethyl)carbamoyl]benzyl}carbamoylmethoxy]-2,3,4,5-tetrahydro-1,5-benzothiazepine To a solution of 1,1-dioxo-3,3-dibutyl-5-(4-chlorophenyl)-7-methylthio-8-[N-{(R)-α-[N'-(t-butoxycarbonylmethyl)carbamoyl]benzyl}carbamoylmethoxy]-2,3,4,5-tetrahydro-1,5-benzothiazepine (Method 102; 129 mg, 0.164 mmol) in DCM (5 ml) was added at 0° C. TFA (1.5 ml) under nitrogen. The reaction mixture was stirred at room temperature for 2 hours. The solvent was evaporated under reduced pressure and the crude product was purified by preparative HPLC using MeCN and ammonium acetate buffer (40:60 to 50:50) as eluent to give the title compound 77 mg (63%). NMR (500 MHz, $CD_3OD$) 0.84 (t, 6H), 1.10–1.22 (m, 8H), 1.35–1.45 (m, 4H), 2.34 (s, 3H), 3.19–3.27 (m, 2H), 3.55 (s, 2H), 3.87 (dd, 2H), 4.67 (dd, 2H), 5.61 (s, 1H), 7.09–7.15 (m, 3H), 7.27–7.37 (m, 6H), 7.47 (d, 2H); m/z 7.48.03 (M+$NH_3$).

Example 115

1,1-Dioxo-3,3-dipropyl-5-phenyl-7-methylthio-8-[N-{(R)-α-[N'-(2-sulphoethyl)carbamoyl]-4-hydroxybenzyl}carbamoylmethoxy]-2,3,4,5-tetrahydro-1,5-benzothiazepine To a solution of 1,1-dioxo-3,3-dipropyl-5-phenyl-7-methylthio-8-carboxymethoxy-2,3,4,5-tetrahydro-1,5-benzothiazepine (Method 118; 0.050 g, 0.105 mmol) in DMF (4 ml) was added 2-{[(2R)-2-amino-2-(4-hydroxyphenyl)ethanoyl]amino}ethanesulphonic acid (Method 80; 0.037 g, 0.135 mmol) and N-methylmorpholine (0.040 ml, 0.363 mmol). The mixture was stirred for 10 min and then was TBTU (0.044 g, 0.137 mmol) added. The reaction mixture was stirred for two days before the solvent was removed under reduced pressure. The residue was purified by preparative HPLC using a MeCN/ammonium acetate buffer to give the title compound in 0.042 g (55%) as a white solid. NMR (DMSO-$d_6$) 0.60–0.80 (m, 6H), 1.05–1.50 (m, 8H), 2.15 (s, 3H), 2.45–2.55 (m, 21H), 3.05–3.80 (m, 6H), 4.70 (ABd, 1H), 4.80 (ABd, 1H), 5.25 (d, 1H), 6.65–6.75 (m, 3H), 6.80–7.05 (m, 3H), 7.10–7.25 (m, 4H), 7.30 (s, 1H), 8.20–8.30 (m, 1H). 8.45 (d, 1H).

Example 116

1,1-Dioxo-3,3-dipropyl-5-phenyl-7-methylthio-8-[N-{(R)-α-[N'-(carboxymethyl)carbamoyl]-4-hydroxybenzyl}carbamoylmethoxy]-2,3,4,5-tetrahydro-1,5-benzothiazepine To a solution of 1,1-dioxo-3,3-dipropyl-5-phenyl-7-methylthio-8-carboxymethoxy-2,3,4,5-tetrahydro-1,5-benzothiazepine (Method 118; 0.050 g, 0.105 mmol) in DCM (4 ml) was added (R)-α-[N-(t-butoxycarbonylmethyl)carbamoyl]benzylamine (Method 86; 0.036 g, 0.136 mmol) and N-methylmorpholine (0.040 ml, 0.363 mmol). The mixture was stirred for 5 min and then was TBTU (0.044 g, 0.137 mmol) added. The reaction mixture was stirred for two days and then was TFA (1.5 ml) added. After 1.5 h, the solution was diluted with toluene; before the solvent was removed under reduced pressure. The residue was purified by preparative HPLC using a MeCN/ammonium acetate buffer to give the title compound in 0.020 g (29%) as a white solid. NMR (DMSO-$d_6$) 0.60–0.80 (m, 6H), 1.05–1.50 (m, 8H), 2.15 (s, 3H), 3.10–3.80 (m, 6H), 4.70 (ABd, 1H), 4.85 (ABd, 1H), 5.60 (d, 1H), 6.70 (s, 1H), 6.80–7.05 (m, 3H), 7.15–7.50 (m, 8H), 8.35 (brs, 1H), 8.55 (d, 1H).

Example 117

1,1-Dioxo-3,3-dibutyl-5-phenyl-7methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine To a solution of 1,1-dioxo-3,3-dibutyl-5-phenyl-7-methoxy-8-carboxymethoxy-2,3,4,5-tetrahydro-1,5-benzothiazepine (Method 6; 0.020 g, $4.09*10^{-5}$ mol) in DMF (4 ml) was added 2-{[(2R)-2-amino-2-(4-hydroxyphenyl)ethanoyl]amino}ethanesulphonic acid (Method 80; 0.014 g, $5.10*10^{-5}$ mol) and N-methylmorpholine (0.020 ml, $1.81*10^{-4}$ mol). The mixture was stirred for 10 min and then was TBTU (0.016 g, $4.98*10^{-5}$ mol) added. The reaction mixture was stirred for 3 h and then the solvent was removed under reduced pressure. The residue was purified by preparative HPLC using a MeCN/ammonium acetate buffer to give the title compound in 0.023 g (75%) as a white solid. NMR (500 MHz, DMSO-$d_6$) 0.65–0.80 (m, 6H), 0.80–1.50 (m, 12H), 2.40–2.60 (m, 2H), 3.15–3.45 (m, 4H), 3.60 (s, 3H), 3.65 (brs, 2H), 4.60 (ABd, 1H), 4.70 (ABd, 1H), 5.25 (d, 1H), 6.50 (s, 1H), 6.70–7.25 (m, 10H), 7.35 (s, 1H), 8.20–8.30 (m, 1H). 8.50 (d, 1H), 9.40 (brs, 1H).

Example 118

1,1-Dioxo-3-butyl-3-ethyl-5-phenyl-8-[N-{(R)-α-[N'-(2-sulphoethyl)carbamoyl]-4-hydroxybenzyl}carbamoylmethoxy]-2,3,4,5-tetrahydro-1,5-benzothiazepine To a solution of 1,1-dioxo-3-butyl-3-ethyl-5-phenyl-8-carboxymethoxy-2,3,4,5-tetrahydro-1,5-benzothiazepine (Method 115; 0.020 g, $4.63*10^{-5}$ mol) in DMF (4 ml) was added 2-{[(2R)-2-amino-2-(4-hydroxyphenyl)ethanoyl]

amino}ethanesulphonic acid (Method 80; 0.017 g, 6.20*10$^{-5}$ mol) and N-methylmorpholine (0.016 ml, 1.46*10$^{-4}$ mol). The mixture was stirred for 10 min and then TBTU (0.019 g, 5.92*10$^{-5}$ mol) was added. The reaction mixture was stirred overnight and then the solvent was removed under reduced pressure. The residue was purified by preparative HPLC using a MeCN/ammonium acetate buffer to give the title compound in 0.008 g (24%) as a white solid. NMR (500 MHz, DMSO-d$_6$) 0.65–0.80 (m, 6H), 0.80–1.60 (m, 8H), 2.40–2.55 (m, 2M), 3.20–3.40 (m, 4H), 3.65 (brs, 2H), 4.65 (ABd, 1H), 4.70 (ABd, 1H), 5.25 (d, 1H), 6.65–7.45 (m, 13H), 8.20–8.30 (m, 1H). 8.60 (d, 1H), 9.40 (brs, 1H).

Example 119

1,1-Dioxo-3,3-dibutyl-5-(4-t-butoxycarbonylaminophenyl)-8-[N-α-(R)-carboxybenzyl)carbamoylmethoxy]-2,3,4,5-tetrahydro-1,5-benzothiazepine The title compound was synthesized from 1,1-oxo-3,3-dibutyl-5-(4-t-butoxycarbonylaminophenyl)-8-[N-α-(R)-methoxycarbonylbenzyl)carbamoylmethoxy]-2,3,4,5-tetrahydro-1,5-benzothiazepine (Method 45) by the procedure of Method 109. NMR (CD$_3$OD) 0.81 (brt, 6H), 1.03–1.3 (m, 8H), 1.32–1.59 (m, 13H), 3.24 (brs, 2H), 3.57–3.77 (m, 2H), 4.61 (brs, 2H), 5.51 (s, 1H), 6.83 (d, 1H), 7.0–7.1 (m, 3H), 7.26–7.43 (m, 7H), 7.49 (d, 1H); m/z 708.5.

Example 120

1,1-Dioxo-3,3-dibutyl-5-[4-(N'-t-butylureido)phenyl]-8-[N-α-(R)-carboxybenzyl)carbamoylmethoxy]-2,3,4,5-tetrahydro-1,5-benzothiazepine 1,1-Dioxo-3,3-dibutyl-5-(4-(N'-t-butylureido)phenyl)-8-[N-α-(R)-methoxycarbonylbenzyl)carbamoylmethoxy]-2,3,4,5-tetrahydro-1,5-benzothiazepine (Method 111; 30 mg, 0.042 mmol) was dissolved in THF (1.5 ml), H$_2$O (0.5 ml) and LiOH (42 mg, 0.064 mmol, monohydrate) was added. The mixture was stirred for 2 hours. The compound was purified by preparative HPLC using an MeCN/ammonium acetate buffer gradient (5/95 to 100/0) as eluent to give the title product, 24 mg (82%). NMR (CD$_3$OD) 0.81 (brt, 6H), 1.05–1.26 (m, 8H), 1.35 (s, 9H), 1.38–1.57 (m, 4H), 3.25 (brs, 2H), 3.6–3.77 (m, 2H), 4.61 (ABq, 2H), 5.45 (s, 1H), 6.84 (d, 1H), 7.01–7.11 (m, 3H), 7.24 (d, 2H), 7.26–7.37 (m, 3H), 7.37–7.42 (m, 2H), 7.50 (d, 1H); m/z 707.5.

Preparation of Starting Materials

The starting materials for the Examples above are either commercially available or are readily prepared by standard methods from known materials. For example, the following reactions are an illustration, but not a limitation, of some of the starting materials used in the above reactions.

Method 1

1,1-Dioxo-3-butyl-3-ethyl-5-phenyl-7-bromo-8-[1'-(ethoxycarbonyl)ethoxy]-2,3,4,5-tetrahydro-1,5-benzothiazepine Sodium carbonate (0.30 g, 2.83 mmol), 2-bromopropanoic acid ethyl ester (0.145 g, 0.796 mmol) and tetrabutylammonium bromide (0.022 g, 0.07 mmol) was added to a solution of 1,1-dioxo-3-butyl-3-ethyl-5-phenyl-7-bromo-8-hydroxy-2,3,4,5-tetrahydro-1,5-benzothiazepine (WO 96/16051; 0.300 g, 0.663 mmol) in MeCN (10 ml). The suspension was heated under reflux overnight. The solvent was evaporated and the crude mixture was extracted (DCM/H$_2$O), dried. (MgSO$_4$), evaporated and purified by flash chromatography (Hex:EtOAc-5:1) to give the title compound 0.346 g (95%) as a white solid. NMR 0.70–0.85 (m, 6H), 1.00–1.75 (m, 8H), 1.35 (t, 3H), 1.70 (d, 3H), 3.05–3.25 (m, 2H), 3.55–3.90 (m, 2H), 4.20–4.35 (m, 2H), 4.80 (q, 1H), 7.00–7.10 (m, 3H), 7.15 (s, 1H), 7.25–7.35 (m, 2H), 7.45 (s, 1H).

Method 2

1,1-Dioxo-3-butyl-3-ethyl-5-phenyl-7-bromo-8-[1'-carboxyethoxy]-2,3,4,5-tetrahydro-1,5-benzothiazepine Sodium hydroxide (0.045 g, 1.13 mmol) was added to a solution of 1,1-dioxo-3-butyl-3-ethyl-5-phenyl-7-bromo-8-[1-(ethoxycarbonyl)ethoxy]-2,3,4,5-tetrahydro-1,5-benzothiazepine (Method 1; 0.050 g, 0.090 mmol) in EtOH (4 ml, 95%) and heated under reflux. After 1.5 hours AcOH (0.2 ml) was added and most of the solvent was removed under reduced pressure. The crude product was extracted (DCM/H$_2$O), dried (MgSO$_4$) and evaporated to give the title compound 0.031 g (65%) as white solid. NMR (500 MHz, CD$_3$OD) 0.70–0.85 (m, 6H), 0.95–1.25 (m, 4H), 1.35–1.70 (m, 4H), 2.65 (d, 3H), 3.10–3.35 (m, 2H), 3.45–3.95 (m, 2H), 4.70 (q, 1H), 6.90–7.35 (m, 6H), 7.45 (s, 1H).

Method 3

1,1-Dioxo-3-butyl-3-ethyl-5-phenyl-7-bromo-8-[1'-phenyl-1'-ethoxycarbonylmethoxy]-2,3,4,5-tetrahydro-1,5-benzothiazepine Ethyl α-bromophenylacetate (0.139 g), Na$_2$CO$_3$ (0.200 g) and tetrabutylammonium bromide (0.034 g) were added to a solution of 1,1-dioxo-3-butyl-3-ethyl-5-phenyl-7-bromo-8-hydroxy-2,3,4,5-tetrahydro-1,5-benzothiazepine (WO 96/16051; 0.200 g, 0.442 mmol) in MeCN (6 ml). The suspension was heated under reflux overnight before the solvent was removed under reduced pressure. The crude product was extracted (DCM/H$_2$O) and purified by flash chromatography (Hex:EtOAc-5:1) to give the title compound 0.256 g (94%) as a white solid. NMR 0.65–0.85 (m, 6H), 0.95–1.65 (m, 8H), 3.00–3.15 (m, 2H), 3.50–3.80 (m, 2H), 3.70–3.80 (2s, 3H), 5.60 (s, 1H), 5.65 (d, 1H) 7.00–7.60 (m, 17H), 8.05–8.20 (2d, 1H).

Method 4

1,1-Dioxo-3-butyl-3-ethyl-5-phenyl-7-bromo-8-[1'-phenyl-1'-carboxymethoxy]-2,3,4,5-tetrahydro-1,5-benzothiazepine Lithium hydroxide (0.019 g) was added to a solution of 1,1-dioxo-3-butyl-3-ethyl-5-phenyl-7-bromo-8-[1'-phenyl-1'-ethoxycarbonylmethoxy]-2,3,4,5-tetrahydro-1,5-benzothiazepine (Method 3; 0.244 g, 0.397 mmol) in THF/H$_2$O (2/1, 3 ml). After 2 days the solvent was removed under reduced pressure and the crude mixture was purified by HPLC to give the title compound 0.215 g (92%) as a white solid. NMR (CD$_3$OD) 0.60–0.80 (m, 6H), 0.90–1.25 (m, 4H), 1.30–1.60 (m, 4H), 3.05–3.30 (m, 2H), 3.40–3.90 (m, 2H), 5.55 (s, 1H), 6.85–7.70 (m, 12H).

Method 5

1,1-Dioxo-3,3-dibutyl-5-phenyl-7-methoxy-8-ethoxycarbonylmethoxy-2,3,4,5-tetrahydro-1,5-benzothiazepine Ethyl bromoacetate (0.13 ml), $Na_2CO_3$ (0.40 g) and tetrabutylammonium bromide (0.030 g) were added to a solution of 1,1-dioxo-3,3-dibutyl-5-phenyl-7-methoxy-8-hydroxy-2,3,4,5-tetrahydro-1,5-benzothiazepine (synthesised by the of WO9616051 for the corresponding 3-butyl-3-ethyl analogue; 0.400 g, 0.927 mmol) in MeCN (10 ml). The suspension was heated under reflux overnight before most of the solvent was removed under reduced pressure. The crude product was extracted (DCM/$H_2O$) and filtered through a short silica-column (DCM:EtOAc-1:4) to give the title compound 0.476 g (99%). NMR 0.65–0.85 (m, 6H), 0.95–1.65 (m, 8H), 3.00–3.15 (m, 2H), 3.50–3.80 (m, 2H), 3.70–3.80 (s, 3H), 5.60 (s, 1H), 5.65 (d, 1H) 7.00–7.60 (m, 17H), 8.05–8.20 (d, 1H).

Method 6

1,1-Dioxo-3,3-dibutyl-5-phenyl-7-methoxy-8-carboxymethoxy-2,3,4,5-tetrahydro-1,5-benzothiazepine Lithium hydroxide (0.062 g) was added to a solution of 1,1-dioxo-3,3-dibutyl-5-phenyl-7-methoxy-8-ethoxycarbonylmethoxy-2,3,4,5-tetrahydro-1,5-benzothiazepine (Method 5; 0.448 g, 0.865 mmol) in THF/$H_2O$ (2/1, 6 ml) After 1 hour AcOH (0.5 ml) was added and most of the solvent was removed under reduced pressure. The crude product was purified by HPLC (MeCN) to give the title compound 0.408 g (96%) as a white solid. NMR ($CD_3OD$) 0.75–0.85 (m, 6H), 1.00–1.30 (m, 8H), 1.35–1.55 (m, 4H), 3.20 (s, 2H), 3.65 (s, 3H), 3.70 (brs, 2H), 4.50 (s, 2H), 6.50 (s, 1H), 6.90–7.30 (m, 5H), 7.40 (s, 1H).

Method 7

1,1-Dioxo-3-butyl-3-ethyl-5-phenyl-7-methoxy-8-ethoxycarbonylmethoxy-2,3,4,5-tetrahydro-1,5-benzothiazepine 1,1-Dioxo-3-butyl-3-ethyl-5-phenyl-7-methoxy-8-hydroxy-2,3,4,5-tetrahydro-1,5-benzothiazepine (WO 9616051; 1.0 g), ethyl bromoacetate (0.50 g), sodium carbonate (1.2 g) and tetrabutylammonium bromide (60 mg) in MeCN (15 ml) were refluxed overnight. The solvent was removed under reduced pressure and the residue was extracted (DCM/$H_2O$). The organic layer was separated and the solvent was removed under reduced pressure. The residue purified by chromatography (DCM/EtOAc (90:10)) to give the title compound 1.2 g (98%). NMR ($CD_3OD$) 0.75–0.85 (m, 6H), 1.00–1.30 (m, 8H), 1.35–1.55 (m, 4H), 3.20 (s, 2H), 3.65 (s, 3H), 3.70 (brs, 2H), 4.50 (s, 2H), 6.50 (s, 1H), 6.90–7.30 (m, 5H), 7.40 (s, 1H).

Method 8

1,1-Dioxo-3-butyl-3-ethyl-5-phenyl-7-bromo-8-ethoxycarbonylmethoxy-2,3,4,5-tetrahydro-1,5-benzothiazepine A mixture of 1,1-dioxo-3-butyl-3-ethyl-5-phenyl-7-bromo-8-hydroxy-2,3,4,5-tetrahydro-1,5-benzothiazepine (WO 96/16051; 0.3 g), ethyl bromoacetate (0.14 g), sodium carbonate (0.3 g), tetrabutylammonium bromide (0.02 g) in MeCN (10 ml) were refluxed for 4 hours. The solvent was removed under reduced pressure. The residue was partitioned, between DCM/$H_2O$ and the organic layer was separated. The solvent was evaporated and the residue was purified by chromatography (DCM/EtOAc, 90:10) to give the title compound 0.34 g (95%). NMR (500 MHz) 0.7–0.9 (m, 6H), 1.0–1.8 (m, 11H), 3.2 (m, 2H), 3.6–3.8 (brs, 2H), 4.3 (q, 2H), 4.7 (s, 2H), 7.0–7.1 (m, 3H), 7.15 (s, 1H), 7.3 (m, 2H), 7.4 (s, 1H).

Method 9

1,1-Dioxo-3-butyl-3-ethyl-5-phenyl-7-bromo-8-carboxymethoxy-2,3,4,5-tetrahydro-1,5-benzothiazepine 1,1-Dioxo-3-butyl-3-ethyl-5-phenyl-7-bromo-8-ethoxycarbonylmethoxy-2,3,4,5-tetrahydro-1,5-benzothiazepine (Method 8; 0.34 g) and sodium hydroxide (0.3 g) were dissolved in ethanol and the mixture was heated to reflux for 1 hour. Acetic acid (1 ml) was added and the solvent was removed at reduced pressure. The residue was partitioned between DCM/$H_2O$ and the organic layer was separated and dried. Trituration of the residue with n-hexane gave the title compound 0.29 g (90%) as a solid. NMR (500 MHz) 0.7–0.8 (m, 6H), 1.0–1.7 (m, 8H), 3.1–3.2 (m, 2H), 3.6 (brs, 2H), 4.6 (s, 2H), 6.9–7.1 (m, 4H), 7.2 (m, 2H), 7.5 (s, 1H).

Method 10

1,1-Dioxo-3-butyl-3-ethyl-5-phenyl-7-methoxy-8-carboxymethoxy-2,3,4,5-tetrahydro-1,5-benzothiazepine 1,1-Dioxo-3-butyl-3-ethyl-5-phenyl-7-methoxy-8-ethoxycarbonylmethoxy-2,3,4,5-tetrahydro-1,5-benzothiazepine (Method 7; 1.2 g) was dissolved in ethanol (20 ml). Sodium hydroxide (0.5) dissolved in $H_2O$ (1 ml) was added and the reaction mixture was warmed to 40° C. for 30 min. Acetic acid (1 ml) was added and the solvent was removed at reduced pressure. The residue was partitioned between DCM/$H_2O$ and the organic layer was separated and dried. Trituration of the residue with n-hexane gave the title compound 1.1 g (97%) as a solid. NMR 0.75–0.85 (m, 3H), 0.9 (t, 3H), 1.0–1.7 (m, 8H), 3.2 (q, 2H), 3.65 (s, 3H), 3.65–3.85 (m, 2H), 4.7 (s, 2H), 6.4 (s, 1H), 7.0 (t, 1H), 7.1 (d, 2H), 7.3 (t, 2H), 7.5 (s, 1H).

Method 11

1,1-Dioxo-3,3-dibutyl-5-phenyl-7-bromo-8-ethoxycarbonylmethoxy-2,3,4,5-tetrahydro-1,5-benzothiazepine 1,1-Dioxo-3,3-dibutyl-5-phenyl-7-bromo-8-hydroxy-2,3,4,5-tetrahydro-1,5-benzothiazepine (synthesised by the of WO9616051 for the corresponding 3-butyl-3-ethyl analogue; 2.0 g, 4.16 mmol), ethyl bromoacetate (0.84 g, 5.03 mmol), sodium carbonate (2.0 g, 18.9 mmol) and tetrabutylammonium bromide (80 mg, 0.25 mmol) were added to MeCN (20 ml). The mixture was refluxed for 2 hours and then evaporated under reduced pressure. The residue was extracted with DCM/water. The DCM layer was separated and evaporated under reduced pressure. The residue was purified by column chromatography. The product was eluted with DCM/EtOAc (90:10) to give the title compound 2.2 g (93%). NMR 0.7–0.8 (m, 6H), 1.0–1.6 (m, 15H), 3.2 (brs, 2H), 3.7 (brs, 2H), 4.3 (q, 2H), 4.7 (s, 2H), 7.0–7.3 (m, 6H), 7.4 (s, 1H).

Methods 12–13

The following compounds were synthesised by the procedure of Method 11 using the appropriate acid and amine (source not indicated where commercially available).

| Meth | Compound | M/z | SM |
|---|---|---|---|
| 12 | Enantiomer 1 | 538 | Meth 83 |
| 13 | Enantiomer 2 | 538 | Meth 84 |

Method 14

1,1-Dioxo-3,3-dibutyl-5-phenyl-7-bromo-8-carboxymethoxy-2,3,4,5-tetrahydro-1,5-benzothiazepine 1,1-Dioxo-3,3-dibutyl-5-phenyl-7-bromo-8-ethoxycarbonylmethoxy-2,3,4,5-tetrahydro-1,5-benzothiazepine (Method 11; 2.2 g, 3.88 mmol) was dissolved in ethanol (15 ml). NaOH (0.8 g in 1.5 ml water) was added to the solution and the mixture was stirred for 30 min at room temperature. Acetic acid (2 ml) was added. The solvent was evaporated under reduced pressure and the residue was extracted with EtOAc/water. The EtOAc layer was separated, dried and evaporated under reduced pressure to give the title compound 2.0 g (95%). NMR (500 MHz) 0.7–0.8 (m, 6H), 1.0–1.5 (m, 12H), 3.2 (brs, 2H), 3.7 (brs, 2H), 4.7 (s, 2H), 7.0–7.3 (m, 6H), 7.4 (s, 1H).

Method 15

1,1-Dioxo-3-butyl-3-ethyl-5-phenyl-7-isopropoxy-8-carboxymethoxy-2,3,4,5-tetrahydro-1,5-benzothiazepine To isopropyl alcohol (12 ml) was added sodium (115 mg, 5 mmol) and the temperature was then raised to 80° C. to let the alcohol salt form. After all the sodium was dissolved 1,1-dioxo-3-butyl-3-ethyl-5-phenyl-7-bromo-8-carboxymethoxy-2,3,4,5-tetrahydro-1,5-benzothiazepine (Method 9; 100 mg, 0.2 mmol) was added in one portion. The reaction was then refluxed overnight, and then cooled to room temperature and quenched with acetic acid. The solvent was then removed under reduced pressure and the residue was dissolved in water and MeCN (70/30) and partially purified by HPLC. The residue was dissolved in ethylene glycol and NaOH (500 mg) was added. This reaction mixture was heated to 125° C. overnight and then cooled to room temperature and quenched with acetic acid, and EtOAc (100 ml) was added. The ethylene glycol was removed by washing the organic layer with acidic water three times. The organic layer was then concentrated and the residue was purified again as above to give the title compound 40 mg (41%). NMR (300 MHz) 0.7–1.0 (m, 6H), 1.0–1.8 (m, 15H), 3.2 (q, 2H), 3.75 (m, 2H), 4.3 (q, 2H), 4.6 (s, 2H), 6.35 (s, 1H), 6.95–7.2 (m, 3H), 7.2–7.4 (m, 2H), 7.55 (s, 1H).

Method 16

1,1-Dioxo-3-butyl-3-ethyl-5-phenyl-7-methylthio-8-ethoxcarbonylmethoxy-2,3,4,5-tetrahydro-1,5-benzothiazepine To 1,1-dioxo-3-butyl-3-ethyl-5-phenyl-7-methylthio-8-hydroxy-2,3,4,5-tetrahydro-1,5-benzothiazepine (Method 25; 500 mg, 1.2 mmol) was added MeCN (30 ml), tetrabutylammonium bromide (30 mg, 0.08 mmol), anhydrous sodium carbonate (500 mg, 4.7 mmol), ethyl bromoacetate (0.14 ml, 1.26 mmol) and caesium carbonate (20 mg, 0.06 mmol). This reaction mixture was then stirred overnight at 80° C. Then the solvent was removed under reduced pressure, water and DCM were added and the aqueous phase was extracted three times with DCM. The combined organic phases were then dried, concentrated and purified by flash chromatography [DCM:EtOAc, 1:0, 9:1] to give the title compound 600 mg (99%). NMR (300 MHz) 0.8–1.0 (m, 6H), 1.0–1.8 (m, 11H), 2.2 (s, 3H), 3.2 (q, 2H) 3.75 (brq, 2H), 4.3 (q, 2H), 4.75 (s, 1H), 6.7 (s, 1H), 6.95 (t, 1H), 7.05 (d, 2H), 7.25 (t, 2H), 7.3 (s, 1H).

Method 17

1,1-Dioxo-3-butyl-3-ethyl-5-phenyl-7-methylthio-8-carboxymethoxy-2,3,4,5-tetrahydro-1,5-benzothiazepine To 1,1-dioxo-3-butyl-3-ethyl-5-phenyl-7-methylthio-8-ethoxycarbonylmethoxy-2,3,4,5-tetrahydro-1,5-benzothiazepine (Method 16; 478 mg, 0.95 mmol) was added THF (15 ml), water (3 ml) and LiOH (34 mg, 1.4 mmol). The reaction was then stirred for 1 hour. Then acetic acid (0.2 ml) was added along with water (10 ml) and DCM (10 ml) The aqueous layer were then extracted three times with DCM. The combined organic phases were then dried and concentrated to give the title compound 450 mg (99%). NMR 0.7–0.9 (m, 6H), 1.0–1.7 (m, 8H), 2.2 (s, 3H), 3.2 (q, 2H), 3.7 (m, 2H), 4.8 (s, 2H), 6.65 (s, 1H), 6.95 (t, 1H), 7.05 (d, 2H), 7.25 (t, 2H), 7.35 (s, 1H), 8.4 (brs, 1H).

Method 18–19

The following compounds were synthesised by the procedure of Method 17 using the appropriate acid and amine (source not indicated where commercially available) except two equivalents of LiOH was used and the extraction was performed after 2 hours reaction time using EtOAc.

| Meth | Compound | M/z | SM |
|---|---|---|---|
| 18 | Enantiomer 1 | 510 | Meth 12 |
| 19 | Enantiomer 2 | 510 | Meth 13 |

Method 20

1,1-Dioxo-3-butyl-3-ethyl-5-phenyl-7-mesyl-8-ethoxycarbonylmethoxy-2,3,4,5-tetrahydro-1,5-benzothiazepine To 1,1-dioxo-3-butyl-3-ethyl-5-phenyl-7-methylthio-8-ethoxycarbonylmethoxy-2,3,4,5-tetrahydro-1,5-benzothiazepine (Method 16; 122 mg, 0.24 mmol) was added DCM (3 ml), water (3 ml) and potassium carbonate (120 mg, 0.87 mmol). The reaction mixture was then cooled to 0° C. and m-chloroperoxybenzoic acid (160 mg, 0.51 mmol) was added in one portion. After 5 hours the reaction was quenched with DCM and saturated sodium hydrogen carbonate solution the aqueous phase were then extracted three times with DCM. The combined organic phases were dried, concentrated and purified by flash chromatography [DCM:EtOAc, 9:1] to give the title compound 46 mg (35%). NMR 0.7–0.8 (m, 6H), 1.0–1.65 (m, 11H), 3.2 (q, 2H), 3.3 (s, 3H), 3.7 (brs, 1H), 4.25 (q, 2H), 4.8 (s, 2H), 7.0–7.1 (m, 3H), 7.2–7.3 (m, 2H), 7.5 (s, 2H).

Method 21

1,1-Dioxo-3-butyl-3-ethyl-5-phenyl-7-mesyl-8-carboxymethoxy-2,3,4,5-tetrahydro-1,5-benzothiazepine To 1,1-dioxo-3-butyl-3-ethyl-5-phenyl-7-mesyl-8-ethoxycarbonylmethoxy-2,3,4,5-tetrahydro-1,5-benzothiazepine (Method 20; 46 mg, 0.085 mmol) was added THF (5 ml), water (1 ml) and LiOH (10 mg, 0.4 mmol). The reaction was stirred for 1 hour and then excess acetic acid was added to quench the reaction. Water and DCM were added and the aqueous phase was extracted three times with DCM. The combined organic phases were dried and concentrated to give the title compound 40 mg (91%). NMR 0.7–0.85 (m, 6H), 1.0–1.7 (m, 8H), 3.2 (m, 2H), 3.3 (s, 3H), 3.8 (s, 2H), 4.9 (s, 2H), 5.0 (brs, 1H), 7.05–7.15 (m, 3H), 7.3–7.4 (t, 2H), 7.5 (s; 1H), 7.6 (s, 1H).

Method 22 (Preparation 1)

1,1-Dioxo-3,3-dibutyl-5-phenyl-7-methylthio-8-carboxymethoxy-2,3,4,5-tetrahydro-1,5-benzothiazepine 1,1-Dioxo-3,3-dibutyl-5-phenyl-7-bromo-8-carboxymethoxy-2,3,4,5-tetrahydro-1,5-benzothiazepine (Method 14; 500 mg, 0.93 mmol) was dissolved in DMF (10 ml). Sodium methanethiolate (200 mg, 2.85 mmol) was added and the mixture was stirred for 2 hours at 50° C. Acetic acid (0.4 ml) was added and the solvent was evaporated under reduced pressure. The residue was extracted with EtOAc/water. The EtOAc layer was separated, dried and evaporated under reduced pressure to give, the title compound 450 mg (96%). NMR. (300 MHz) 0.7–0.8 (m, 6H), 1.0–1.6 (m, 12H), 2.2 (s, 2H), 3.2 (brs, 2H), 3.7 (brs, 2H), 4.8 (s, 2H), 6.6 (s, 1H), 6.9–7.1 (m, 3H), 7.2–7.4 (m, 3H).

Method 22 (Preparation 2)

1,1-Dioxo-3,3-dibutyl-5-phenyl-7-methylthio-8-carboxymethoxy-2,3,4,5-tetrahydro-1,5-benzothiazepine A solution of NaOH (4.67 g, 116 mmol) in water (10 ml) was added to a solution of 1,1-dioxo-3,3-dibutyl-5-phenyl-7-methylthio-8-ethoxycarbonyl-2,3,4,5-tetrahydro-1,5-benzothiazepine (Method 114; 15.45 g, 28.71 mmol) in EtOH (160 ml). The solution was stirred for 30 min at room temperature. The solvent was removed under reduced pressure and the residue was partitioned between EtOAc and 1.0 M HCl. The aqueous layer was extracted twice more with EtOAc and the combined organic extracts were washed with brine and concentrated to give the title compound (14.28 g, 98%) as a white powder. NMR (500 MHz, DMSO-$d_6$) 0.65–0.80 (m, 6H), 0.90–1.50 (m, 12M), 2.20 (s, 3H), 3.25 (s, 2H), 3.65 (bs, 2H), 4.80 (s, 2H), 6.70 (s, 1H), 6.80–7.30 (m, 6H), 13.20 (s, 1H).

Method 23–24

The following compounds were synthesised by the procedure of Method 22 (Preparation 1), using the appropriate acid and amine (source not indicated where commercially available) except that the reactions were performed at ambient temperature and in Method 24 for extended reaction time.

| Meth | Compound | M/z | SM |
|---|---|---|---|
| 23 | Enantiomer 1 | 478 | Meth 18 |
| 24 | Enantiomer 2 | 478 | Meth 19 |

Method 25

1,1-Dioxo-3-butyl-3-ethyl-5-phenyl-7-methylthio-8-hydroxy-2,3,4,5-tetrahydro-1,5-benzothiazepine To 1,1-dioxo-3-butyl-3-ethyl-5-phenyl-7-bromo-8-methoxy-2,3,4,5-tetrahydro-1,5-benzothiazepine (WO9616051; 600 mg, 1.29 mmol) were added DMF (5 ml) and sodium methanethiolate (450 mg, 6.42 mmol). The reaction was then heated to 60° C. for 1 hour. The oil bath was then heated to 120° C. for 4 hours. To quench the reaction, the temperature was lowered to room temperature and excess acetic acid was added quickly. The reaction was kept under a flow of nitrogen through sodium hypochlorite for 2 hours. Water and EtOAc were added and the aqueous phase was extracted three times with EtOAc. The combined organic phases were washed with water, dried and concentrated under reduced pressure. The residue was then purified by flash chromatography [DCM:EtOAc, 9:1] to give the title compound 0.5 g (92%). NMR 0.65–0.8 (m, 6H), 0.95–1.6 (m, 8h), 3.1 (q, 2H), 3.6 (brq, 2H), 6.75 (s, 1H), 6.8 (t, 1H), 6.9 (d, 2H), 7.15 (t, 2H), 7.55 (s, 1H).

Method 26

1,1-Dioxo-3,3-dibutyl-5-phenyl-7-methylthio-8-hydroxy-2,3,4,5-tetrahydro-1,5-benzothiazepine To 1,1-dioxo-3,3-dibutyl-5-phenyl-7-bromo-8-methoxy-2,3,4,5-tetrahydro-1,5-benzothiazepine (synthesised by the of WO9616051 for the corresponding 3-butyl-3-ethyl analogue; 40 mg, 0.08 mmol) was added DMF (2 ml), sodium methanethiolate (60 mg, 0.85 mmol) and sodium borohydride (60 mg, 1.6 mmol). The reaction was run overnight at 60° C. Additional sodium borohydride (60 mg, 1.6 mmol) and sodium methanethiolate (60 mg, 0.85 mmol) was added and the temperature was raised to 120° C. The reaction heated at this temperature for 4 hours and then cooled to room temperature. Then acetic acid was added under a flow of nitrogen, through sodium hypochlorite overnight. Water and EtOAc was added and the aqueous phase was extracted three times with EtOAc. The combined organic phases were washed with HCl (1M), dried and concentrated under reduced pressure. The residue was then purified by flash chromatography [EtOAc:heptane, 1:4] to give the title compound 0.34 g (93%). NMR 0.7–0.9 (m, 6H), 1.0–1.6 (m, 12H), 2.2 (s, 3H), 3.1 (s, 2H), 3.4 (s, 2H), 3.7 (brs, 2H), 6.7 (s, 1H), 6.85–7.05 (m, 2H), 7.2–7.4 (m, 2H).

Method 27

2-[(2'R)-2'-(t-Butoxycarbonylamino)-2'-phenylethanoylamino]ethanesulphonic acid ammonium salt 2-Aminoethanesulphonic acid (740 mg, 5.91 mmol) and (2R)-2-(t-butoxycarbonylamino)-2-phenylacetic acid (1.09 g, 4.34 mmol) were dissolved in DMF (20 ml). DIPEA (2.8 ml, 16.1 mmol) and TBTU (1.53 g, 4.78 mmol) were added and the mixture was stirred for 2 hours at 60° C. The solvent was evaporated at reduced pressure. The residue was purified by preparative HPLC using an MeCN/ammonium acetate buffer gradient (5/95 to 100/0) as eluent to give the title compound 589 mg (32%). NMR (CD$_3$OD) 1.43 (s, 9H), 2.85–3.0 (m, 2H), 3.53–3.68 (m, 2H), 5.1 (brs, 1H), 7.25–7.45 (m, 5H).

Method 28

2-((2'R)-2'-amino-2'-phenylethanoylamino)ethanesulphonic acid ammonium salt

2-[(2'R)-2'-(t-Butoxycarbonylamino)-2'phenylethanoylamino]ethanesulphoric acid ammonium salt (Method 27; 589 mg, 1.57 mmol) was dissolved in EtOAc (20 ml) and the mixture was cooled in an ice bath. Hydrogen chloride gas was bubbled through the reaction, the ice bath was removed and the reaction was allowed to stand for 30 minutes at room temperature. The solvent was evaporated at reduced pressure. The residue was then redissolved in EtOAc (20 ml) and cooled in an ice bath. Hydrogen chloride gas was again bubbled through the reaction, the ice bath was removed and the reaction was allowed to stand for 30 minutes at room temperature. The solvent was evaporated at reduced pressure. DIPEA in DCM was added and the mixture was evaporated at reduced pressure. This was repeated twice. The mixture was lyophilised to give the title compound 563 mg (85%) containing 1 equivalent of di-isopropylethylammoniumchloride. NMR (D$_2$O) 1.35–1.38 (m, 15H), 2.96–3.12 (m, 2H), 3.21 (q, 2H), 3.50–3.80 (m, 4H), 5.11 (brs, 1H), 7.45–7.55 (m, 5H).

Method 29

1,1-Dioxo-3,3-dibutyl-5-phenyl-7-methylthio-8-[N-((R)-1'-phenyl-1'-methoxycarbonylmethyl)carbamoylmethoxy]-2,3,4,5-tetrahydro-1,5-benzothiazepine 1,1-Dioxo-3,3-dibutyl-5-phenyl-7-methylthio-8-carboxymethoxy-2,3,4,5-tetrahydro-1,5-benzothiazepine (Method 22; 250 mg, 0.49 mmol), (R)-2-phenylglycine methyl ester hydrochloride (120 mg, 0.60 mmol) and DIPEA (300 mg, 2.3 mmol) were dissolved in DCM (10 ml) and the mixture was stirred for 5 min in room temperature. TBTU (210 mg. 0.65 mmol) was added and the mixture was stirred for 30 min at room temperature. The solvent was evaporated under reduced pressure and the residue was placed on a column and the product was eluted with DCM/EtOAc (90:10) to give the title compound 306 mg (95%). NMR (500 MHz) 0.7–0.8 (m, 6H), 1.0–1.6 (m, 12H), 2.1 (s, 3H) 3.2 brs, 2H), 3.6–3.8 (m, 5H), 4.6 (ABq, 2H, 5.6 (d, 1H), 6.6 (s, 1H), 6.9–7.5 (m, 11H), 7.9 (d, 1H).

Methods 30–45

The following compounds were synthesised by the procedure of Method 29 using the appropriate acid and amine (source not indicated where commercially available) except that the reaction time was extended to 2 hours for some methods.

| Meth | Compound | NMR or m/z | SM |
|---|---|---|---|
| 30 | 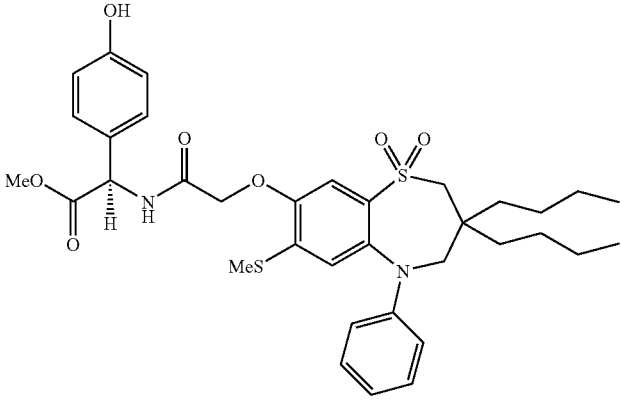 | (300MHz, CD$_3$OD)0.8–0.9(m, 6H), 1.1–1.6(m, 12H), 2.2(s, 3H), 3.3(s, 2H), 3.75(brs, 5H), 4.7–4.8(m, 2H), 5.45(s, 1H), 6.7(s, 1H), 6.8–7.3(m, 9H), 7.45(s, 1H) | Meth 22 |
| 31 | 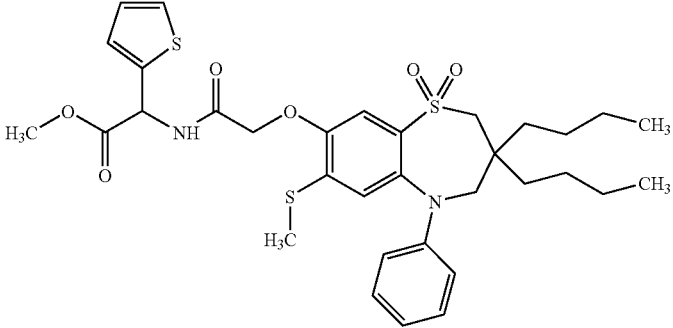 | (300MHz, CD$_3$OD)0.75–0.95 (m, 6H), 1.0–1-6(m, 12H), 2.1 (s, 3H), 3.2(s, 2H), 3.7(s, 5H), 4.65(s, 2H), 5.85(s, 1H), 6.7(s, 1H), 6.9–7.4(m, 9H) | Meth 22 |
| 32 | 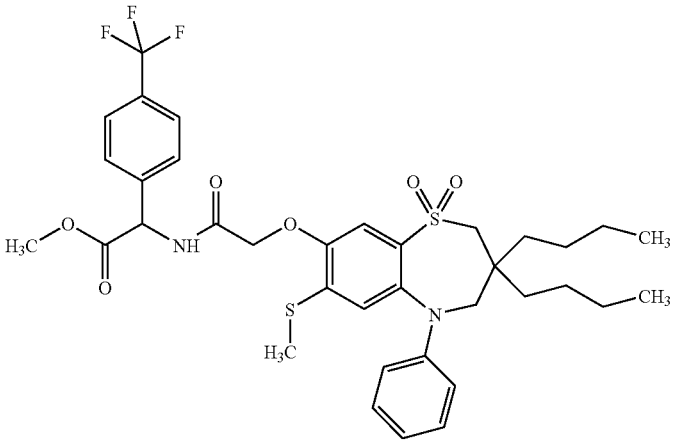 | (300MHz, CD$_3$OD)0.75–0.9 (m, 6H), 1.0–1.6(m, 12H), 2.2 (s, 3H), 3.2(s, 2H), 3.75(s, 5H), 4.7(brs, 2H), 5.7(s, 1H), 6.7(s, 1H), 6.9–7.4(m, 6H), 7.55–7.8 (m, 4H) | Meth 22 and Meth 71 |

-continued

| Meth | Compound | NMR or m/z | SM |
|---|---|---|---|
| 33 | | 0.70–0.85(m, 6H), 0.95–1.75(m, 8H), 1.55–1.75(2d, 3H), 3.05–3.30(m, 2H), 3.55–3.90(m, 2H), 3.70–3.80(2s, 3H)4.75–4.90 (2q, 1H), 5.60(d, 1H), 7.00–7.55 (m, 12H), 7.80–7.95(m, 1H) | Meth 2 |
| 34 | | 0.65–0.85(m, 6H), 0.95–1.65 (m, 8H), 3.00–3.15(m, 2H), 3.50–3.80(m, 2H), 3.70–3.80 (2s, 3H), 5.60(s, 1H), 5.65(d, 1H)7.00–7.60(m, 17H), 8.05–8.20(2d, 1H) | Meth 4 |
| 35 | | (CD$_3$OD)0.75–0.85(m, 6H), 1.00–1.30(m, 8H), 1.35–1.55(m, 4H), 3.20(s, 2H), 3.55(s, 3H), 3.70(s, 3H), 3.75(brs, 2H), 4.60 (ABq, 2H), 5.55(s, 1H), 6.50(s, 1H), 6.95–7.40(m, 10H), 7.50 (s, 1H) | Meth 6 |

-continued

| Meth | Compound | NMR or m/z | SM |
|---|---|---|---|
| 36 | | 707.4 | Ex 12 |
| 37 | | 0.75–0.85(m, 6H), 1.00–1.60 (m, 12H), 3.20(s, 2H), 3.60(s, 3H), 3.75(brs, 2H), 3.75(s, 3H), 4.55(ABq, 2H), 5.85(d, 1H), 6.40(s, 1H), 6.95–7.45(m, 9H), 7.55(s, 1H), 8.05(d, 1H) | Meth 6 |
| 38 | | 0.75–0.85(m, 6H), 1.00–1.60(m, 12H), 2.20(s, 3H), 3.20(s, 2H), 3.75(brs, 2H), 3.80(s, 3H), 4.60 (ABq, 2H), 5.90(d, 1H), 6.65(s, 1H), 6.95–7.45(m, 10H), 7.95 (d, 1H) | Meth 22 |

| Meth | Compound | NMR or m/z | SM |
|---|---|---|---|
| 39 | | (500MHz)0.7–0.8(m, 6H), 1.0–1.5(m, 12H), 3.2(m, 2H), 3.7–3.8(m, 5H), 4.6(ABq, 2H), 5.6(d, 1H), 6.8–7.4(m, 10H), 7.5(s, 1H) | Meth 14 |
| 40 | | (300MHz)0.7–0.8(m, 6H), 1.0–1.6(m, 12H), 3.2(brs, 2H), 3.7–3.8(m, 5H), 4.6(ABq, 2H), 5.6(d, 1H), 6.8(d, 2H), 7.0–7.4(m, 8H), 7.9(d, 1H) | Meth 14 |
| 41 | | 766.4(M-(t-butyl)+2H) | Ex 12 |
| 42 | | 739.3 | Ex 38 |

-continued

| Meth | Compound | NMR or m/z | SM |
|---|---|---|---|
| 43 | | 667 | Meth 22 |
| 44 | | 724 | Ex 18 |
| 45 | | 722.5 | Meth 109 |

Method 46

1,1-Dioxo-3-butyl-3-ethyl-5-phenyl-7-bromo-8-[N-((S)-1'-phenyl-1'-methoxycarbonylmethyl)carbamoylmethoxy]-2,3,4,5-tetrahydro-1,5-benzothiazepine 1,1-Dioxo-8-butyl-3-ethyl-5-phenyl-7-bromo-8-carboxymethoxy-2,3,4,5-tetrahydro-1,5-benzothiazepine (Method 9; 50 mg, 0.098 mmol) was dissolved in DCM (2 ml). Methyl (2S)-amino(phenyl)acetate (19 mg, 0.12 mmol) and DIPEA (0.068 ml, 0.39 mmol) were added and the reaction was stirred for 2 minutes. TBTU (42 mg, 0.13 mmol) was added and the mixture was stirred for 1.5 hours at room temperature. The mixture was put on a pre-packed ISOLUTE column and eluted with 10 ml DCM/EtOAc 8/2 to give the title compound 60 mg (93%). M/z 657.5.

Methods 47–62

The following compounds were synthesised by the procedure of Method 46 (except that the reaction times were overnight) using the appropriate acid and amine (source not indicated where commercially available).

| Meth | Compound | NMR or M/z | SM |
|---|---|---|---|
| 47 | | 609.4 | Meth 10 |
| 48 | | 625.4 | Meth 17 |
| 49 | | 685.3 | Meth 14 |
| 50 | | 609.4 | Meth 10 |

-continued

| Meth | Compound | NMR or M/z | SM |
|---|---|---|---|
| 51 | | 637.4 | Meth 15 |
| 52 | | 657.4 | Meth 21 |
| 53 | | 685.3 | Meth 14 |
| 54 | | 0.73–0.95(m, 6H), 0.98–1.78(m, 8H), 3.12–3.28(m, 2H), 3.6–4.0(m, 5H), 4.60(ABq, 2H), 5.79(d, 1H), 6.0(brs, 1H), 6.54(dd, 1H), 6.83(t, 1H), 6.95(dd, 1H), 7.0–7.5(m, 7H), 8.43(d, NH), 9.32(brs, 1H) | Meth 9 and Meth 74 |

| Meth | Compound | NMR or M/z | SM |
|---|---|---|---|
| 55 | (structure) | 0.75–0.9(m, 6H), 1.0–1.78(m, 8H), 3.10–3.26(m, 2H), 3.63–3.87(m, 8H), 4.56(ABq, 2H), 5.76(d, 1H), 5.99(brs, 1H), 6.38(s, 1H), 6.51(dd, 1H), 6.81(t, 1H), 6.93(dd, 1H), 7.0–7.15(m, 3H), 7.23–7.4(m, 2H), 7.55 (s, 1H), 8.54(d, NH), 9.45(brs, 1H) | Meth 10 and Meth 74 |
| 56 | (structure) | 0.76–0.87(m, 6H), 1.0–1.8(m, 8H), 2.23(s, 3H), 3.1–3.25(m, 2H), 3.6–3.95(m, 5H), 4.61(ABq, 2H), 5.79 (d, 1H), 6.0(brs, 1H), 6.54(dd, 1H), 6.65(s, 1H), 6.83(t, 1H), 6.92–7.1 (m, 4H), 7.23–7.4(m, 3H), 8.37(d, NH), 9.35(brs, 1H) | Meth 17 and Meth 74 |
| 57 | (structure) | (CD$_3$OD)0.76–0.85(m, 6H), 1.02–1.3(m, 8H), 1.36–1.56(m, 4H), 2.16 (s, 3H), 3.24(brs, 2H), 3.66–3.80(m, 5H), 4.71(ABq, 2H), 5.57(s, 1H), 6.71(s, 1H), 6.98(t, 1H), 7.06–7.14 (m, 4H), 7.28(brt, 2H), 7.37–7.45 (m, 3H) | Meth 22 and Meth 75 |
| 58 | (structure) | (CD$_3$OD)0.76–0.85(m, 6H), 1.02–1.28(m, 8H), 1.36–1.56(m, 4H), 1.96(s, 3H), 3.24(brs, 2H), 3.6–3.8 (m, 5H), 4.73(ABq, 2H), 5.76(s, 1H), 6.63(s, 1H), 6.94–7.04(m, 2H), 7.07–7.15(m, 3H), 7.27(t, 2H), 7.31 (s, 1H), 7.37(d, 1H), 7.42(s, 1H), 7.56(d, 1H) | Meth 22 |

-continued
| Meth | Compound | NMR or M/z | SM |
|---|---|---|---|
| 59 | 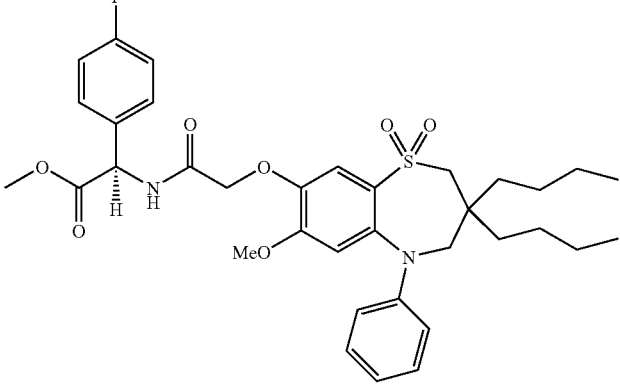 | (CD₃OD)0.80(brt, 6H), 1.0–1.28 (m, 8H), 1.36–1.54(m, 4H), 3.22 (brs, 2H), 3.61(s, 3H), 3.69–3.8 (m, 5H), 4.62(ABq, 2H), 5.56(s, 1H), 6.49(s, 1H), 6.99(brt, 1H), 7.07–7.16(m, 4H), 7.29(brt, 2H), 7.37–7.43(m, 2H), 7.52(s, 1H) | Meth 6 and Meth 75 |
| 60 | 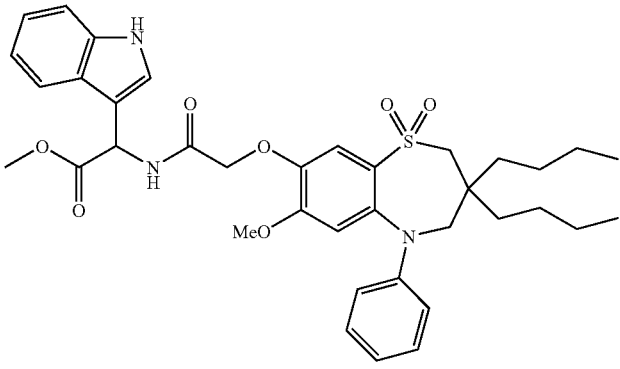 | (CD₃OD)0.75–0.84(m, 6H), 1.0–1.29(m, 8H), 1.35–1.54(m, 4H), 3.20–3.23(m, 5H), 3.65–3.8(m, 5H), 4.64(ABq, 2H), 5.74(s, 1H), 6.34(s, 1H), 6.95–7.04(m, 2H), 7.09–7.15(m, 3H), 7.24–7.31(m, 3H), 7.37(d, 1H), 7.50–7.54(m, 2H) | Meth 6 |
| 61[1] | 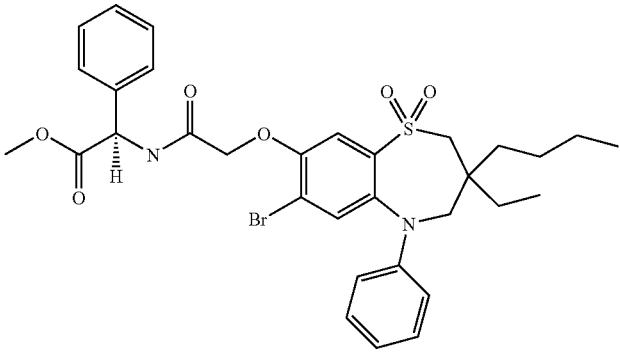 | 0.74–0.83(m, 6H), 0.98–1.7(m, 8H), 3.18(ABq, 2H), 3.60–3.90(m, 5H), 4.59(ABq, 2H), 5.67(d, 1H), 7.0–7.2(m, 4H), 7.2–7.55(m, 8H), 7.91(d, NH) | Meth 9 |
| 62 | 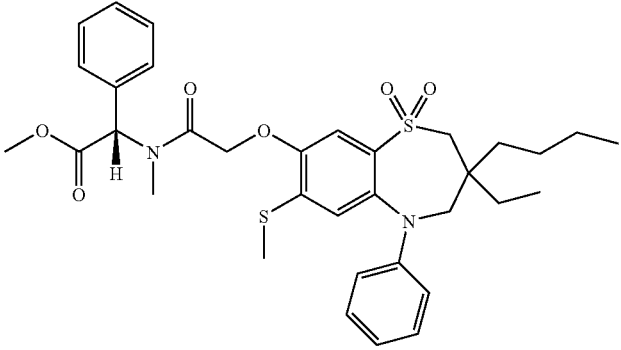 | 639.4 | Meth 17 and Meth 76 |
[1]Eluent was DCM/EtOAc in a stepwise gradient from 100/0, 9/1, 8/2

Method 63

1,1-Dioxo-3,3-dibutyl-5-phenyl-7-methylthio-8-(N-{(R)-1'-phenyl-1'-[N'-(t-butoxycarbonylmethyl)carbamoyl]methyl}carbamoylmethoxy)-2,3,4,5-tetrahydro-1,5-benzothiazepine.

1,1-Dioxo-3,3-dibutyl-5-phenyl-7-methylthio-8-[N-((R)-1'-phenyl-1'-carboxymethyl)carbamoylmethoxy]-2,3,4,5-tetrahydro-1,5-benzothiazepine (Example 1; 110 mg, 0.17 mmol), glycine tert-butyl ester (30 mg, 0.23 mmol) and DIPEA (120 mg, 0.93 mmol) were dissolved in DCM (2 ml). The mixture was stirred for 5 mins at room temperature. TBTU (72 mg, 0.22 mmol) was added and the mixture was stirred for 1 h at room temperature. The solvent was evaporated at reduced pressure and the residue was placed on a column and the product was eluted with DCM/EtOAc (90:10) to give the title compound 122 mg (94%). NMR (300 MHz) 0.7–0.8 (m, 6H), 1.0–1.6 (m, 21H), 2.2 (s, 3H) 3.2 (s, 2H), 3.7–4.0 (m, 4H), 4.6 (ABq, 2H), 5.6 (d, 1H), 6.4 (t, 1H), 6.6 (s, 1H), 6.9–7.5 (m, 11H), 8.1 (d, 1H).

Methods 64–69

The following compounds were synthesised by the procedure of Method 63 using the appropriate acid and amine (source not indicated where commercially available).

| Meth | Compound | NMR or M/z | SM |
|---|---|---|---|
| 64 | | 756.1 | Ex 22 |
| 65 | | (CD₃OD)0.75–0.85(m, 6H), 1.1–1.3(m, 8H), 1.4(s, 9H), 1.45–1.55 (m, 4H), 2.15(s, 3H), 3.25(s, 2H), 3.75(brs, 1H), 3.85(s, 2H), 4.7 (ABq, 2H), 5.5(s, 1H), 6.7(s, 1H), 6.75–7.35(m, 9H), 7.4(s, 1H) | Ex 2 |
| 66 | | 937.9(M–H)⁻ | Ex 2 |

| Meth | Compound | NMR or M/z | SM |
|---|---|---|---|
| 67 | (structure) | 796.4 | Ex 1 |
| 68 | (structure) | | Ex 1 |
| 69 | (structure) | | Ex 1 |

Method 70

1,1-Dioxo-3-butyl-3-ethyl-5-phenyl-7-bromo-8-{N-[(S)-1'-phenyl-1'-(diethoxyphosphoryl)methyl]carbamoylmethoxy}-2,3,4,5-tetrahydro-1,5-benzothiazepine The title compound was synthesised from 1,1-dioxo-3-butyl-3-ethyl-5-phenyl-7-bromo-8-carboxymethoxy-2,3,4,5-tetrahydro-1,5-benzothiazepine (Method 9) and diethyl (S)-amino(phenyl)methylphosphonate by the procedure of Example 33. NMR (600 MHz) 7.77–7.72 (1H, m), 7.47–7.42 (3H, m), 7.36–7.27 (5H, m), 7.14 (1H, s), 7.10–7.03 (2H, m), 5.55–5.48 (1H, m), 4.63–4.51 (2H, m), 4.14–4.02 (2H, m), 3.99–3.92 (1H, m), 3.81–3.60 (3H, m), 3.22–3.10 (2H, m), 1.65–1.25 (8H, m), 1.19–0.95 (6H, m), 0.78–0.73 (6H, m).

Method 71

4-Trifluoromethyl-α-methoxycarbonylbenzylamine

4-Trifluoromethyl-α-carboxybenzylamine (1.4 g, 1.83 mmol) and thionylchloride were added to methanol (8 ml) and the mixture was refluxed for 2 h. The solvent was evaporated under reduced pressure. The residue was suspended in diethyl ether and the product was filtered off, washed with ether and dried to give the title compound 0.34 g (69%).

NMR (300 MHz, DMSO-d$_6$) 3.3 (s, 1H), 5.45 (s, 1H), 7.7–7.9 (m, 4H), 9.25 (brs, 3H).

Method 72

1,1-Dioxo-3-butyl-3-ethyl-5-phenyl-7-methylthio-8-N—{(R)-1'-phenyl-1'-[N-(ethoxycarbonylmethyl)carbamoyl]methyl}carbamoylmethoxy)-2,3,4,5-tetrahydro-1,5-benzothiazepine 1,1-Dioxo-3-butyl-3-ethyl-5-phenyl-7-methylthio-8-[N-((R)-1'-phenyl-1'-carboxymethyl)carbamoylmethoxy]-2,3,4,5-tetrahydro-1,5-benzothiazepine (Example 38; 52 mg, 0.082 mmol) and glycine ethyl ester hydrochloride (18 mg, 0.129 mmol) were dissolved in DCM (2 ml) and DIPEA (0.70 ml, 0.42 mmol) was added. After stirring at ambient temperature for 5 min TBTU (34 mg, 0.11 mmol) was added and the mixture was stirred for 2 hours. The solvent was evaporated and the residue was purified with flash chromatography (DCM:EtOAc 10:3) to give the title compound 50 mg (88%). NMR (500 MHz) 0.86 (m, 6H), 1.10–1.75 (m, 8H), 1.28 (m, 3H), 2.23 (s, 3H), 3.19 (q, 2H), 3.75 (m, 2H), 3.99–4.25 (m, 4H), 4.64 (q, 2H), 5.64 (m, 1H), 6.35 (brs, 1H), 6.69 (s, 1H), 7.03 (t, 1H), 7.09 (d, 1H), 7.29–7.52 (m, 7H), 8.10 (d, 1H).

Method 73

1,1-Dioxo-3-butyl-3-ethyl-5-phenyl-7-methylthio-8-N—{(R)-1'-phenyl-1'-[N-(1"-methoxycarbonyl-1"-phenylmethyl)carbamoyl]methyl}carbamoylmethoxy)-2,3,4,5-tetrahydro-1,5-benzothiazepine The title compound was synthesised by the procedure of Method 72 using 1,1-dioxo-3-butyl-3-ethyl-5-phenyl-7-methylthio-8-[N-((R)-1'-phenyl-1'-carboxymethyl) carbamoylmethoxy]-2,3,4,5-tetrahydro-1,5-benzothiazepine (Example 38) and methyl (2R)-amino(phenyl)acetate hydrochloride.

Method 74

1-(1'-Methoxycarbonyl-1'-aminomethyl)-2,3-dihydroxyphenyl hydrochloride salt 1-(1'-Carboxy-1'-aminomethyl)-2,3-dihydroxyphenyl (40 g, 0.218 mmol) was mixed with methanol (230 ml). HCl gas was bubbled through. The mixture was refluxed for 2 hours. The solvent was evaporated under reduced pressure. The product was crystallised from methanol/EtOAc/diethyl ether to yield 35.5 g (70%) of the title product. NMR (600 MHz, CD$_3$OD) 3.76 (s, 3H), 5.19 (s, 1H), 6.68–6–75 (m, 2H), 6.85 (dd, 1H)

Method 75

(R)-1-(1'-Methoxycarbonyl-1'-aminomethyl)-4-fluorophenyl hydrochloride salt (2R)-amino(4-fluorophenyl)acetic acid (570 mg, 2.77 mmol) was dissolved in methanol (5 ml) and cooled in an ice-bath. Thionyl chloride (2 ml) was added dropwise and temperature was allowed to reach room temperature. After 5 hours the mixture was evaporated under reduced pressure. The procedure was repeated and the reaction was stirred overnight. The mixture was evaporated under reduced pressure to give the title product in a quantitative yield. NMR (500 MHz, CD$_3$OD) 3.84 (s, 3H), 5.26 (s, 1H), 7.26 (t, 2H), 7.53 (dd, 2H).

Methods 76–77

The following compounds were synthesised by the procedure of Method 75 using the appropriate acid and amine (source not indicated where commercially available).

| Meth | Compound | NMR | SM |
| --- | --- | --- | --- |
| 76 | (S)-α-Methylamino-α-methoxycarbonyl-benzyl | (CD$_3$OD)2.63(s, 3H), 3.81 (s, 3H), 5.15(s, 1H), 7.45–7.55(m, 5H) | (S)-α-Methylamino-α-carboxy-benzyl |
| 77[1] | α-Methoxy-carbonyl-N-methyl-benzylamine hydrochloride | (D$_2$O)2.65(s, 3H), 3.81 (s, 3H), 5.15(s, 1H), 7.45–7.48(m, 2H), 7.52–7.59(m, 3H) | (methylamino)(phenyl)acetic acid |

[1]Total reaction time 5 days

Method 78

1,1-Dioxo-3-butyl-3-ethyl-5-phenyl-7-methylthio-8-{N-[(R)-α-(t-butoxycarbonyl)-4hydroxybenzyl]carbamoylmethoxy}-2,3,4,5-tetrahydro-1,5-benzothiazepine tert-Butyl (2R)-amino(4-hydroxyphenyl)acetate (104 mg, 0.47 mmol) and 1,1-dioxo-3-butyl-3-ethyl-5-phenyl-7-methylthio-8-carboxymethoxy-2,3,4,5-tetrahydro-1,5-benzothiazepine (Method 17; 185 mg, 0.39 mmol) were dissolved in DCM (5 ml) and lutidine (0.09 ml, 0.77 mmol) was added. After stirring at room temperature for 5 min o-(7-azabenzotriazol-1-yl)-N,N,N',N'-tetramethyluronium hexafluorophosphate (208 mg, 0.55 mmol) was added and the reaction mixture was stirred at room temperature for 2 hours. Purification with flash chromatography (DCM:EtOAc 10:1→5:1) gave the title compound (175 mg, 66%). NMR (300 MHz) 0.81 (m, 6H), 1.05–1.65 (m, 8H), 1.42 (s, 9H), 2.21 (s, 3H), 3.17 (ABq, 2H), 3.74 (m, 2H), 4.60 (ABq, 2H), 5.22 (brs, 1H), 5.49 (d, 1H), 6.67 (s, 1H), 6.79 (m, 2H), 7.00 (t, 1H), 7.07 (d, 2H), 7.23–7.30 (m, 3H), 7.40 (s, 1H), 7.82 (brd, 1H).

Method 79

The following compounds were synthesised by the procedure of Method 78 using the appropriate starting material.

| Meth | Compound | M/z | SM |
|---|---|---|---|
| 79 | (structure) | 639.3 | Meth 17 and Meth 77 |

Method 80

2-{[(2R)-2-Amino-2-(4-hydroxyphenyl)ethanoyl]amino}ethanesulphonic acid

N-Boc-4-hydroxyphenylglycine (1.00 g, 3.21 mmol) was dissolved in DMF (5 ml) and tetrabutylammonium taurine (2.36 g, 6.42 mmol) was added together with additionally 5 ml DMF. The resulting suspension was cooled on ice and TBTU (1.24 g, 3.85 mmol) was added. The ice bath was removed after 30 min and the mixture was stirred for 2 hours before it was filtered and concentrated. TFA in DCM (20%, 20 ml) was added and the reaction mixture was stirred overnight. Ethanol (20 ml) was added and the solvents evaporated. The crude product was refluxed in ethanol (100 ml) for 1 hour. Filtration yielded the pure title compound as a white solid, 626 mg (71%). NMR (DMSO-$d_6$) 2.4–2.6 (m, 2H), 3.2–3.4 (m, 2H), 4.79 (s, 1H), 6.78 (d, 2H), 7.23 (d, 2H), 8.22 (t, 1H), 8.4 (brs, 3H), 9.7 (s, 1H).

Method 81

1,1-Dioxo-3-butyl-3-ethyl-5-phenyl-7-carboxymethylthio-8-methoxy-2,3,4,5-tetrahydro-1,5-benzothiazepine 1,1-Dioxo-3-butyl-3-ethyl-5-phenyl-7-bromo-8-methoxy-2,3,4,5-tetrahydro-1,5-benzothiazepine (113 mg, 0.24 mmol), $Cs_2CO_3$ (170 mg, 0.52 mmol) and ethyl thioglycolate (0.060 ml, 0.54 mmol) in DMF (4.0 ml) were subjected to microwave irradiation in a Smith Synthesiser at 80° C. for 3 min and then at 90° C. for 8 min. The reaction mixture was diluted with water (250 ml) and extracted with DCM (5×10 ml) and collected organic layers were dried ($MgSO_4$), concentrated and purified on a short column (petroleum ether: EtOAc 4:1→2:1). The resulting product was dissolved in THF (2 ml) and water (2 ml) and NaOH (aq., 0.5 ml, 1 M) was added and the reaction mixture was stirred at room temperature for 2 hours. The reaction was quenched with HCl (1 M) and the reaction mixture was diluted with water (10 ml) and extracted with DCM (3×3 ml). Purification with preparative HPLC yielded the title compound (58 mg, 59%). NMR (300 MHz, $CD_3OD$) 0.81 (m, 6H), 1.00–1.70 (m, 8H), 3.21 (m, 2H), 3.42 (m, 2H), 3.71 (m, 2H), 3.92 (s, 3H), 6.88 (m, 2H), 7.02 (m, 2H), 7.23 (t, 2H), 7.40 (s, 1H).

Method 82

1,1-Dioxo-3-butyl-3-ethyl-5-phenyl-7-ethoxycarbonylmethylthio-8-carboxymethoxy-2,3,4,5-tetrahydro-1,5-benzothiazepine 1,1-Dioxo-3-butyl-3-ethyl-5-phenyl-7-bromo-8-carboxymethoxy-2,3,4,5-tetrahydro-1,5-benzothiazepine (Method 9; 50 mg, 0.098 mmol) and $Cs_2CO_3$ (51 mg, 0.15 mmol) were added to DMF (2.0 ml) and ethyl thioglycolate (0.02 ml, 0.15 mmol) was added. The reaction mixture was subjected to microwave irradiation in a Smith Synthesiser at 150° C. for 5 min. The reaction mixture was diluted with water (100 ml), made acidic with HCl (1 M), extracted with DCM (3×10 ml) and the collected organic layers were dried ($MgSO_4$) to give the crude title compound (54 mg). M/z 550.2.

Method 83 and Method 84

1,1-Dioxo-3-butyl-3-ethyl-5-phenyl-7-bromo-8-hydroxy-2,3,4,5-tetrahydro-1,5-benzothiazepine (Enantiomer 1); and

1,1-Dioxo-3-butyl-3-ethyl-5-phenyl-7-bromo-8-hydroxy-2,3,4,5-tetrahydro-1,5-benzothiazepine (Enantiomer 2)

The two enantiomers of 1,1-dioxo-3-butyl-3-ethyl-5-phenyl-7-bromo-8-hydroxy-2,3,4,5-tetrahydro-1,5-benzothiazepine (WO 96/16051) were obtained by separation of the corresponding racemic mixture using preparative HPLC. The column used was a Chiralpak AD (20×250 mm i.d., 10□m) and the mobile phase was a heptane/IPA mixture in ratio 90/10. The injected racemate (17.3 mg in IPA (1 ml)) was eluted with a flow of 10 ml/min and the chromatogram was followed with UV-detection at 285 nm. Totally 260 mg racemate was separated yielding 121 mg of the first eluting enantiomer (Enantiomer 1) and 115 mg of the second eluting enantiomer (Enantiomer 2). Total yield 91%. Each of the two enantiomers was obtained in 99.4% e.e.

Method 85

(R)-N-Benzyloxycarbonyl-α-[N'-(t-butoxycarbonylmethyl)carbamoyl]benzylamine (R)-N-Benzyloxycarbonyl-α-carboxybenzylamine (10 g, 35.0 mmol) and t-butylglycine hydrochloride (6.3 g, 37.4 mmol) was dissolved in DCM (200 ml) with 2,6-lutidine (8.2 ml, 70.4 mmol). After stirring 5 min at 0° C. TBTU (12.4 g, 38.6 mmol) was added and stirring was continued 1 hour 30 min at 0° C. and 3 hours 45 min at room temperature. The reaction mixture was washed with water (2×100 ml), dried (MgSO$_4$) and purified with flash chromatography (DCM:EtOAc 7:1→5:1) to give the title compound (13 g, 94%). NMR (500 MHz) 1.45 (s, 9H), 3.84 (d, 1H), 4.00 (dd, 1H), 5.10 (m, 2H), 5.28 (brs, 1H), 6.13 (brs, 1H), 6.23 (brs, 1H), 7.30–7.44 (m, 10H).

Method 86

(R)-α-[N-(t-Butoxycarbonylmethyl)carbamoyl]benzylamine (R)-N-Benzyloxycarbonyl-α-[N'-(t-Butoxycarbonylmethyl)carbamoyl]benzylamine (Method 85; 12.8 g, 32.2 mmol) was dissolved in EtOH (99%, 200 ml) and toluene (50 ml). Pd/C (10%, 0.65 g) was added and hydrogenation was performed at atmospheric pressure for 5 hours 30 min at room temperature. The reaction mixture was filtered through diatomaceous earth and the solvents were evaporated to give the title compound (8.4 g, 99%). NMR (600 MHz) 1.45 (s, 9H), 3.93 (m, 2H), 4.54 (s, 1H), 7.31–7.42 (m, 5H), 7.51 (brs, 1H).

Method 87

1,1-Dioxo-3,3-dibutyl-5-phenyl-7-methylthio-8-[N-(S)-α-methoxycarbonylbenzyl) carbamoylmethoxy]-2,3,4,5-tetrahydro-1,5-benzothiazepine 1,1-Dioxo-3,3-dibutyl-5-phenyl-7-methylthio-8-carboxymethoxy-2,3,4,5-tetrahydro-1,5-benzothiazepine (Method 22; 50 mg, 0.099 mmol) was dissolved in DCM (2 ml). (S)-Phenylglycine methyl ester hydrochloride (24.8 mg, 0.123 mmol) and diisopropyl ethyl amine (70 □l, 0.401 mmol) were added. The mixture was stirred for 15 min and then TBTU (38 mg, 0.118 mmol) was added. The reaction was completed after 1.5 h (LC/MS). The crude product was purified by flash chromatography using chloroform/EtOAc (8/2) as the eluent (88.6%; 55.2 mg, 0.064 mmol). M/z 653.

Method 88

1,1-Dioxo-3,3-dibutyl-5-phenyl-7-methylthio-8-[N-{(S)-α-[N'-(methoxycarbonylmethyl) carbamoyl]benzyl}carbamoylmethoxy]-2,3,4,5-tetrahydro-1,5-benzothiazepine 1,1-Dioxo-3,3-dibutyl-5-phenyl-7-methylthio-8-[N-(S)-(α-carboxybenzyl) carbamoylmethoxy]-2,3,4,5-tetrahydro-1,5-benzothiazepine (Example 88; 25 mg, 0.039 mmol) and glycine methyl ester (7.5 mg, 0.059 mmol) were dissolved in DCM (2 ml). Diisopropyl ethyl amine (27 □l, 0.158 mmol) and TBTU (15 mg, 0.047 mmol) were added successively and the mixture was stirred for 2 hours at ambient temperature. The crude product was purified by flash chromatography using DCM/EtOAc (8/2) as eluent 79% yield (22 mg). M/z 710.

Method 89

1,1-Dioxo-3-butyl-3-ethyl-5-phenyl-7-bromo-8-(2-carboxyethoxy)-2,3,4,5-tetrahydro-1,5-benzothiazepine Sodium hydroxide (38 mg, 0.95 mmol) was dissolved in ethanol (2.5 ml) and then 1,1-Dioxo-3-butyl-73-ethyl-5-phenyl-7-bromo-8-hydroxy-2,3,4,5-tetrahydro-1,5-benzothiazepine (WO 96/16051; 200 mg, 0.443 mmol) was added. After stirring at room temperature for 5 min, 3-bromopropionic acid (68 mg, 0.443 mmol) was added and the reaction mixture was refluxed for 20 hours. Acetic acid was added. The solvent was evaporated under reduced pressure and the residue was extracted with EtOAc/water. The organic layer was separated, washed with water, dried and evaporated under reduced pressure. The crude product was purified by column chromatography using DCM/MeOH (100:5) as eluent to give the title compound 89 mg (38%). NMR (CD$_3$OD) 0.75–0.83 (m, 6H), 1.0–1.25 (m, 4H), 1.38–1.65 (m, 4H), 2.82 (m, 2H), 3.26 (s, 2H), 3.50–3.90 (m, 2H), 4.33 (t, 2H), 6.99 (t, 1H), 7.07–7.13 (m, 3H), 7.28 (t, 2H), 7.53 (s, 1H).

Method 90

1,1-Dioxo-3-butyl-3-ethyl-5-phenyl-7-bromo-8-(2-{N-[(R)-α-(t-butoxycarbonyl)benzyl] carbamoyl}ethoxy)-2,3,4,5-tetrahydro-1,5-benzothiazepine To a solution of 1,1-dioxo-3-butyl-3-ethyl-5-phenyl-7-bromo-8-(2-carboxyethoxy)-2,3,4,5-tetrahydro-1,5-benzothiazepine (Method 89; 70 mg, 0.134 mmol) and (R)-α-(t-butoxycarbonyl)benzylamine (J. Amer. Chem. Soc.; EN; 117; 44; 1995; 10879–10888; 35 mg, 0.169 mmol) in DCM (2.5 ml) was added 2,6-lutidine (29 mg, 0.268 mmol) and TBTU (56 mg, 0.174 mmol). The reaction mixture was stirred at room temperature for 2.5 hours, then diluted with DCM. The solution was washed with NaHCO$_3$ (aq, sat), water, dried and the solvent was evaporated under reduced pressure. The residue was suspended in ether/petroleum ether and the crystals filtered to give the title compound 85 mg (89%). NMR (500 MHz) 0.79–0.86 (m, 6H), 1.04–1.28 (m, 4H), 1.35–1.56 (m, 11H), 1.60–1.77 (m, 2H), 2.82 (t, 2H), 3.13–3.25 (m, 2H), 3.72 (brs, 2H), 4.35–4.44 (m, 2H), 5.54 (d, 1H), 6.95 (d, 1H), 7.04 (t, 1H), 7.08 (d, 2H), 7.15 (s, 1H), 7.29–7.43 (m, 6H), 7.52 (s, 1H).

Methods 91–94

The following compounds were synthesised by the procedure of Example 104 using the appropriate starting material (source of amine indicated where not commercially available).

| Meth | Compound | NMR(500MHz) and m/z | SM |
|---|---|---|---|
| 91 | | 0.77–0.86(m, 6H), 1.03–1.62(m, 21H), 2.21(s, 3H), 2.32(dd, 1H), 2.54(dd, 1H), 3.14(s, 2H), 3.74 (brs, 2H), 4.48–4.53(m, 1H), 4.60 (dd, 2H), 5.57(d, 1H), 6.33(d, 1H), 6.67(s, 1H), 7.01(t, 1H), 7.09(d, 2H), 7.17–7.40(m, 21H), 7.50(d, 2H), 8.10(d, 1H); m/z 1040.83 | Ex 1; [1] |
| 92 | | 0.78–0.86(m, 6H), 1.05–1.27(m, 8H), 1.36–1.58(m, 13H), 1.78(s, 3H), 2.23(s, 3H), 2.77–2.92(m, 2H), 3.19(s, 2H), 3.75(brs, 2H), 4.64(dd, 2H), 4.72–4.77(m, 1H), 6.68(s, 1H), 6.81(d, 1H), 7.01(t, 1H), 7.09(d, 2H), 7.27–7.42(m, 6H), 7.50(d, 2H), 8.16(d, 1H); m/z 812.23 | Ex 1; [2] |
| 93 | | 0.74–0.81(m, 6H), 1.0–1.22(m, 8H), 1.29–1.62(m, 13H), 2.13(s, 3H), 2.50–2.64(m, 2H), 3.14(s, 2H), 3.69(brs, 2H), 4.42–4.48(m, 1H), 4.58(dd, 2H), 5.45(d, 1H), 6.13(d, 1H), 6.62(s, 1H), 6.96(t, 1H), 7.04(d, 2H), 7.17–7.21(m, 3H), 7.23–7.37(m, 18H), 7.41(d, 2H), 8.0(d, 1H) | Ex 1; Meth 113 |
| 94 | | 0.81–0.87(m, 6H), 1.06–1.29(m, 8H), 1.39–1.61(m, 4H), 1.78(brs, 2H), 1.94(s, 3H), 2.07–2.17(m, 1H), 2.20–2.27(m, 4H), 3.31(s, 2H), 3.77(brs, 2H), 3.80(s, 3H), 4.65(dd, 2H), 4.76–4.82(m, 1H), 5.65–5.70(m, 1H), 6.69(s, 1H), 7.04(t, 1H), 7.12(d, 2H), 7.29–7.44(m, 7H), 7.52(d, 2H), 8.16(d, 1H) | Ex 1 |

[1] t-butyl L-(S-trityl)cysteinate hydrochloride: Org. Pre. Proced. Int.; 1999, 31: 571–572
[2] S-methyl-L-cysteine tert-butyl ester: Pestic. Sci.; EN; 45; 4; 1995; 357–362

Method 95

3,3-Dibutyl-4-oxo-5-(4-chlorophenyl)-7-bromo-8-methoxy-2,3,4,5-tetrahydro-1,5-benzothiazepine A mixture of 3,3-dibutyl-4-oxo-7-bromo-8-methoxy-2,3,4,5-tetrahydro-1,5-benzothiazepine (WO 95/04534; 1.0 g, 2.5 mmol), 4-bromochlorobenzene (4.78 g, 24.98 mmol), copper bromide (36 mg, 0.25 mmol) and potassium carbonate (0.35 g, 2.5 mmol) was refluxed for 20 hours. The reaction mixture was loaded onto a column and the product eluted with 5% EtOAc/petroleum ether (0.8 g, 63% yield). NMR (500 MHz) 0.86–0.92 (m, 6H), 1.16–1.35 (m, 8H), 1.45–1.65 (m, 4H), 3.16 (s, 2H), 3.96 (s 3H), 7.06–7.10 (m, 2H), 7.19 (s, 1H), 7.29 (s, 1H), 7.33–7.38 (m, 2H). M/z 511.

Method 96

1,1-Dioxo-3,3-dibutyl-4-oxo-5-(4-chlorophenyl)-7-bromo-8-methoxy-2,3,4,5-tetrahydro-1,5-benzothiazepine To a mixture of 3,3-dibutyl-4-oxo-5-(4-chlorophenyl)-7-bromo-8-methoxy-2,3,4,5-tetrahydro-1,5-benzothiazepine (Method 95; 0.67 g, 1.304 mmol), DCM (34 ml), water (34 ml) and potassium carbonate (0.554 g, 4.0 mmol) was added at 0° C. m-chloroperoxybenzoic acid (0.78 g, 3.2 mmol) in one portion. The reaction mixture was stirred at 0° C. for 10 h and then at room temperature for 14 hours. DCM (100 ml) and NaHCO$_3$ (aq, sat; 150 ml) were added. The organic layer was separated, washed with brine, dried and evaporated under reduced pressure to give the title compound 0.68 g (96%). NMR (600 MHz) 0.7–0.92 (m, 6H), 1.0–1.60 (m, 10H), 1.70–1.92 (m, 2H), 2.30–3.7 (m, 2H), 3.99 (s, 3H), 7.16–7.20 (m, 2H), 7.24 (s, 1H), 7.34–7.37 (m, 2H), 7.44 (s, 1H); m/z 543.

Method 97

1,1-Dioxo-3,3-dibutyl-4-oxo-5-(4-chlorophenyl)-7-methylthio-8-methoxy-2,3,4,5-tetrahydro-1,5-benzothiazepine Sodium methanethiolate (0.43 g, 6.08 mmol) was added to a solution of 1,1-dioxo-3,3-dibutyl-4-oxo-5-(4-chlorophenyl)-7-bromo-8-methoxy-2,3,4,5-tetrahydro-1,5-benzothiazepine (Method 96; 0.66 g, 1.22 mmol) in anhydrous DMF (11 ml) under nitrogen. The reaction mixture was stirred at room temperature for 72 hours. The solvent was evaporated under reduced pressure and the residue was extracted with trichloromethane/water. The organic layer was separated, washed with brine, dried and evaporated under reduced pressure. The crude product was purified by column chromatography using DCM as eluent to give the title compound 0.6 g (96%). NMR (500 MHz) 0.80–1.0 (m, 6H), 1.10–1.6 (m, 10H), 1.70–2.0 (m, 2H), 2.28 (s, 3H), 3.37–3.70 (m, 2H), 4.04 (s, 3H), 6.65 (s, 1H), 7.25–7.30 (m, 2H), 7.35–7.42 (m, 3H); m/z 510.4.

Method 98

1,1-Dioxo-3,3-dibutyl-5-(4-chlorophenyl)-7-methylthio-8-methoxy-2,3,4,5-tetrahydro-1,5-benzothiazepine To a solution of 1,1-dioxo-3,3-dibutyl-4-oxo-5-(4-chlorophenyl)-7-methylthio-8-methoxy-2,3,4,5-tetrahydro-1,5-benzothiazepine (Method 97; 0.41 g, 0.79 mmol) in anhydrous ether (15 ml) was added LiAlH$_4$ (0.15 g, 3.97 mmol) under nitrogen. The reaction mixture was stirred at room temperature for 2.5 hours. The reaction flask was cooled to 0° C. and the excess LiAlH$_4$ was quenched by adding water (0.3 ml) and 2 M aqueous NaOH (0.3 ml). The mixture was filtered and the filtrate was dried and evaporated under reduced pressure. The crude product was purified by column chromatography using DCM as eluent to give the title compound 0.265 g (68%). NMR (300 MHz) 0.8–0.90 (m, 6H), 1.0–1.47 (m, 12H), 2.33 (s, 3H), 3.17 (s, 2H), 3.70 (s, 2H), 3.93 (s, 3H), 7.03–7.08 (m, 3H), 7.23–7.32 (m, 3H); m/z 496.

Method 99

1,1-Dioxo-3,3-dibutyl-5-(4-chlorophenyl)-7-methylthio-8-hydroxy-2,3,4,5-tetrahydro-1,5-benzothiazepine To a solution of 1,1-dioxo-3,3-dibutyl-5-(4-chlorophenyl)-7-methylthio-8-methoxy-2,3,4,5-tetrahydro-1,5-benzothiazepine (Method 98; 0.26 g 0.52 mmol) in anhydrous DCM (10 ml) was added boron tribromide (2.63 g, 10.48 mmol) under nitrogen. The reaction mixture was stirred at room temperature for 2.5 h. The reaction flask was cooled to 0° C., water (20 ml) and hydrazine monohydrate (0.5 ml) was added. The organic layer was separated, dried and evaporated under reduced pressure. The crude product was purified by column chromatography using DCM/EtOAc (100:5 and 100:10) as eluent to give the title compound 0.20 g (80%). NMR (500 MHz) 0.85 (t, 6H), 1.03–1.28 (m, 8H), 1.35–1.46 (m, 4H), 2.39 (s, 3H), 3.21 (s, 2H), 3.73 (s, 2H), 7.04 (d, 2H), 7.29–7.34 (m, 3H), 7.44 (s, 1H); m/z 482.

Method 100

1,1-Dioxo-3,3-dibutyl-5-(4-chlorophenyl)-7-methylthio-8-ethoxycarbonylmethoxy-2,3,4,5-tetrahydro-1,5-benzothiazepine Ethyl bromoacetate (0.101 g, 0.604 mmol) was added to a mixture of 1,1-dioxo-3,3-dibutyl-5-(4-chlorophenyl)-7-methylthio-8-hydroxy-2,3,4,5-tetrahydro-1,5-benzothiazepine (Method 99; 0.194 g, 0.402 mmol), anhydrous Na$_2$CO$_3$ (0.192 g, 1.81 mmol) and tetrabutylammonium bromide in MeCN (5 ml). The reaction mixture was refluxed for 3.5 hours. The solvent was evaporated under reduced pressure and the residue was extracted with DCM/water. The organic layer was separated, dried and evaporated under reduced pressure. The crude product was purified by column chromatography using DCM/EtOAc (100:5 and 100:10) as eluent to give the title compound 0.197 g (86%). NMR (300 MHz) 0.80–0.89 (m, 6H), 1.0–1.45 (m, 15H), 2.34 (s, 3H), 3.16 (s, 2H), 3.68 (s, 2H), 4.30 (q, 2H), 4.71 (s, 2H), 7.05–7.11 (m, 3H), 7.19 (s, 1H), 7.29–7.35 (m, 2H).

Method 101

1,1-Dioxo-3,3-dibutyl-5-(4-chlorophenyl)-7-methylthio-8-carboxymethoxy-2,3,4,5-tetrahydro-1,5-benzothiazepine To a solution of 1,1-dioxo-3,3-dibutyl-5-(4-chlorophenyl)-7-methylthio-8-ethoxycarbonylmethoxy-2,3,4,5-tetrahydro-1,5-benzothiazepine (Method 100; 0.195 g, 0.343 mmol) in ethanol (8 ml) was added NaOH (1.03 mmol in 0.5 ml water). The reaction mixture was stirred at room temperature for 70 min and then quenched by adding acetic acid (0.3 ml). The solvent was evaporated under reduced pressure and the residue was extracted with DCM/water. The organic layer was separated, washed with brine, dried and evaporated under reduced pressure to give the title compound 0.169 g (91%). NMR (500 MHz, CD$_3$OD) 0.86 (t, 6H), 1.11–1.28 (m, 8H), 1.37–1.44 (m, 4H), 2.33 (s, 3H), 3.25 (s, 2H), 3.55 (s, 2H), 4.73 (s, 2H), 7.10–7.15 (m, 3H), 7.26 (s, 1H), 7.28–7.32 (m, 2H).

Method 102

1,1-Dioxo-3,3-dibutyl-5-(4-chlorophenyl)-7-methylthio-8-[N-{(R)-α-[N'-(t-butoxycarbonylmethyl)carbamoyl]benzyl}carbamoylmethoxy]-2,3,4,5-tetrahydro-1,5-benzothiazepine To a solution of 1,1-dioxo-3,3-dibutyl-5-(4-chlorophenyl)-7-methylthio-8-carboxymethoxy-2,3,4,5-tetrahydro-1,5-benzothiazepine (Method 101; 100 mg, 0.185 mmol) and (R)-α-[N-(t-butoxycarbonylmethyl)carbamoyl]benzylamine (Method 86; 56 mg, 0.213 mmol) in DCM (4 ml) was added 2,6-lutidine (40 mg, 0.37 mmol) and TBTU (89 mg, 0.28 mmol). The reaction mixture was stirred at room temperature for 2 hours and then EtOAc was added and the solution washed with water. The organic layer was separated, dried and evaporated under reduced pressure. The crude product was purified by column chromatography using DCM/MeOH (100:3) as eluent to give the title compound 0.129 g (89%). NMR (600 MHz) 0.78–82 (m, 6H), 1.01–1.23 (m, 8H), 1.30–1.42 (m, 13H), 2.32 (s, 3H), 3.10–3.16 (m, 2H), 3.62–3.68 (m, 2H), 3.81–3.87 (m, 1H), 3.95–4.03 (m, 1H), 4.52 (dd, 2H), 5.57 (d, 1H), 6.27 (t, 1H), 7.01–7.07 (m, 3H), 7.20–7.43 (m, 8H), 8.02 (d, 1H).

Method 103

3,3-Dibutyl-4-oxo-5-(4-nitrophenyl)-8-methoxy-2,3,4,5-tetrahydro-1,5-benzothiazepine To 3,3-dibutyl-4-oxo-8-methoxy-2,3,4,5-tetrahydro-1,5-benzothiazepine (synthesised by the procedure of WO9616051 for the corresponding 3-butyl-3-ethyl analogue; 2.9 g, 9.0 mmol) was added p-nitrophenylbromide (24 g, 119 mmol), $K_2CO_3$ (1.6 g, 12 mmol) and CuI (180 mg, 0.95 mmol). The reaction mixture was heated to 200° C. overnight. Then it was allowed to cool down to room temperature and the resulting solid was purified by chromatography using DCM as eluent. The fractions containing the product were concentrated under reduced pressure and EtOH (95%) was added and the insoluble p-nitrophenylbromide was then filtered off. The residue was purified again by flash chromatography using DCM as eluent. The product was still not pure so the residue was then purified by flash chromatography using EtOAc:heptane, 1:9 as eluent to give the title compound 2.57 g (64%). NMR (600 MHz) 0.77–0.87 (m, 6H), 1.12–1.31 (m, 8H), 1.4–1.6 (m, 4H), 3.09 (brs, 2H), 3.79 (s, 3H), 6.72–6.83 (m, 2H), 7.18–7.27 (m, 3H), 8.3 (d, 2H).

Method 104

1,1-Dioxo-3,3-dibutyl-4-oxo-5-(4-nitrophenyl)-8-methoxy-2,3,4,5-tetrahydro-1,5-benzothiazepine To 3,3-dibutyl-4-oxo-5-(4-nitrophenyl)-8-methoxy-2,3,4,5-tetrahydro-1,5-benzothiazepine (Method 103; 2.57 g, 5.8 mmol) was added DCM (130 ml), water (130 ml) and $K_2CO_3$ (2.44 g, 17.6 mmol). The reaction mixture was cooled down to 0° C. and m-chloroperoxybenzoic acid (3.42 g, 13.9 mmol) was added in one portion. The reaction was allowed to complete overnight with the temperature slowly rising to room temperature. Then $NaHCO_3$aq (sat) was added and the two layers were separated. The water layer was then extracted three times with DCM. The combined organic layers was dried, filtered and evaporated under reduced pressure. The product was purified by flash chromatography using DCM as eluent to give the title compound 2.4 g (87%). M/z 475.4.

Method 105

1,1-Dioxo-3,3-dibutyl-5-(4-aminophenyl)-8-methoxy-2,3,4,5-tetrahydro-1,5-benzothiazepine To $LiAlH_4$ (5.76 g, 151 mmol) were added THF (200 ml). The reaction mixture was cooled to 0° C. and $H_2SO_4$ (4.06 ml, 76 mmol) were added slowly with a syringe. After the addition was completed the reaction was stirred for 10 minutes, Then 1,1-dioxo-3,3-dibutyl-4-oxo-5-(4-nitrophenyl)-8-methoxy-2,3,4,5-tetrahydro-1,5-benzothiazepine (Method 104; 2.57 g, 5.06 mmol) dissolved in THF (50 ml) was added at 0° C. After vigorous stirring for 1 hour the cooling bath was removed and the reaction was heated to 40° C. overnight. Then $Na_2SO_4 \cdot 10H_2O$ (3–4 teaspoons), water (8 ml), NaOH (15%, aq) (8 ml), water (25 ml) and MeOH (30 ml) were added in that order. The precipitate was removed by filtration and rinsed with DCM/MeOH. The solvent was dried, filtered and concentrated under reduced pressure. The residue was purified by flash chromatography using DCM:EtOAc, 9:1 then 3:1 as eluent to give the title compound 0.6 g (27%). M/z 431.3.

Method 106

1,1-Dioxo-3,3-dibutyl-5-(4-aminophenyl)-8-hydroxy-2,3,4,5-tetrahydro-1,5-benzothiazepine 1,1-Dioxo-3,3-dibutyl-5-(4-aminophenyl)-8-methoxy-2,3,4,5-tetrahydro-1,5-benzothiazepine (Method 105; 918 mg, 2.13 mmol) was dissolved in DMF (dry, 20 ml). Sodium thiomethoxide (810 mg, 11.6 mmol) was added. The reaction mixture was treated at 100–120° C. for four hours then room temperature overnight. Acetic acid (3 ml) was added and the mixture was flushed with nitrogen (g) and the gas was lead through a flask containing sodium hypochlorite in order to destroy the methyl mercaptan formed. Water was added and the water layer was extracted two times with EtOAc. The combined organic layer was washed with brine, dried, filtered and evaporated under reduced pressure. The mixture contained DMF so toluene and brine was added (everything didn't dissolved). The water layer was extracted two times with toluene. The combined organic layers were washed once with brine. The separation funnel was washed with EtOAc in order to dissolve everything. The toluene and EtOAc solutions were combined, dried, filtered and evaporated under reduced pressure. The residue was purified by flash chromatography using DCM:EtOAc, 7:3 as eluent to give the title compound 0.6 g (27%). M/z 417.4.

Method 107

1,1-Dioxo-3,3-dibutyl-5-(4-t-butoxycarbonylaminophenyl)-8-hydroxy-2,3,4,5-tetrahydro-1,5-benzothiazepine 1,1-Dioxo-3,3-dibutyl-5-(4-aminophenyl)-8-hydroxy-2,3,4,5-tetrahydro-1,5-benzothiazepine (Method 106; 600 mg, 1.44 mmol was dissolved in THF (10 ml). Di-t-butyldicarbonate (314 mg, 1.44 mmol) was added and the mixture was stirred at 60° C. for two hours and room temperature for 3 days. The solvent was evaporated under reduced pressure. EtOAc was added and the organic layer was washed once with $KHSO_4$-solution (0.3M, aq) and once with brine, dried, filtered and evaporated under reduced pressure. The residue was purified by flash chromatography using DCM:EtOAc, 9:1 as eluent to give the title compound 0.597 g (80%). M/z 517.3.

Method 108

1,1-Dioxo-3,3-dibutyl-5-(4-t-butoxycarbonylaminophenyl)-8-ethoxycarbonylmethoxy-2,3,4,5-tetrahydro-1,5-benzothiazepine 1,1-Dioxo-3,3-dibutyl-5-(4-t-butoxycarbonylaminophenyl)-8-hydroxy-2,3,4,5-tetrahydro-1,5-benzothiazepine Method 107; 597 mg, 1.16 mmol) was dissolved in MeCN (20 ml), $K_2CO_3$ (480 mg, 3.5 mmol), tetrabutylammoniumbromide (54 mg, 0.17 mmol) and ethyl bromoacetate (167 μl, 1.5 mmol) was added. The mixture was heated to 60° C. overnight. The solvent was evaporated under reduced pressure. EtOAc and water was added and the water layer was extracted two times with EtOAc. The combined organic layer was washed once with brine, dried, filtered and evaporated under reduced pressure to give the title compound 0.617 g (89%). M/z 603.3.

Method 109

1,1-Dioxo-3,3-dibutyl-5-(4-t-butoxycarbonylaminophenyl)-8-carboxymethoxy-2,3,4,5-tetrahydro-1,5-benzothiazepine 1,1-Dioxo-3,3-dibutyl-5-(4-t-butoxycarbonylaminophenyl)-8-ethoxycarbonylmethoxy-2,3,4,5-tetrahydro-1,5-benzothiazepine (Method 108; 607 mg, 1.0 mmol) was dissolved in THF (6 ml), $H_2O$ (6 ml) and LiOH (127 mg, 3.02 mmol, monohydrate) was added. The mixture was stirred for 1 hour. The mixture was poured into water and the solution was acidified using HCl-solution (aq, 1M). The water layer was extracted two times with EtOAc. The combined organic layer was wash once with brine, dried, filtered and evaporated under reduced pressure to give the title compound 0.571 g (99%). M/z 575.4.

Method 110

1,1-Dioxo-3,3-dibutyl-5-(4-aminophenyl)-8-[N-(α-(R)-methoxycarbonylbenzyl)carbamoylmethoxy]-2,3,4,5-tetrahydro-1,5-benzothiazepine 1,1-Dioxo-3,3-dibutyl-5-(4-t-butoxycarbonylaminophenyl)-8-[N-(α-(R)-methoxycarbonylbenzyl)carbamoylmethoxy]-2,3,4,5-tetrahydro-1,5-benzothiazepine (Method 45; 562 mg, 0.78 mmol) was dissolved in DCM (18 ml). TFA (4 ml) was added and the reactions mixture was stirred for 3 hours. The solvent was evaporated under reduced pressure. The residue was partitioned between EtOAc and NaOH solution (1M, aq). The aqueous phase was extracted one more time with EtOAc. The combined organic layer was wash with brine, dried, filtered and evaporated under reduced pressure to give the title compound 440 mg (91%). M/z 622.5.

Method 111

1,1-Dioxo-3,3-dibutyl-5-[4-(N'-t-butylureido)phenyl]-8-[N-(α-(R)-methoxycarbonylbenzyl)carbamoylmethoxy]-2,3,4,5-tetrahydro-1,5-benzothiazepine 1,1-Dioxo-3,3-dibutyl-5-(4-aminophenyl)-8-[N-(α-(R)-methoxycarbonylbenzyl) carbamoylmethoxy]-2,3,4,5-tetrahydro-1,5-benzothiazepine (Method 110; 40 mg, 0.064 mmole) was dissolved in DMF (1 ml). t-Butyl isocyanate (8.3 μl, 0.071 mmol) was added. The reaction mixture was stirred at 60–80° C. overnight. Tert-butyl isocyanate (20 μl, 0.171 mmol) was added. The reaction mixture was stirred at 60–80° C. for 2 days and then room temperature for a few days. The solvent was evaporated under reduced pressure. The product was purified by preparative HPLC using an MeCN/ammonium acetate buffer gradient (5/95 to 100/0) as eluent to give the title product, 30 mg (65%). M/z 721.6.

Method 112

1,1-Dioxo-3-butyl-3-ethyl-5-phenyl-7-methylthio-8-[N-(α-methoxycarbonylmethyl-benzyl)carbamoylmethoxy]-2,3,4,5-tetrahydro-1,5-benzothiazepine The title compound was synthesized from 1,1-dioxo-3-butyl-3-ethyl-5-phenyl-7-methylthio-8-carboxymethoxy-2,3,4,5-tetrahydro-1,5-benzothiazepine (Method 17) and methyl 3-amino-3-phenylpropanoate (Helv. Chim. Acta; EN; 83; 6; 2000; 1256–1267) by the procedure of Example 56. M/z 639.4.

Method 113 t-Butyl D-(S-trityl)cysteinate hydrochloride

To a vigorously stirred suspension of S-trityl-D-cysteine (2.0 g, 5.5 mmol) in t-butyl acetate (35 ml), 70% $HClO_4$ (1.6 ml) was added dropwise. The reaction mixture was stirred at room temperature for 70 min and EtOAc (50 ml) and $NaHCO_3$ (aq, sat) to pH 8.0 were added. The precipitate, unreacted S-trityl-D-cysteine was filtered off. The organic layer was separated, washed with 0.5 M HCl (2×75 ml) and brine, dried and evaporated to give the title compound 2.02 g (81%). NMR (500 MHz): 1.43 (s, 9H), 2.83–2.95 (m, 2H), 3.41–3.48 (m, 1H), 7.21–7.37 (m, 9H), 7.46 (d, 6H).

Method 114

1,1-Dioxo-3,3-dibutyl-5-phenyl-7-methylthio-8-ethoxycarbonyl-2,3,4,5-tetrahydro-1,5-benzothiazepine To a suspension of 1,1-dioxo-3,3-dibutyl-5-phenyl-7-methylthio-8-hydroxy-2,3,4,5-tetrahydro-1,5-benzothiazepine (Method 26; 12.85 g, 28.71 mmol) in MeCN (150 ml) was added ethyl bromoacetate (3.85 ml, 34.6 mmol), tetrabutylammonium bromide (0.925 g, 2.869 mmol) and sodium carbonate (12.85 g, 121.2 mmol). The mixture was heated under reflux for 5 hours. The solvent was removed under reduced pressure and the residue was partitioned between DCM and 0.5 M HCl. The organic layer was washed with brine, dried ($MgSO_4$) and concentrated. Chromatography using DCM/EtOAc (9:1) as eluent gave the desired product (15.45 g) as a tan oil. NMR 0.70–0.85 (m, 6H), 1.00–1.55 (m, 15H), 2.15 (s, 3H), 3.10 (s, 2H), 3.70 (bs, 2H), 4.25 (q, 2H), 4.70 (s, 2H), 6.65 (s, 1H), 6.90–7.30 (m, 6H).

Method 115

1,1-Dioxo-3-butyl-3-ethyl-5-phenyl-8-carboxymethoxy-2,3,4,5-tetrahydro-1,5-benzothiazepine 1,1-Dioxo-3-butyl-3-ethyl-5-phenyl-8-ethoxycarbonylmethoxy-2,3,4,5-tetrahydro-1,5-benzothiazepine (Method 116; 0.48 g, 1.04 mmol) was dissolved in ethanol (10 ml).

NaOH (0.30 g, 7.5 mmol) was added and the mixture was refluxed for 30 min. Acetic acid (1 ml) was added. The solvent was evaporated under reduced pressure and the residue was extracted with DCM/water. The DCM layer was separated, dried and evaporated. 0.44 g (97%) of the title compound was obtained. NMR (300 MHz) 0.7–0.8 (m, 6H), 1.0–1.6 (m, 8H), 3.1–3.3 (m, 2H), 3.5–3.8 (m, 2H), 4.6 (s, 3H), 6.8–7.3 (m, 7H), 7.5 (s, 1H).

Method 116

1,1-Dioxo-3-butyl-3-ethyl-5-phenyl-8-ethoxycarbonylmethoxy-2,3,4,5-tetrahydro-1,5-benzothiazepine 1,1-Dioxo-3-butyl-3-ethyl-5-phenyl-8-hydroxy-2,3,4,5-tetrahydro-1,5-benzothiazepin (WO9616051; 0.40 g, 1.07 mmol), ethyl bromoacetate (0.23 g, 1.38 mmol), sodium carbonate (0.50 g, 4.7 mmol) and tetrabutylammonium bromide (30 mg, 0.093 mmol) were added to MeCN (10 ml). The mixture was refluxed for 18 hours and then evaporated under reduced pressure. The residue was extracted with DCM/water. The DCM layer was separated and evaporated under reduced pressure. The residue was purified by column chromatography. The product was eluted with DCM/EtOAc (90:10). 0.480 g (97%) of the title compound was obtained. NMR (300 MHz) 0.7–0.85 (m, 6H), 1.0–1.7 (m, 11H), 3.1–3.3 (m, 2H), 3.6–3.8 (m, 2H), 4.3 (q, 2H), 4.6 (s, 2H), 6.9–7.3 (m, 7H), 7.5 (d, 1H).

Method 117

1,1-Dioxo-3,3-dipropyl-5-phenyl-7-methylthio-8-hydroxy-2,3,4,5-tetrahydro-1,5-benzothiazepine To a suspension of 1,1-dioxo-3,3-dipropyl-5-phenyl-7-bromo-8-methoxy-2,3,4,5-tetrahydro-1,5-benzothiazepine (prepared according to WO 96/16051 using identical synthetic steps except that the starting material was chosen to give the dipropyl compound instead of the butyl/ethyl compound; 0.756 g, 1.62 mmol) in DMF (40 ml) was added NaSMe (0.605 g, 8.20 mmol, 95%), and the mixture was stirred over night at 120° C. The solvent was removed under reduced pressure and the residue was partitioned between EtOAc and 0.5 M HCl. The aqueous layer was extracted twice more with EtOAc and the combined organic extracts were dried (MgSO$_4$) and concentrated. The title compound was obtained in 0.665 g (98%). NMR (500 MHz, DMSO-d$_6$) 0.60–0.80 (m, 6H), 1.05–1.50 (m, 8H), 2.15 (s, 3H), 3.20 (s, 2H), 3.65 (brs, 2H), 6.65 (s, 1H), 6.75–6.95 (m, 3H), 7.10–7.25 (m, 2H), 7.30 (s, 1H), 10.5 (s, 1H).

Method 118

1,1-Dioxo-3,3-dipropyl-5-phenyl-7-methylthio-8-carboxymethoxy-2,3,4,5-tetrahydro-1,5-benzothiazepine To a suspension of 1,1-dioxo-3,3-dipropyl-5-phenyl-7-methylthio-8-hydroxy-2,3,4,5-tetrahydro-1,5-benzothiazepine (Method 117; 0.665 g, 1.58 mmol) in MeCN (10 ml) was added ethyl bromoacetate (0.262 ml, 2.35 mmol), tetrabutylammonium bromide (0.051 g, 0.158 mmol) and sodium carbonate (0.870 g, 8.21 mmol). The mixture was stirred over night at 80° C. The solvent was removed under reduced pressure and the residue was partitioned between EtOAc and 0.5 M HCl. The organic layer was washed with brine, dried (MgSO$_4$) and concentrated. The residue was filtered through a short silica column (DCM:EtOAc-9:1), concentrated and dissolved in EtOH (10 ml). A solution of NaOH (0.25 g, 6.25 mmol) in water (1 ml) was added and the solution was stirred over night at room temperature. The solvent was removed under reduced pressure and the residue was partitioned between EtOAc and 0.5 M HCl. The aqueous layer was extracted twice more with EtOAc and the combined organic extracts were washed with brine and concentrated. The crude product was purified by preparative HPLC using a MeCN/ammonium acetate buffer to give the title compound in 0.441 g (58%) as a white solid. NMR (DMSO-d$_6$) 0.55–0.75 (m; 6H), 1.05–1.50 (m, 8H), 2.15 (s, 3H), 3.20 (s, 2H), 3.65 (brs, 2H), 4.50 (s, 2H), 6.65 (s, 1H), 6.80–7.00 (m, 3H), 7.15 (s, 1H), 7.15–7.25 (m, 2H).

Example 121

The following illustrate representative pharmaceutical dosage forms containing the compound of formula (I), or a pharmaceutically acceptable salt, solvate, solvate of such a salt or a prodrug thereof (hereafter compound X), for therapeutic or prophylactic use in humans:

| (a): Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph. Eur | 488.5 |
| Magnesium stearate | 1.5 |

| (e): Injection I | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

|  |  |
|---|---|
| (f): Injection II | 10 mg/ml |
| Compound X | 1.0% w/v |
| Sodium phosphate BP | 3.6% w/v |
| 0.1 M Sodium hydroxide solution | 15.0% v/v |
| Water for injection | to 100% |

|  |  |
|---|---|
| (g): Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)–(c) may be enteric coated by conventional means, for Example to provide a coating of cellulose acetate phthalate.

What we claim is:

1. A compound of formula (I):

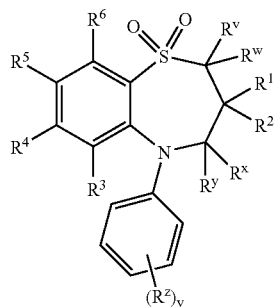

(I)

wherein:

$R^v$ and $R^w$ are independently selected from hydrogen or $C_{1-6}$alkyl;

$R^1$ and $R^2$ are independently selected from $C_{1-6}$alkyl;

$R^x$ and $R^y$ are independently selected from hydrogen or $C_{1-6}$alkyl, or one of $R^x$ and $R^y$ is hydrogen or $C_{1-6}$alkyl and the other is hydroxy or $C_{1-6}$alkoxy;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, ureido, N'—($C_{1-6}$alkyl)ureido, N—($C_{1-6}$alkyl)ureido, N',N'—($C_{1-6}$alkyl)$_2$ureido, N'—($C_{1-6}$alkyl)-N—($C_{1-6}$alkyl)ureido, N',N'—($C_{1-6}$alkyl)$_2$-N—($C_{1-6}$alkyl)ureido, N—($C_{1-6}$alkyl)sulphamoyl and N,N—($C_{1-6}$alkyl)$_2$sulphamoyl;

v is 0–5;

one of $R^4$ and $R^5$ is a group of formula (IA):

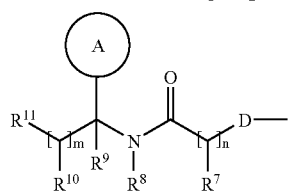

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^3$ and $R^6$ and the other of $R^4$ and $R^5$ may be optionally substituted on carbon by one or more $R^{16}$;

D is —O—, —N($R^a$)—, —S(O)$_b$— or —CH($R^a$)—; wherein $R^a$ is hydrogen or $C_{1-6}$alkyl and b is 0–2;

Ring A is aryl or heteroaryl; wherein Ring A is optionally substituted by one or more substituents selected from $R^{17}$;

$R^7$ is hydrogen, $C_{1-4}$alkyl, carbocyclyl or heterocyclyl; wherein $R^7$ is optionally substituted by one or more substituents selected from $R^{18}$;

$R^8$ is hydrogen or $C_{1-4}$alkyl;

$R^9$ is hydrogen or $C_{1-4}$alkyl;

$R^{10}$ is hydrogen, $C_{1-4}$alkyl, carbocyclyl or heterocyclyl; wherein $R^{10}$ is optionally substituted by one or more substituents selected from $R^{19}$;

$R^{11}$ is carboxy, sulpho, sulphino, phosphono, tetrazolyl, —P(O)(OR$^c$)(OR$^d$), —P(O)(OH)(OR$^c$), —P(O)(OH)(R$^d$) or —P(O)(OR$^c$)(R$^d$) wherein $R^c$ and $R^d$ are independently selected from $C_{1-6}$alkyl; or $R^{11}$ is a group of formula (IB):

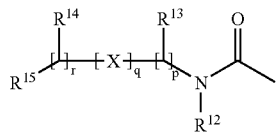

(IB)

wherein:

X is —N($R^q$)—, —N($R^q$)C(O)—, —O—, and —S(O)$_a$—; wherein a is 0–2 and $R^q$ is hydrogen or $C_{1-4}$alkyl;

$R^{12}$ is hydrogen or $C_{1-4}$alkyl;

$R^{13}$ and $R^{14}$ are independently selected from hydrogen, $C_{1-4}$alkyl, carbocyclyl, heterocyclyl or $R^{23}$; wherein said $C_{1-4}$alkyl, carbocyclyl or heterocyclyl may be independently optionally substituted by one or more substituents selected from $R^{20}$;

$R^{15}$ is carboxy, sulpho, sulphino, phosphono, tetrazolyl, —P(O)(OR$^e$)(OR$^f$), —P(O)(OH)(OR$^e$), —P(O)(OH)(R$^e$) or —P(O)(OR$^e$)(R$^f$) wherein $R^e$ and $R^f$ are independently selected from $C_{1-6}$alkyl; or $R^{15}$ is a group of formula (IC):

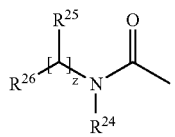

(IC)

wherein:

$R^{24}$ is selected from hydrogen or $C_{1-4}$alkyl;

$R^{25}$ is selected from hydrogen, $C_{1-4}$alkyl, carbocyclyl, heterocyclyl or $R^{27}$; wherein said $C_{1-4}$alkyl, carbocyclyl or heterocyclyl may be independently optionally substituted by one or more substituents selected from $R^{28}$;

$R^{26}$ is selected from carboxy, sulpho, sulphino, phosphono, tetrazolyl, —P(O)(OR$^g$)(OR$^h$), —P(O)(OH)(OR$^g$), —P(O)(OH)(R$^g$) or —P(O)(OR$^g$)(R$^h$) wherein $R^g$ and $R^h$ are independently selected from $C_{1-6}$alkyl;

p is 1–3; wherein the values of $R^{13}$ may be the same or different;

q is 0–1;

r is 0–3; wherein the values of $R^{14}$ may be the same or different;

m is 0–2; wherein the values of $R^{10}$ may be the same or different;

n is 1–3; wherein the values of $R^7$ may be the same or different;

z is 0–3; wherein the values of $R^{25}$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^{16}$, $R^{17}$ and $R^{18}$ may be independently optionally substituted on carbon by one or more $R^{21}$;

$R^{19}$, $R^{20}$, $R^{23}$, $R^{27}$ and $R^{28}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, carbocyclyl, heterocyclyl, sulpho, sulphino, amidino, phosphono, —P(O)(OR$^a$)(OR$^b$), P(O)(OH)(OR$^a$), P(O)(OH)(R$^a$) or —P(O)(OR$^a$)(R$^b$), wherein R$^a$ and R$^b$ independently selected from $C_{1-6}$alkyl; wherein $R^{19}$, $R^{20}$, $R^{23}$, $R^{27}$ and $R^{28}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

or a pharmaceutically acceptable salt, solvate, solvate of such a salt, or an in vivo hydrolysable ester formed on an available carboxy or hydroxy thereof, or an in vivo hydrolysable amide formed on an available carboxy thereof.

2. A compound of formula (I) according to claim 1 wherein $R^v$ and $R^w$ are both hydrogen or a pharmaceutically acceptable salt, solvate, solvate of such a salt, or an in vivo hydrolysable ester formed on an available carboxy or hydroxy thereof, or an in vivo hydrolysable amide formed on an available carboxy thereof.

3. A compound of formula (I) according to either of claims 1 wherein $R^1$ and $R^2$ are independently selected from ethyl, propyl or butyl or a pharmaceutically acceptable salt, solvate, solvate of such a salt, or an in vivo hydrolysable ester formed on an available carboxy or hydroxy thereof, or an in vivo hydrolysable amide formed on an available carboxy thereof.

4. A compound of formula (I) according to claim 1 wherein $R^x$ and $R^y$ are both hydrogen or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

5. A compound of formula (I) according to claim 1 wherein $R^z$ is selected from halo, amino, $C_{1-6}$alkyl, $C_{1-6}$alkoxycarbonylamino or N'—($C_{1-6}$alkyl)ureido or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

6. A compound of formula (I) according to claim 1 wherein v is 0 or 1 or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

7. A compound of formula (I) according to claim 1 wherein $R^3$ is hydrogen or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

8. A compound of formula (I) according to claim 1 wherein the $R^4$ or $R^5$ that is not the group of formula (IA) is selected from hydrogen, halo, $C_{1-4}$alkoxy or $C_{1-4}$alkylS(O)$_a$ wherein a is 0 to 2; wherein that $R_4$ or $R_5$ may be optionally substituted on carbon by one or more $R^{16}$; wherein $R^{16}$ is independently selected from hydroxy, carboxy and N,N—($C_{1-4}$alkyl)$_2$amino or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

9. A compound of formula (I) according to claim 1 wherein $R^5$ is a group of formula (IA) (as depicted in claim 1) and $R^4$ is methylthio or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

10. A compound of formula (I) according to claim 1 wherein $R^6$ is hydrogen or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

11. A compound of formula (I) according to claim 1 wherein in the group of formula (IA):

D is —O— or —S—;

Ring A is phenyl, thienyl or indolyl; wherein Ring A is optionally substituted by one or more substituents selected from halo, hydroxy, methoxy or trifluoromethyl;

$R^7$ is hydrogen, methyl or phenyl;

$R^8$ is hydrogen or methyl;

$R^9$ hydrogen or methyl;

$R^{10}$ is hydrogen;

m is 0–2 wherein the values of $R^{10}$ may be the same or different; and $R^{11}$ is carboxy, —P(O)(OH)(OEt) or a group of formula (IB) (as depicted in claim 1);

or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

12. A compound of formula (I) according to claim 1 wherein in the group of formula (IB):

$R^{12}$ is hydrogen or methyl;

$R^{13}$ is hydrogen, methyl, ethyl, butyl or phenyl or $R^{23}$; wherein $R^{13}$ is optionally substituted by one or more substituents selected from $R^{20}$; $R^{20}$ is hydroxy, methylthio, methoxy, amino, imidazolyl or mercapto; wherein $R^{20}$ may be independently optionally substituted on carbon by one or more hydroxy; $R^{23}$ is carboxy;

X is —NH— or —NHC(O)—;

$R^{14}$ is selected from hydrogen, methyl or phenyl; wherein said methyl or phenyl may be optionally substituted by one or more substituents selected from hydroxy;

$R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from methyl or ethyl or $R^{15}$ is a group of formula (IC) (as depicted in claim 1);

p is 1–3 wherein the values of $R^{13}$ may be the same or different;

q is 0–1; and r is 0–3 wherein the values of $R^{14}$ may be the same or different;

or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

13. A compound of formula (I) according to claim 1 wherein in the group of formula (IC):

$R^{24}$ is hydrogen;
$R^{25}$ is hydrogen;
$R^{26}$ is carboxy; and
z is 1;

or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

14. A compound of formula (I) according to claim 1 wherein:

R$^v$ and R$^w$ are both hydrogen;

$R^1$ and $R^2$ are independently selected from $C_{1-4}$alkyl;

R$^x$ and R$^y$ are both hydrogen;

R$^z$ is selected from halo, amino, $C_{1-6}$alkyl, $C_{1-6}$alkoxycarbonylamino or N'—($C_{1-6}$alkyl)ureido;

v is 0 or 1;

$R^3$ and $R^6$ are hydrogen;

one of $R^4$ and $R^5$ is a group of formula (IA) (as depicted in claim 1) and the other is selected from hydrogen, halo, $C_{1-4}$alkoxy or $C_{1-4}$alkylS(O)$_a$ wherein a is 0 to 2; wherein that $R^4$ or $R^5$ may be optionally substituted on carbon by one or more $R^{16}$; wherein $R^{16}$ is independently selected from hydroxy, carboxy and N,N—($C_{1-4}$alkyl)$_2$amino;

D is —O— or —S—;

$R^7$ is hydrogen, methyl or phenyl;

$R^8$ is hydrogen or methyl;

Ring A is aryl or heteroaryl; wherein Ring A is optionally substituted by one or more substituents selected from $R^{17}$; wherein $R^{17}$ is selected from halo, hydroxy, $C_{1-4}$alkyl or $C_{1-4}$alkoxy; wherein $R^{17}$ may be optionally substituted on carbon by one or more $R^{21}$; wherein $R^{21}$ is selected from halo;

$R^9$ hydrogen or methyl;

$R^{10}$ is hydrogen;

$R^{11}$ is carboxy, —P(O)(OH)(OR$^e$) wherein R$^e$ is selected from $C_{1-4}$alkyl or a group of formula (IB) (as depicted in claim 1);

$R^{12}$ hydrogen or methyl;

X is —NH— or —NHC(O)—;

$R^{13}$ is hydrogen, $C_{1-4}$alkyl, carbocyclyl or $R^{23}$; wherein $R^{13}$ is optionally substituted by one or more substituents selected from $R^{20}$; wherein $R^{20}$ is hydroxy, $C_{1-4}$alkylS(O)$_a$ wherein a is 0, $C_{1-4}$alkoxy, amino, carbocyclyl, heterocyclyl or mercapto; wherein $R^{20}$ may be independently optionally substituted on carbon by one or more $R^{22}$; $R^{22}$ is selected from hydroxy; and $R^{23}$ is carboxy;

$R^{14}$ is selected from hydrogen, $C_{1-4}$alkyl or carbocyclyl; wherein said $C_{1-4}$alkyl or carbocyclyl may be optionally substituted by one or more substituents selected from $R^{20}$; and $R^{20}$ is hydroxy;

$R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-4}$alkyl or $R^{15}$ is a group of formula (IC) (as depicted in claim 1);

$R^{24}$ is hydrogen;

$R^{25}$ is hydrogen;

$R^{26}$ is carboxy;

p is 1–3; wherein the values of $R^{13}$ may be the same or different;

q is 0–1;

r is 0–3; wherein the values of $R^{14}$ may be the same or different;

m is 0–2; wherein the values of $R^{10}$ may be the same or different;

n is 1–2; wherein the values of $R^7$ may be the same or different;

z is 0–1; wherein the values of $R^{25}$ may be the same or different; or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

15. A compound of formula (I) according to claim 1 selected from:

1,1-dioxo-3,3-dibutyl-5-phenyl-7-methylthio-8-N—{(R)-1'-phenyl-1'-[N'-(carboxymethyl) carbamoyl]methyl}carbamoylmethoxy)-2,3,4,5-tetrahydro-1,5-benzothiazepine;

1,1-dioxo-3,3-dibutyl-5-phenyl-7-methylthio-8-N—{(R)-α-[N'-(carboxymethyl)-carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N—{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-N—{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-N—{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N—{(R)-α-[N'-(2-sulphoethyl) carbamoyl]4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-N—{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-N—{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-N—{(R)-α-[N'-(5-carboxypentyl) carbamoyl]benzyl}carbamoylmethoxy)-2,3,4,5-tetrahydro-1,5-benzothiazepine;

1,1-dioxo-3,3-dibutyl-5-phenyl-7-methylthio-8-N—{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N—{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-N—{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-N—{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N—[(R)-α-(N'{(R)-1-[N''—(R)-(2-hydroxy-1-carboxyethyl)carbamoyl]-2-hydroxyethyl}carbamoyl)benzyl]-carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-{N—[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-N—{(R)-α-[N'-(2-methylthio-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N—[(R)-α-(N'-{2-[(methyl)(ethyl) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N—[(R)-α-(N'-{2-[(methyl)(hydroxy) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-N—{(R)-α-[(R)—N'-(2-methylsulphinyl-1-carboxyethyl)carbamoyl]benzyl}carbamoylmethoxy)-2,3,4,5-tetrahydro-1,5-benzothiazepine; and 1,1-dioxo-3,3-dibutyl-5-phenyl-7-methoxy-8-[N—{(R)-α-[N'-(2-sulphoethyl)carbamoyl]-4-hydroxybenzyl}carbamoylmethoxy]-2,3,4,5-tetrahydro-1,5-benzothiazepine;

or a pharmaceutically acceptable salt, solvate, solvate of such a salt, or an in vivo hydrolysable ester formed on an available carboxy or hydroxy thereof, or an in vivo hydrolysable amide formed on an available carboxy thereof.

16. A process for preparing a compound of the formula (I) according to claim 1 which comprises of:

Process 1): oxidising a benzothiazepine of formula (II):

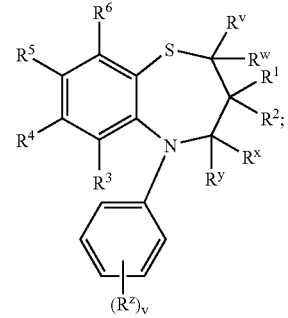

(II)

Process 2): for compounds of formula (I) wherein D is —O—, —NR$^a$ or —S—; reacting a compound of formula (IIIa) or (IIIb):

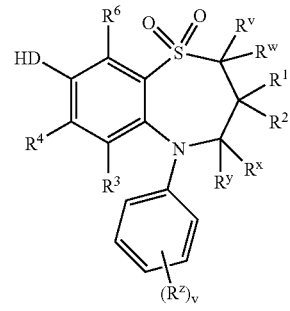

(IIIa)

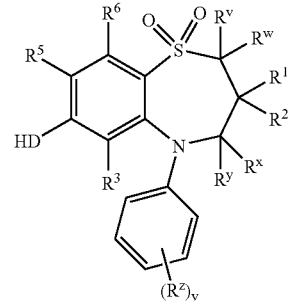

(IIIb)

with a compound of formula (IV):

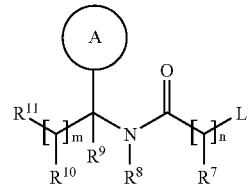

(IV)

wherein L is a displaceable group;

Process 3): reacting an acid of formula (Va) or (Vb):

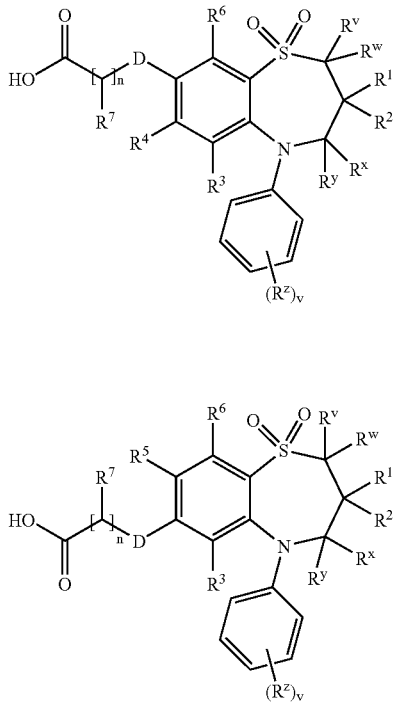

or an activated derivative thereof; with an amine of formula (VI):

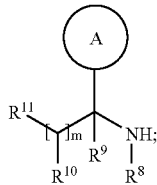

Process 4): for compounds of formula (I) wherein $R^{11}$ is a group of formula (IB); reacting a compound of formula (I) wherein $R^{11}$ is carboxy with an amine of formula (VII):

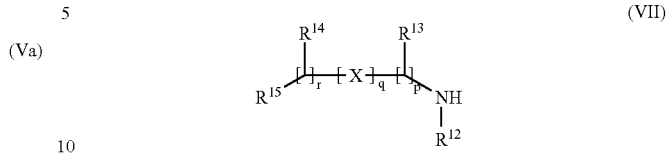

Process 5): for compounds of formula (I) wherein $R^{11}$ is carboxy; deprotecting a compound of formula (VIIIa):

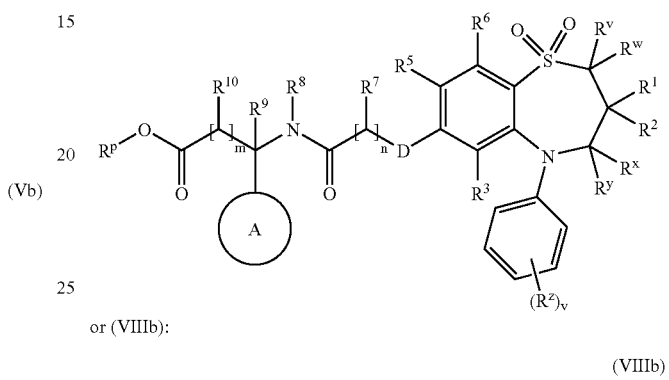

or (VIIIb):

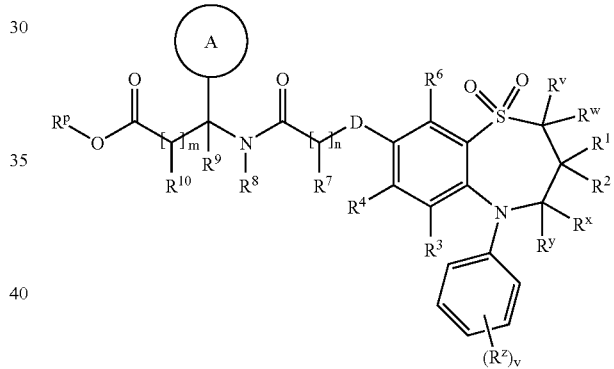

wherein $R^p$ is $C_{1-4}$alkyl;

Process 6): for compounds of formula (I) wherein $R^{11}$ is a group of formula (IB) and $R^{15}$ is carboxy; deprotecting a compound of formula (IXa):

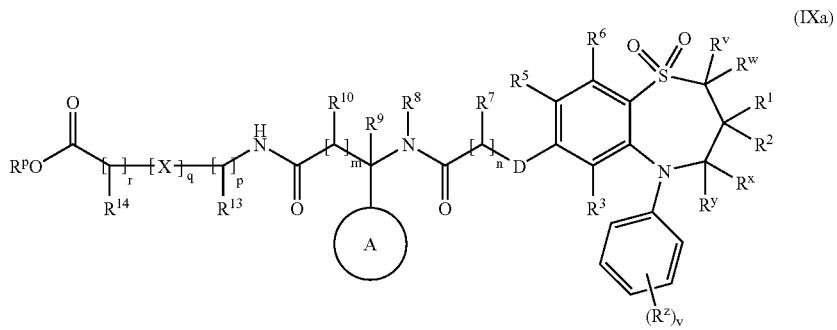

or (IXb):

-continued

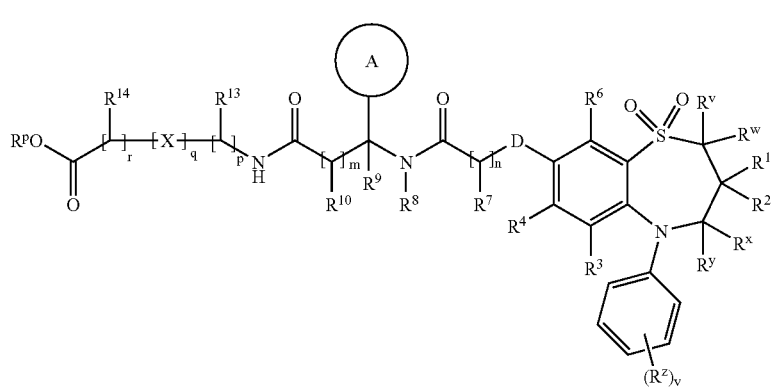
(IXb)

wherein $R^p$ is $C_{1-4}$alkyl;

Process 7) for compounds of formula (I) wherein one of $R^4$ and $R^5$ are independently selected from $C_{1-4}$alkylthio optionally substituted on carbon by one or more $R^{16}$; reacting a compound of formula (Xa) or (Xb):

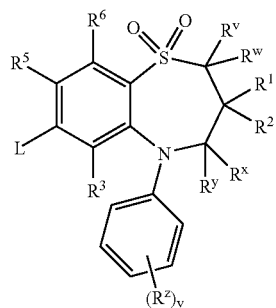
(Xa)

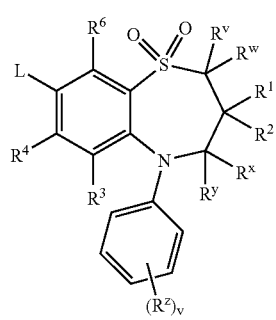
(Xb)

wherein L is a displaceable group; with a thiol of formula (XI):

$$R^y-H \quad (XI)$$

wherein $R^y$ is $C_{1-4}$alkylthio optionally substituted on carbon by one or more $R^{16}$;

Process 8) for compounds of formula (I) wherein $R^{15}$ is a group of formula (IC) reacting a compound of formula (IXa) or (IXb) wherein $R^p$ is hydrogen with a compound of formula (XII):

(XII)

Process 9): for compounds of formula (I) wherein $R^{11}$ is a group of formula (IB) and $R^{15}$ is a group of formula (IC) and $R^{26}$ is carboxy; deprotecting a compound of formula (XIIIa):

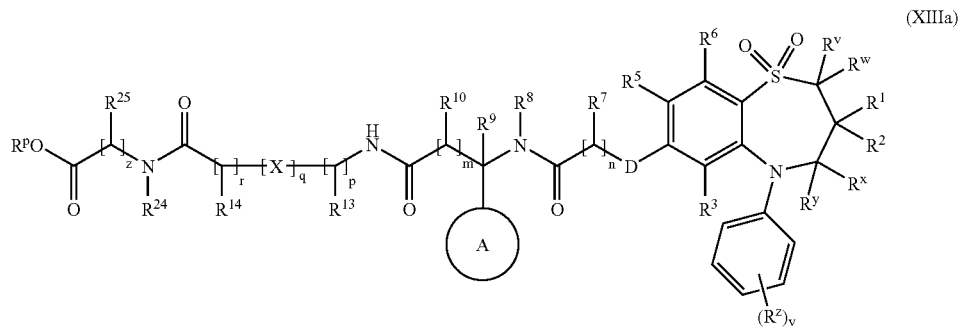
(XIIIa)

or (XIIIb):

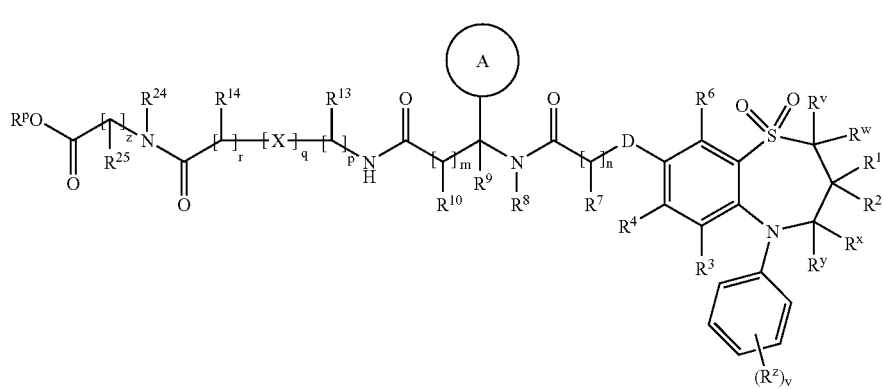

(XIIIb)

and $R^p$ is $C_{1-4}$alkyl;

Process 10): for compounds of formula (I) wherein X is —N($R^q$)C(O); reacting a compound of formula (XIVa):

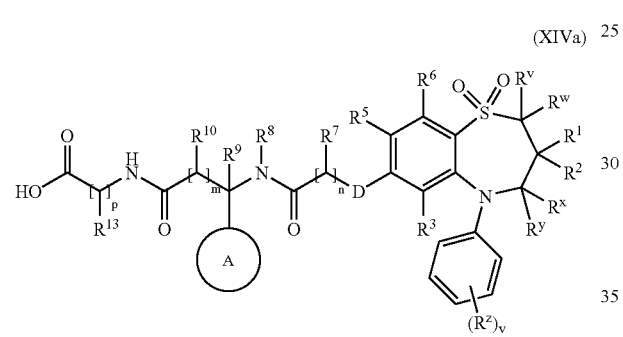

(XIVa)

or (XIVb):

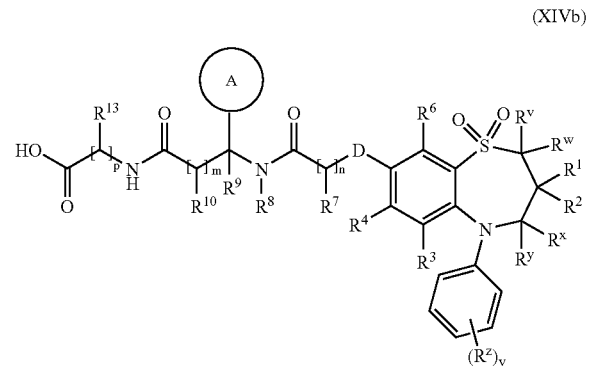

(XIVb)

with a compound of formula (XV):

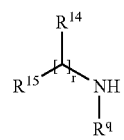

(XV)

and thereafter optionally:
   i) converting a compound of the formula (I) into another compound of the formula (I);
   ii) removing any protecting groups;
   iii) forming a pharmaceutically acceptable salt, solvate, solvate of such a salt, or an in vivo hydrolysable ester formed on an available carboxy or hydroxy thereof, or an in vivo hydrolysable amide formed on an available carboxy thereof.

17. A pharmaceutical composition which comprises a compound of formula (I), or a pharmaceutically acceptable salt, solvate, solvate of such a salt, or an in vivo hydrolysable ester formed on an available carboxy or hydroxy thereof, or an in vivo hydrolysable amide formed on an available carboxy thereof as claimed in any one of claims 1 to 15, in association with a pharmaceutically-acceptable diluent or carrier.

18. A compound of formula (VIIIa), (VIIIb), (IXa), (IXb), (XIIIa) or (XIIIb) as defined in claim 16 or a pharmaceutically acceptable salt, solvate or solvate or such a salt, or an in vivo hydrolysable ester formed on an available carboxy or hydroxy thereof, or an in vivo hydrolysable amide formed on an available carboxy thereof.

\* \* \* \* \*